United States Patent
Burgeson et al.

(10) Patent No.: US 6,635,616 B2
(45) Date of Patent: Oct. 21, 2003

(54) LAMININ 15

(75) Inventors: Robert Burgeson, Palm Springs, CA (US); William Brunken, Canton, MA (US); Marie-France Champliaud, Lugny (FR); Dale Hunter, Canton, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 09/845,583

(22) Filed: Apr. 30, 2001

(65) Prior Publication Data

US 2002/0142954 A1 Oct. 3, 2002

Related U.S. Application Data

(60) Provisional application No. 60/200,863, filed on May 1, 2000.

(51) Int. Cl.$^7$ .......................... A61K 38/39; C07K 14/78
(52) U.S. Cl. .............................. 514/2; 514/8; 530/353; 530/395
(58) Field of Search .............................. 530/395; 514/2, 514/8, 12

(56) References Cited

U.S. PATENT DOCUMENTS 5,610,031 A   3/1997   Burgeson et al. .......... 435/69.1

OTHER PUBLICATIONS

Libby et al, Laminin expression in adult and developing retinae: evidence of two novel CNS laminins. J. Neurosci. 20:6517–6528, Sep. 1, 2000.*
Tunggal et al, Laminins: structure and genetic regulation. Microscopy Research and Technology 51:214–227, 2000.*
Colognato et al, Form and Functions: the laminin family of heterotrimers. Developmental Dynamics 218:213–234, 2000.*
Aumailley et al, Laminins: a family of diverse multifunctional molecules of basement membranes. J. Invest. Dermatol. 106:209–214, 1996.*
Bunt–Milam and Saari, "Immunocytochemical Localization of Two Retinoid–binding Proteins in Vertebrate Retina", *J Cell Biol.* (1983) 97:703–712.
Cohen et al., "The Role of Laminin and the Laminin/Fibronectin Receptor Complex in the Outgrowth of Retinal Ganglion Cell Axons", *Dev Biol.* (1987) 22: 407–418.
Engvall et al., "Mapping of Domains in Human Laminin Using Monoclonal Antibodies: Localization of the Neurite–promoting Site", (1986) *J Cell Biol* 103: 2457–2465.
Hunter et al., "A laminin–like adhesive protein concentrated in the synaptic cleft of the neuromuscular junction", *Nature* (1989) 338:229–234.
Hunter et al., "S–Laminin Expression in Adult and Developing Retinae: A Potential Cue for Photoreceptor Morphogenesis", *Neuron* (1992) 8:399–413.

Hunter and Brunken, "Laminins Modulate Neuronal Phenotype in the Rat Retina", *Mol. Cell Neurosci.* (1997) 10:7.
Kalhmki et al., "A Trucncated Laminin Chain Homologous to the B2 Chain: Structure, Spatial Expression, and Chromosomal Assignment", *J Cell Biol* . (1992) 119:679.
Koch et al., "Characterization and Expression of the Laminin 3 Chain: A Novel, Non–Basement Membrane–associated, Laminin Chain", *J Cell Biol* (1999) 145:605.
Kompa et al., "Aachen–Keratoprosthesis as temporary implant . . . ", (2000) *Int J Artif Organs* 23(5):345–8.
Libby et al., "Developmental Expression of Laminin B2 in Rat Retina", *Invest Ophthalmol Vis Sci* (1996) 37: 165 1.
Libby et al., "Disruption of Laminin B2 Chain Production Causes Alterations in Morphology and Function in the CNS", *J Neurosci.* (1999) 19: 9399.
Libby et al., "Identification of the Cellular Source of laminin B2 in Adult and Developing Vertebrate Retinae", *J Comp Neural* (1997) 389: 355.
Liesi, "Extracellular matrix and neuronal movement", *Experientia* (1990) 46:900.
Liesi and Silver, "Is Astrocyte Laminin involved in Axon Guidance in the Mammalian CNS?", *Dev. Biol.* (1988) 130:774.
Marinkovich et al., "The Anchoring Filament Protien Kalinin IS Synthesized and Secreted as a High Molecular Weight Precursor", *J Biol. Chem.* (1992) 267:17900.
Miner et al., "The Laminin Chains: Expression, Developmental Transitions, and Chromosomal Locations of $\alpha$1–5, Identification of Heterotrimeric Laminins 8–11, and Cloning of a Novel $\alpha$3 Isoform", 1997, *J Cell Biol.* 137:685.
Miner et al., "Molecular Cloning of a Novel Laminin Chain, $\alpha$5, and Widespread Expression in Adult Mouse Tissues", *J Biol. Chem.* (1995) 270: 28523.
Ramussen, "A morphometric Study of the Muller Cell Cytoplasm in the Rat Retina", *J Ultrustruct Res.* (1972) 39:413.
Rouselle et al., "Kalinin: An Epithelium–Specific Basement Membrane Adhesion Molecule That is A Component of Anchoring Filament", *J Cell Biol.* (1991) 114:567–576.
Sanes et al., "Molecular Heterogeneity of Basal Laminae: Isoforms of Laminin and Collagen IV at the Neuromuscular Junction and Elsewhere", *J Cell Biol* (1990) 111:1685.
Sanes et al., "The Basal Lamina of the Neuromuscular Junction", (1983) *Cold Spring Harb. Symp. Quant Biol.* 48: 667.
Sanes, "Extracellular Matrix Molecules That Influence Neural Development", *Ann Rev. Neurosci.* (1989) 12:491.
Sarthy and Fu, "Localization of laminin B1 mRNA in Retinal Ganglion Cells by In Situ Hybridization", *J Cell Biol.* (1990) 110:2099.

(List continued on next page.)

Primary Examiner—Gary Kunz
Assistant Examiner—Ruixiang Li
(74) *Attorney, Agent, or Firm*—Fish & Richardson P.C.

(57) ABSTRACT

The present invention features a novel member of the laminin family, i.e., laminin 15, the methods of making these molecules, and the methods of using these molecules in treating neural disorders, e.g., retinal disorders.

3 Claims, 16 Drawing Sheets

OTHER PUBLICATIONS

Sugiyama et al., "Cloning and expression of the mouse laminin 2 (B2t) chain responsible for muscular dystropy and dysmyelination in dy$^{2J}$ mice", *Eur. J Biochem.* (1995) 228:120.

Sunada et al., "Identification of a novel mutant transcript of laminin 2 chain gene . . . ", *Hum. Mol. Genet.* (1995) 4:1055.

Tiger et al., "Presence of Laminin 5 Chain and Lack of Laminin 1 Chain during Human Muscle Development and in Muscular Dystrophies", J Biol. Chem. (1997) 272: 28590.

Timpl, "Macromolecular Organization of basemanet membranes", *Curr Opin Cell Biol* (1996) 8: 618.

Toti et al., "Localization of laminin chains in the himan retina: possible implications for congenital muscular dystrophy associated with α2–chain of Laminin deficiency", Neurosci. Disord. (1997) 7:21.

Utani et al., "Mouse Kalinin B1 (Laminin 3 chain): Cloning and Tissue Distribution", *Lab Invest.* (1995) 72:300.

Xu et al., "Murine muscular dystrophy caused by a mutation in the laminin 2 (Lama2) gene", *Nut. Genet.* (1994)8:297.

Zhou, "Four patterns of laminin–immunoreactive structure in developing rat brain", *Dev. Brain Res.* (1990) 55:191–201).

Zrenner et al., "The Development of Subretinal Microphotodiodes for Replacements of Degenerated Photoreceptors", *Ophthalmic Res* 1997;295(5):269.

Zrenner et al., "Can subretinal microphotodiodes successfully replace degenerated photoreceptors?", *Vision Res* (1999) 39(15):2555.

* cited by examiner

Amino Acid Sequence and Nucleotide Sequence Encoding Murine Alpha5 Chain

DLYCKLVGGPVAGGDPNQTIQGQYCDICTAANSNKAHPVSNAIDGTERWWQSP
PLSRGLEYNEVNVTLDLGQVFHVAYVLIKFANSPRPDLWVLERSTDFGHTYQPW
QFFASSKRDCLERFGPRTLERITQDDDVICTTEYSRIVPLENGEIVVSLVNGRPGAL
NFSYSPLLRDFTKATNIRLRFLRTNTLLGHLMGKALRDPTVTRRYYYSIKDISIGG
RCVCHGHADVCDAKDPLDPFRLQCACQHNTCGGSCDRCCPGFNQQPWKPATTD
SANECQSCNCHGHAYDCYYDPEVDRRNASQNQDNVYQGGGVCLDCQHHTTGI
NCERCLPGFFRAPDQPLDSPHVCRPCDCESDFTDGTCEDLTGRCYCRPNFTGELC
AACAEGYTDFPHCYPLPSFPHNDTREQVLPAGQIVNCDCNAAGTQGNACRKDPR
LGRCVCKPNFRGAHCELCAPGFHGPSCHPCQCSSPGVANSLCDPESGQCMCRTG
FEGDRCDHCALGYFHFPLCQLCGCSPAGTLPEGCDEAGRCQCRPGFDGPHCDRC
LPGYHGYPDCHACACDPRGALDQQCGVGGLCHCRPGNTGATCQECSPGFYGFP
SCIPCHCSADGSLHTTCDPTTGQCRCRPRVTGLHCDMCVPGAYNFPYCEAGSCH
PAGLAPANPALPETQAPCMCRAHVEGPSCDRCKPGYWGLSASNPEGCTRCSCDP
RGTLGGVTECQGNGQCFCKAHVCGKTCAACKDGFFGLDYADYFGCRSCRCDV
GGALGQGCEPKTGACRCRPNTQGPTCSEPAKDHYLPDLHHMRLELEEAATPEGH
AVRFGFNPLEFENFSWRGYAHMMAIQPRIVARLNVTSPDLFRLVFRYVNRGSTS
VNGQISVREEGKLSSCTNCTEQSQPVAFPPSTEPAFVTVPQRGFGEPFVLNPGIWA
LLVEAEGVLLDYVVLLPSTYYEAALLQHRVTEACTYRPSALHSTENCLVYAHLP
LDGFPSAAGTEALCRHDNSLPRPCPTEQLSPSHPPLATCFGSDVDIQLEMAVPQG
QYVLVVEYVGEDSHQEMGVAVHTPQRAPQQGVLNLHPCYSSLCRSPARDTQH
HLAIFHLDSEASIRLTAEQAHFFLHSVTLVPVEEFSTEFVEPRVFCVSSHGTFNPSS
AACLASRFPKPPQPIILKDCQVLPLPPDLPLTQSQELSPGAPPEGPQPRPPTAVDPN
AEPTLLRHPQGTVVFTTQVPTLGRYAFLLHGYQPVHPSFPVEVLINGGRIWQGHA
NASFCPHGYGCRTLVLCEGQTMLDVTDNELTVTVRVPEGRWLWLDYVLIVPED
AYSSSYLQEEPLDKSYDFISHCATQGYHISPSSSSPFCRNAATSLSLFYNNGALPC
GCHEVGAVSPTCEPFGGQCPCRGHVIGRDCSRCATGYWGFPNCRPCDCGARLCD
ELTGQCICPPRTVPPDCLVCQPQSFGCHPLVGCEECNCSGPGVQELTDPTCDMDS
GQCRCRPNVAGRRCDTCAPGFYGYPSCRPCDCHEAGTMASVCDPLTGQCHCKE
NVQGSRCDQCRVGTFSLDAANPKGCTRCFCFGATERCGNSNLARHEFVDMEGW
VLLSSDRQVVPHEHRPEIELLHADLRSVADTFSELYWQAPPSYLGDRVSSYGGTL
HYELHSETQRGDIFIPYESRPDVVLQGNQMSIAFLELAYPPPGQVHRGQLQLVEG
NFRHLETHNPVSREELMMVLAGLEQLQIRALFSQTSSSVSLRRVVLEVASEAGRG
PPASNVELCMCPANYRGDSCQECAPGYYRDTKGLFLGRCVPCQCHGHSDRCLP
GSGICVGCQHNTEGDQCERCRPGFVSSDPSNPASPCVSCPCPLAVPSNNFADGCV
LRNGRTQCLCRPGYAGASCERCAPGFFGNPLVLGSSCQPCDCSGNGDPNMIFSD
CDPLTGACRGCLRHTTGPHCERCAPGFYGNALLPGNCTRCDCSPCGTETCDPQS
GRCLCKAGVTGQRCDRCLEGYFGFEQCQGCRPCACGPAAKGSECHPQSGQCHC
QPGTTGPQCLECAPGYWGLPEKGCRRCQCPRGHCDPHTGHCTPPGLSGERCDT
CSQQHQVPVPGKPGGHGIHCEVCDHCVVLLLDDLERAGALLPAIREQLQGINASS
AAWARLHRLNASIADLQSKLRRPPGPRYQAAQQLQTLEQQSISLQQDTERLGSQ
ATGVQGQAGQLLDTTESTLGRAQKLLESVRAVGRALNELASRMGQGSPGDALV
PSGEQLRWALAEVERLLWDMRTRDLGAQGAVAEAELAEAQRLMARVQEQLTS
FWEENQSLATHIRDQLAQYESGLMDLREALNQAVNTTREAEELNSRNQERVKE
ALQWKQELSQDNATLKATLQAASLILGHVSELLQGIDQAKEDLEHLAASLDGA

FIG. 1A

WTPLLKRMQAFSPASSKVDLVEAAEAHAQKLNQLAINLSGIILGINQDRFIQRAV
EASNAYSSILQAVQAAEDAAGQALRQASRTWEMVVQRGLAAGARQLLANSSAL
EETILGHQGRLGLAQGRLQAAGIQLHNVWARKNQLAAQIQEAQAMLAMDTSET
SEKIAHAKAVAAEALSTATHVQSQLQGMQKNVERWQSQLGGLQGQDLSQVER
DASSSVSTLEKTLPQLLAKLSRLENRGVHNASLALSANIGRVRKLIAQARSAASK
VKVSMKFNGRSGVRLRPPRDLADLAAYTALKFHIQSPVPAPEPGKNTGDHFVLY
MGSRQATGDYMGVSLRNQKVHWVYRLGKAGPTTLSIDENIGEQFAAVSIDRTL
QFGHMSVTVEKQMVHEIKGDTVAPGSEGLLNLHPDDFVFYVGGYPSNFTPPEPL
RFPGYLGCIEMETLNEEVVSLYNFEQTFMLDTAVDKPCARSKATGDPWLTDGSY
LDGSGFARISFEKQFSNTKRFDQELRLVSYNGIIFFLKQESQFLCLAVQEGTLVLF
YDFGSGLKKADPLQPPQALTAASKAIQVFLLAGNRKRVLVRVERATVFSVDQDN
MLEMADAYYLGGVPPEQLPLSLRQLFPSGGSVRGCIKGIKALGKYVDLKRLNTT
GISFGCTADLLVGRTMTFHGHGFLPLALPDVAPITEVVYSGFGFRGTQDNNLLYY
RTSPDGPYQVSLREGHVTLRFMNQEVETQRVFADGAPHYVAFYSNVTGVWLYV
DDQLQLVKSHERTTPMLQLQPEEPSRLLLGGLPVSGTFHNFSGCISNVFVQRLRG
PQRVFDLHQNMGSVNVSVGCTPAQLIETSRATAQKVSRRSRQPSQDLACTTPWL
PGTIQDAYQFGGPLPSYLQFVGISPSHRNRLHLSMLVRPHAASQGLLLSTAPMSG
RSPSLVLFLNHGHFVAQTEGPGPRLQVQSRQHSRAGQWHRVSVRWGMQQIQLV
VDGSQTWSQKALHHRVPRAERPQPYTLSVGGLPASSYSSKLPVSVGFSGCLKKL
QLDKQPLRTPTQMVGVTPCVSGPLEDGLFFPGSEGVVTLELPKAKMPYVSLELE
MRPLAAAGLIFHLGQALATPYMQLKVLTEQVLLQANDGAGEFSTWVTYPKLCD
GRWHRVAVIMGRDTLRLEVDTQSNHTTGRLPESLAGSPALLHLGSLPKSSTARPE
LPAYRGCLRKLLINGAPVNVTASVQIQGAVGMRGCPSGTLALSKQGKALTQRHA
KPSVSPLLWH

| | |
|---|---|
| 1 | gacctctact gcaagctggt tggggggtccg gtggctggcg gagatcccaa tcagacaatc |
| 61 | cagggccagt actgtgacat ctgtacagct gccaacagca acaaggcaca ccctgtgagc |
| 121 | aacgccatcg atggcacgga gcgctggtgg cagagcccac ccctgtcccg tggcctggag |
| 181 | tacaatgagg tcaacgtcac actggacctg ggccaggtgt tccatgtggc ctatgtgctc |
| 241 | atcaagtttg ccaactcacc tcggcctgac ctctgggtgc tggagcggtc cacagacttc |
| 301 | ggtcacactt atcagccgtg gcagttcttt gcctcctcca agagggattg tttggagcgg |
| 361 | tttggacctc ggactctaga gcgcatcacg caggacgacg acgtcatctg caccacagaa |
| 421 | tactcgcgaa tagtgccttt ggagaatggc gagattgtgg tgtccttggt aaatgggcgc |
| 481 | cctggggcct tgaacttctc ctactcaccg ttacttcgag acttcaccaa agccaccaac |
| 541 | atccgcttgc ggtttctgcg aaccaacacg ctactgggcc acctcatggg caaggcgctg |
| 601 | cgggacccca cagtcacccg caggtattat tacagcatca agacatcag cattggtggg |
| 661 | cgctgtgtct gtcatggcca cgcagatgtc tgtgacgcca aggaccatt ggatcctttc |
| 721 | aggctgcagt gtgcctgcca gcacaataca tgtggaggct cttgtgaccg atgctgtcca |
| 781 | ggcttcaacc agcagccgtg gaagcccgcc accacggaca cgccaatga gtgccagtcc |
| 841 | tgcaattgcc acggccatgc ctacgactgt tactacgacc ctgaggtgga tcggcgcaat |
| 901 | gccagccaga accaggacaa cgtgtaccag ggtggaggtg tctgcctgga ttgccagcat |
| 961 | cacactacgg gtatcaactg tgagcgttgt ctgcctggct tcttccgtgc cctgaccag |
| 1021 | cctctcgact cacctcatgt ctgtcggccc tgcgactgtg agtcagactt cacggatggg |
| 1081 | acctgtgaag acttgacggg ccgctgttac tgcaggccga acttcacagg agagctatgt |
| 1141 | gctgcctgcg ctgagggcta cacggacttc caacactgct accctctgcc ttcatttcct |

FIG. 1B

| | |
|---|---|
| 1201 | cacaatgaca cgagagaaca ggtgcttccc gctggacaaa tcgtgaactg tgattgcaat |
| 1261 | gctgcaggga cccagggcaa tgcctgccgg aaggacccaa ggttgggacg gtgtgtctgc |
| 1321 | aaacccaact tccggggtgc ccactgtgag ctctgtgctc ctggattcca cgggcctagc |
| 1381 | tgccacccat gccagtgttc cagccctggg gtagccaaca gcctctgtga cccagagtct |
| 1441 | ggccagtgca tgtgccgcac cggctttgag ggggacaggt gtgaccactg tgcccttggc |
| 1501 | tatttccact tccctctctg tcagctgtgt ggctgcagcc cagcagggac cctgcctgaa |
| 1561 | ggctgtgacg aggctggccg ctgccagtgc cgacctggct tgacggtcc tcactgtgac |
| 1621 | cgatgccttc caggatacca tgggtatccc gactgtcacg cttgtgcctg tgaccctcgg |
| 1681 | ggggccctgg atcaacagtg tggagtgggc ggtttgtgcc actgccgtcc tggcaacaca |
| 1741 | ggtgccactt gtcaggaatg tagccccggc ttctacggct tccccagctg catccccctgc |
| 1801 | cactgctctg ccgatggctc cttgcataca acctgtgacc cgacaaccgg ccagtgtagg |
| 1861 | tgtcgacccc gagtgacagg actacattgt gatatgtgtg taccaggcgc ctataacttc |
| 1921 | ccctactgtg aagctggctc ttgtcatcct gctggtctgg ccccagccaa tcctgcccct |
| 1981 | cctgagacac aggctccctg tatgtgccgg gctcacgtgg aagggccaag ctgtgatcgc |
| 2041 | tgtaaacctg ggtactgggg gctgagcgcc agcaaccctg aaggctgcac acgctgcagc |
| 2101 | tgtgacccac gaggcacccct gggtggagtt actgagtgcc agggcaatgg gcagtgcttc |
| 2161 | tgcaaggctc acgtgtgtgg caagacctgt gcagcctgca aggatggctt ctttggcctg |
| 2221 | gattatgctg actactttgg ctgccgtagc tgtaggtgtg atgttggtgg tgccctgggt |
| 2281 | cagggctgtg aaccaaagac aggtgcctgc aggtgccgcc ctaacaccca aggacccacc |
| 2341 | tgtagcgagc cagcgaagga ccactacttg ccagacctgc accacatgcg gctggaacta |
| 2401 | gaggaggcgg ccactcccga gggccacgct gtacgctttg gcttcaaccc cctggagttt |
| 2461 | gagaactttta gctggagagg ctacgcacac atgatggcta tccagcccag gattgtggcc |
| 2521 | aggctgaacg tgacctcccc tgacctcttt cgactggttt tccgatatgt caaccgtgga |
| 2581 | tcaaccagcg tgaatgggca gatctctgtt cgtgaagagg gcaagctttc cagctgtacc |
| 2641 | aactgcacag agcagagcca gccagtggct ttcccaccca gcactgagcc tgcctttgtc |
| 2701 | actgtgcccc agaggggctt tggggaaccc tttgtgctga accccggcat ctgggccttg |
| 2761 | ctggtcgagg ctgaaggtgt actcttggac tacgtggtcc tactgcccag cacctactat |
| 2821 | gaggcagctc tcctacagca tcgagtaacg gaggcctgta cctaccgtcc ctcagccctg |
| 2881 | cactccacag agaactgtct tgtctatgct cacctacccc tggatggctt cccttcagca |
| 2941 | gctggaactg aggccctgtg tcgccatgac aacagcctgc cccggccctg ccccacagag |
| 3001 | cagctcagcc cctcacaccc accgctggcg acctgcttcg gcagtgatgt ggacatccag |
| 3061 | ctcgagatgg ccgtgcctca gcctggccaa tatgttctcg tggtggaata tgtcggtgag |
| 3121 | gattcacacc aagagatggg agtggctgtg cacacccctc agagagcccc ccagcaaggg |
| 3181 | gtgctcaacc tccacccctg cccatacagc tccctgtgcc ggagtccggc tcgggacacc |
| 3241 | cagcatcatc tagccatctt ccacctggac tctgaggcta gcatccggct cacagctgag |
| 3301 | caagctcact tcttcctgca cagcgtcacc ctggtacctg tggaggagtt cagtactgag |
| 3361 | tttgtggagc cccgggtctt ctgtgtgagc agtcatggaa ctttcaaccc cagcagtgct |
| 3421 | gcctgtctag cctcccgatt cccgaagcca ccgcagccca tcatccttaa ggactgccag |
| 3481 | gtcttgccgc tgcctcccga cctgcctctg actcagtctc aggagctctc accaggtgca |
| 3541 | cccccccgagg gaccacagcc tcggccgcca actgcggtgg atcctaatgc agaacccacc |
| 3601 | ttgctgcgcc accccaggg cacggtggtc ttcaccaccc aggtgcccac cctgggccgc |
| 3661 | tatgccttcc tgctgcacgg ctaccagccg gtccaccccct ccttccctgt ggaggtactc |
| 3721 | attaatggtg gccgcatctg gcagggccac gccaacgcca gcttttgtcc tcatggttat |
| 3781 | ggctgccgta cccctggtgtt gtgtgagggt cagacgatgc tgatgttac agacaacgag |
| 3841 | ctcaccgtga ctgtgcgtgt gccagaaggc cggtggctct ggctggacta cgtactcatt |
| 3901 | gtccctgagg atgcttacag ctccagttac ctccaagagga gcctttgga caaatcctat |

FIG. 1C

| | |
|---|---|
| 3961 | gacttcatca gccactgtgc cacccagggc taccacatta gccccagcag ctcatctcca |
| 4021 | ttctgccgga atgccgccac ctccttgtct ctcttctaca acaacggggc cctcccttgt |
| 4081 | ggctgccacg aggtgggtgc cgtaagcccc acgtgcgaac ccttcggggg ccagtgtccc |
| 4141 | tgccggggcc acgttattgg ccgtgactgt tcccgctgtg ccaccggcta ctggggtttc |
| 4201 | cccaactgca ggccctgtga ctgtggagcc cgcctgtgtg acgagctcac gggccagtgt |
| 4261 | atctgtccac cacgcactgt tccccctgac tgcttggtct gccagccaca gagctttggt |
| 4321 | tgccacccct tggtgggctg tgaggagtgt aactgctcag ggcccggcgt ccaggagctg |
| 4381 | acggaccccta cctgtgacat ggacagcggc cagtgcagat gcagacccaa tgtagctgga |
| 4441 | cgtcgctgtg atacctgtgc cccgggcttc tatggctatc ctagctgtcg ccctgtgac |
| 4501 | tgccatgagg caggcaccat ggctagcgtg tgtgaccccc tcacaggcca atgccattgc |
| 4561 | aaggagaacg tgcagggctc aagatgtgac cagtgtcgcg tggggacctt ctccttggat |
| 4621 | gctgctaacc ccaagggctg tacccgctgc ttctgtttcg gggccacaga gcgctgtggg |
| 4681 | aactctaacc tcgcccgcca tgagttcgtg gacatggagg gctgggtgct gttgagcagt |
| 4741 | gaccggcagg tggtaccccca cgagcatcgg cctgagatag agctgctgca cgcagatctg |
| 4801 | cgctctgtgg ctgacacttt tcagagctg tactggcagg ctccgccctc ctatctggga |
| 4861 | gacagggtgt catcctacgt tggaaccctc cactatgagc tgcactcaga gacccagcga |
| 4921 | ggtgatatct tcattcccta cgagagccgg ccggacgtcg tgctgcaggg caaccaaatg |
| 4981 | agcatcgcct tcctggaact ggcgtaccct ccgcctggcc aggttcaccg aggacagcta |
| 5041 | cagctggtag aggggaactt ccggcacttg gagactcaca accccgtgtc ccgagaagaa |
| 5101 | ctcatgatgg tgctggccgg cctggagcag ctgcagatcc gtgctctctt ctcgcagacc |
| 5161 | tcttccagtg tctccttgcg tagagtggta ctggaggtgg ctagcgaggc tggtaggggg |
| 5221 | cctccagcca gcaatgtgga actgtgtatg tgccctgcca actaccgtgg ggactcgtgc |
| 5281 | caggaatgtg cccctggcta ttaccgggac accaagggtc tcttcctagg ccgatgtgtc |
| 5341 | ccctgtcagt gccatggcca ttcagatcgc tgccttcctg gctctggcat ttgtgtgggc |
| 5401 | tgccagcaca acacagaagg ggaccaatgt gagcgctgta ggcctggctt tgtcagcagt |
| 5461 | gatcccagta accctgcatc cccatgtgtg agctgcccct tgccccttggc agtgccctcc |
| 5521 | aataattttg cagacggttg cgtcttaaga aatggccgaa cccagtgcct ctgcaggcca |
| 5581 | ggctatgctg gtgcctcctg cgagcggtgt gcacctggct tttttgggaa cccctggtg |
| 5641 | ctaggcagct cctgtcagcc ctgcgactgc agcggtaatg gagaccccaa catgatcttc |
| 5701 | agtgactgcg acccctgac gggtgcctgt cgaggctgcc tccgtcacac cactgggccc |
| 5761 | cactgtgaac gctgtgcccc aggcttctat ggcaatgctt gttgccagg caactgcacc |
| 5821 | cggtgtgact gttccccatg tgggacagaa acctgtgatc ccagagtgg acgctgcctg |
| 5881 | tgcaaagcag gcgtgactgg acaacgttgt gaccgctgtt tggaaggata cttcggtttt |
| 5941 | gagcaatgcc agggctgccg cccttgtgcc tgtggaccag ctgccaaggg ctccgagtgc |
| 6001 | caccctcaga gcggtcagtg tcactgccag ccaggggacca caggacccca gtgcctcgag |
| 6061 | tgcgcccctg gctactgggg cctcccagag aagggctgca ggcgctgcca gtgtccccga |
| 6121 | ggccactgtg acccacacac gggccactgc acctgtcccc cggggctcag cggggaacgc |
| 6181 | tgtgacacct gcagccagca gcaccaggtg cctgtaccgg gcaagcctgg gggccatggc |
| 6241 | atacactgtg aagtgtgtga ccactgtgtg gttctccttc tggatgacct cgagcgggct |
| 6301 | ggtgccctcc tccccgctat ccgtgagcag ctgcagggta tcaatgccag ctccgcggcc |
| 6361 | tgggccaggc tgcacaggct gaatgcctcc attgctgacc tgcagagtaa actccggagg |
| 6421 | ccaccgggac cccgctacca ggcagcacag cagctacaga ctctagagca gcagagtata |
| 6481 | agccttcaac aggacacgga gaggctgggc agtcaggcca caggggtcca aggtcaggca |
| 6541 | ggccagctac tggacaccac agagtccaca ctgggccggg cacagaaagtt gttggagtct |
| 6601 | gtgcgagctg tgggccgtgc cctgaatgag ctggcatctc gcatgggcca aggatctcca |
| 6661 | ggcgatgcct tggtaccgtc tggcgagcag ctgcgctggg ctctggctga agtggagcgg |

FIG. 1D

| | |
|---:|:---|
| 6721 | ctgctctggg atatgcggac gcgtgacctg ggggcccagg gggcagtggc agaggccgaa |
| 6781 | ctggccgaag cccagaggct gatggctcgt gtccaggagc agctgaccag cttctgggag |
| 6841 | gagaaccagt cattggccac acacattcgg gaccagctgg ctcagtatga gtctggcctc |
| 6901 | atggatcttc gtgaggccct gaaccaggcc gttaatacca cccgggaggc tgaggaactc |
| 6961 | aacagccgca accaggaacg ggtgaaggaa gccctgcaat ggaaacagga actgtcccag |
| 7021 | gacaatgcca ccctgaaggc cactcttcaa gctgccagtc tcatcttggg ccatgtttct |
| 7081 | gagcttctgc agggcataga ccaggctaag gaggacctag agcacctggc ggccagcctg |
| 7141 | gatggagcct ggacaccctt actgaagagg atgcaggcct tttcccctgc cagcagcaag |
| 7201 | gtggacttgg tagaggctgc tgaggcccac gctcagaagc tgaaccagct ggcaatcaac |
| 7261 | ctgtctggca tcatccttgg catcaatcag gaccgcttca tccagagggc tgtggaagcc |
| 7321 | tccaatgcct acagcagcat ccttcaggcc gttcaggctg ccgaggatgc ggcaggccag |
| 7381 | gcactgaggc aggccagccg cacatgggag atggtggtgc agcggggcct agcagctgga |
| 7441 | gcccggcagc tgttagccaa cagcagtgcc ctggaggaga ccatccttgg acaccagggg |
| 7501 | aggctgggcc ttgctcaggg ccgtctgcag gctgcgggga tccagcttca taatgtctgg |
| 7561 | gccaggaaga accagctagc agcccagatc caggaggcac aagccatgct ggccatggac |
| 7621 | acgagcgaga ccagtgagaa gattgctcac gccaaggctg tggctgccga agccctcagt |
| 7681 | acggccaccc acgtgcagtc tcagcttcag ggtatgcaga agaatgtgga gaggtggcag |
| 7741 | agccagctgg gaggcctgca aggccaggac ctgagccagg tggaacggga tgcaagcagt |
| 7801 | tcagtgtcca ccctggagaa gacattgcca cagctgctgg ccaaactgag ccgtctagag |
| 7861 | aaccgtggag ttcacaatgc cagcctggct ttgtctgcca acattggtcg tgtgcgcaag |
| 7921 | ctcattgccc aagcccggag tgccgccagc aaggtcaagg tgtccatgaa gttcaatggg |
| 7981 | cgttcagggg tacgactgcg tcccccacga gaccttgccg accttgctgc gtacactgcc |
| 8041 | ctcaagttcc acatccagag cccagtgcca gcgcccgaac ctggcaagaa cacggggggac |
| 8101 | cactttgttc tgtacatggg cagccgccag gccactgggg actacatggg agtgtctctg |
| 8161 | cgtaatcaga aggtgcactg ggtgtacagg ctaggaaagg ctggccccac aactctcagc |
| 8221 | atcgacgaga acatcgggga gcagtttgca gccgtcagca tcgacaggac cctccagttt |
| 8281 | ggccacatgt ctgtcaccgt ggagaaacag atggttcatg agatcaaggg agacacggtg |
| 8341 | gcccctggga gcgagggact actcaacctg catcctgacg attttgtctt ctacgtggga |
| 8401 | ggatacccca gcaacttcac gcccccctgaa cccctccgat tcctggcta cctgggctgc |
| 8461 | attgagatgg aaacactgaa tgaggaggtg gtcagcctct acaatttga gcagaccttc |
| 8521 | atgctggaca cggcagtaga taaaccttgt gctcgctcca aggccaccgg tgacccatgg |
| 8581 | ctcacagatg gctcctacct ggatggcagt ggctttgccc gcatcagctt tgagaagcag |
| 8641 | ttcagcaaca caaaacgctt tgaccaggag ctgcggcttg tgtcctacaa tgggatcatc |
| 8701 | ttttttcctca agcaagagag ccagttcttg tgcctggcag tgcaggaagg caccctggtg |
| 8761 | ctcttctatg acttcggctc tggcctgaag aaggccgacc cactgcagcc ccacaagcc |
| 8821 | ttgacggcag ccagcaaggc gatccaagtg tttctattgg ctggcaatcg caaacgtgtg |
| 8881 | ttggtgcgtg tggagcgggc cactgtgttc agcgtagacc aggataacat gctggagatg |
| 8941 | gctgatgcct actactcggg aggdgtgcca cctgaacagc tgcccttgag cctacggcag |
| 9001 | ctcttcccct ccggaggctc tgtccgtggy tgcatcaagg gtattaaggc tctgggcaag |
| 9061 | tacgtggacc tcaaacggtt gaacaccacg ggcatcagtt tcggctgcac cgctgacctg |
| 9121 | ctagtgggac gcaccatgac ttttcacggc cacggcttcc tgccctggc acttcctgat |
| 9181 | gtggcaccca tcaccgaagt ggtctattct ggctttggct ttcgtggcac ccaggacaac |
| 9241 | aacctgctgt attaccgtac ctcccccggat gggccgtacc aggtatccct gagggagggc |
| 9301 | cacgtgacac tccgttttat gaaccaagag gtggaaactc aaagggtctt tgctgatggt |
| 9361 | gctcctcact atgttgcctt ctatagcaat gtcacagggg tatggctgta tgtggatgac |
| 9421 | cagctacaac tagtaaagtc tcatgagaga acaactccca tgctccaact acagcccgag |

FIG. 1E

| | |
|---|---|
| 9481 | gaaccctcac ggcttctcct gggaggcctg cctgtgtctg gtaccttcca caacttcagt |
| 9541 | ggctgcatca gcaatgtttt tgtacagcga cttcggggac cacagcgtgt gtttgaccta |
| 9601 | caccagaaca tggggagtgt caatgtaagc gtaggctgta caccagccca actcatcgag |
| 9661 | acctcaaggg ccacggctca gaaggtttcc cgccgtagtc gacaacccag ccaggacctt |
| 9721 | gcctgcacga caccctggct ccctgggact attcaggatg cataccagtt tgggggaccc |
| 9781 | ctgcccagtt acctacagtt tgtgggtatc tctccgtccc acaggaatag gctccacctc |
| 9841 | tccatgcttg tccgtccaca tgcggcttcc cagggcctcc tgctctctac agcccccatg |
| 9901 | tcgggccgca gcccttcgtt ggtactcttt ctaaaccatg gacactttgt cgcacagact |
| 9961 | gagggccctg gccccggct ccaggtccag agtcgccagc actcacgggc tggccagtgg |
| 10021 | cacagggtgt ccgtccgctg gggaatgcag cagatccagc ttgtggtgga cggcagccag |
| 10081 | acctggagcc agaaggctct ccaccatcgg gtccccaggg cagagcgacc acagccctac |
| 10141 | accctctctg taggaggtct tcctgccagc agttacagtt ccaagctccc tgtgtctgtg |
| 10201 | gggttcagcg gctgtctgaa gaaattacag ctggataagc agccactgag gaccccaacg |
| 10261 | caaatggtgg gggtcacacc ctgtgtctca ggcccctgg aagatggcct gttcttccca |
| 10321 | ggcagtgagg gagttgtcac attagagctc cccaaggcca agatgcccta tgtgagcctg |
| 10381 | gagctagaga tgcggccctt ggcagctgct ggcctcatct tccacctggg ccaggccctg |
| 10441 | gccactccct acatgcagct gaaggtgctg acagaacagg tcctgctgca ggcaaatgat |
| 10501 | ggggcagggg agttttccac gtgggtgacc tacccaagc tttgtgatgg acggtggcac |
| 10561 | cgagtggcag tgatcatggg cagggacaca ctccggctgg aggtagacac acagagcaac |
| 10621 | cacaccacag gccgtttgcc agagagcttg gctggttctc cagcacttct gcacctcggg |
| 10681 | agcctgccca gtcttcaac tgctcggcca gagctccctg cctaccgagg atgcttgagg |
| 10741 | aagctgctga tcaatggggc ccctgtcaac gtgactgctt ctgtacaaat ccagggggca |
| 10801 | gtggggatgc gcggatgccc ctcaggaacc ctagcacttt ccaagcaggg aaaggcactg |
| 10861 | acccagaggc acgccaagcc cagtgtctcc ccgctacttt ggcattgagg gttcccagac |
| 10921 | cttggggttt gcctacactt tctatgaata acaagtcatt tctggtttac actgtctttt |
| 10981 | agaggaaaag gactctgtag aacagatat |

FIG. 1F

Amino Acid Sequence and Nucleotide Sequence Encoding Human Alpha5 Chain

SGVQLRTPRDLADLAAYTALKFYLQGPEPEPGQGTEDRFVMYMGSRQATGDYM
GVSLRDKKVHWVYQLGEAGPAVLSIDEDIGEQFAAVSLDRTLQFGHMSVTVER
QMIQETKGDTVAPGAEGLLNLRPDDFVFYVGGYPSTFTPPPLLRFPGYRGCIEMD
TLNEEVVSLYNFERTFQLDTAVDRPCARSKSTGDPWLTDGSYLDGTGFARISFDS
QISTTKRFEQELRLVSYSGVLFFLKQQSQFLCLAVQEGSLVLLYDFGAGLKKAVP
LQPPPPLTSASKAIQVFLLGGSRKRVLVRVERATVYSVEQDNDLELADAYYLGG
VPPDQLPPSLRWLFPTGGSVRGCVKGIKALGKYVDLKRLNTTGVSAGCTADLLV
GRAMTFHGHGFLRLALSNVAPLTGNVYSGFGFHSAQDSALLYYRASPDGLCQVS
LQQGRVSLQLLRTEVKTQAGFADGAPHYVAFYSNATGVWLYVDDQLQQMKPH
RGPPPELQPQPEGPPRLLLGGLPESGTIYNFSGCISNVFVQRLLGPQRVFDLQQNL
GSVNVSTGCAPALQAQTPGLGPRGLQATARKASRRSRQPARHPACMLPPHLRTT
RDSYQFGGSLSSHLEFVGILARHRNWPSLSMHVLPRSSRGLLLFTARLRPGSPSLA
LFLSNGHFVAQMEGLGTRLRAQSRQRSRPGRWHKVSVRWEKNRILLVTDGARA
WSQEGPHRQHQGAEHPQPHTLFVGGLPASSHSSKLPVTVGFSGCVKRLRLHGRP
LGAPTRMAGVTPCILGPLEAGLFFPGSGGVITLDLPGATLPDVGLELEVRPLAVT
GLIFHLGQARTPPYLQLQVTEKQVLLRADDGAGEFSTSVTRPSVLCDGQWHRLA
VMKSGNVLRLEVDAQSNHTVGPLLAAAAGAPAPLYLGGLPEPMAVQPWPPAYC
GCMRRLAVNRSPVAMTRSVEVHGAVGASGCPAA

```
1      tcaggggtgc agctgcgcac cccacgggat cttgccgacc ttgctgccta cactgccctc
61     aagttctacc tgcagggccc agagcctgag cctgggcagg gtaccgagga tcgctttgtg
121    atgtacatgg gcagccgcca ggccactggg gactacatgg gtgtgtctct gcgtgacaag
181    aaggtgcact gggtgtatca gctgggtgag gcgggccctg cagtcctaag catcgatgag
241    gacattgggg agcagttcgc agctgtcagc ctggacagga ctctccagtt tggccacatg
301    tccgtcacag tggagagaca gatgatccag gaaaccaagg gtgacacggt ggcccctggg
361    gcagaggggc tgctcaacct gcggccagac gacttcgtct tctacgtcgg ggggtacccc
421    agtaccttca cgccccctcc cctgcttcgc ttccccggct accggggctg catcgagatg
481    gacacgctga tgaggaggt ggtcagcctc tacaacttcg agaggaccttc cagctggac
541    acggctgtgg acaggccttg tgcccgctcc aagtcgaccg ggacccgtg gctcacggac
601    ggctcctacc tggacggcac cggcttcgcc cgcatcagct tcgacagtca gatcagcacc
661    accaagcgct tcgagcagga gctgcggctc gtgtcctaca gcggggtgct cttcttcctg
721    aagcagcaga gccagttcct gtgcttggcc gtgcaagaag gcagcctcgt gctgttgtat
781    gactttgggg ctggcctgaa aaaggccgtc ccactgcagc cccaccgcc cctgacctcg
841    gccagcaagg cgatccaggt gttcctgctg gggggcagcc gcaagcgtgt gctggtgcgt
901    gtggagcggg ccacggtgta cagcgtggag caggacaatg atctggagct ggccgacgcc
961    tactacctgg ggggcgtgcc gcccgaccag ctgccccga gcctgcgatg gctcttcccc
1021   accggaggct cagtccgtgg ctgcgtcaaa ggcatcaagg ccctgggcaa gtatgtggac
1081   ctcaagcggc tgaacacgac aggcgtgagc gccggctgca ccgccgacct gctggtgggg
1141   cgcgccatga ctttccatgg ccacggcttc ttcgcctgg cgctctcgaa cgtggcaccg
1201   ctcactggca acgtctactc cggcttcggc ttccacagcg cccaggacag tgccctgctc
1261   tactaccggg cgtccccgga tgggctatgc caggtgtccc tgcagcaggg ccgtgtgagc
1321   ctacagctcc tgaggactga agtgaaaact caagcgggct cgccgatgg tgccccccat
1381   tacgtcgcct tctacagcaa tgccacggga gtctggctgt atgtcgatga ccagctccag
1441   cagatgaagc ccaccgggg accaccccc gagctccagc cgcagcctga ggggccccg
```

FIG. 2A

| | |
|---|---|
| 1501 | aggctcctcc tgggaggcct gcctgagtct ggcaccattt acaacttcag tggctgcatc |
| 1561 | agcaacgtct tcgtgcagcg gctcctgggc ccacagcgcg tatttgatct gcagcagaac |
| 1621 | ctgggcagcg tcaatgtgag cacgggctgt gcacccgccc tgcaagccca gaccccgggc |
| 1681 | ctggggccta gaggactgca ggccaccgcc cggaaggcct cccgccgcag ccgtcagccc |
| 1741 | gcccggcatc ctgcctgcat gctgccccca cacctcagga ccacccgaga ctcctaccag |
| 1801 | tttgggggtt ccctgtccag tcacctggag tttgtgggca tcctggcccg acataggaac |
| 1861 | tggcccagtc tctccatgca cgtcctcccg cgaagctccc gaggcctcct cctcttcact |
| 1921 | gcccgtctga ggcccggcag cccctccctg gcgctcttcc tgagcaatgg ccacttcgtt |
| 1981 | gcacagatgg aaggcctcgg gactcggctc cgcgcccaga gccgccagcg ctcccggcct |
| 2041 | ggccgctggc acaaggtctc cgtgcgctgg gagaagaacc ggatcctgct ggtgacggac |
| 2101 | ggggcccggg cctggagcca ggaggggccg caccggcagc accaggggc agagcacccc |
| 2161 | cagccccaca ccctctttgt gggcggcctc ccggccagca gccacagctc caaacttccg |
| 2221 | gtgaccgtcg ggttcagcgg ctgtgtgaag agactgaggc tgcacgggag gcccctgggg |
| 2281 | gcccccacac ggatggcagg ggtcacaccc tgcatcttgg gccccctgga ggcgggcctg |
| 2341 | ttcttcccag gcagcggggg agttatcact ttagacctcc caggagctac actgcctgat |
| 2401 | gtgggcctgg aactggaggt gcggcccctg gcagtcaccg gactgatctt ccacttgggc |
| 2461 | caggcccgga cgccccccta cttgcagttg caggtgaccg agaagcaagt cctgctgcgg |
| 2521 | gcggatgacg gagcagggga gttctccacg tcagtgaccc gcccctcagt gctgtgtgat |
| 2581 | ggccagtggc accggctagc ggtgatgaaa agcgggaatg tgctccggct ggaggtggac |
| 2641 | gcgcagagca accacaccgt gggccccttg ctggcggctg cagctggtgc cccagcccct |
| 2701 | ctgtacctcg ggggcctgcc tgagcccatg gccgtgcagc cctggccccc cgcctactgc |
| 2761 | ggctgcatga ggaggctggc ggtgaaccgg tcccccgtcg ccatgactcg ctctgtggag |
| 2821 | gtccacgggg cagtgggggc cagtggctgc ccagccgcct aggacacagc caaccccggc |
| 2881 | ccctggtcag gcccctgcag ctgcctcaca ccgcccttg tgctcgcctc ataggtgtct |
| 2941 | atttggactc taagctctac gggtgacaga tcttgtttct gaagatggtt taagttatag |
| 3001 | cttcttaaac gaaagaataa aatactgcaa aatgttttta tatttggccc ttccacccat |
| 3061 | ttttaattgt gagagatttg tcaccaatca tcactggttc ctccttaaaa attaaaaagt |
| 3121 | aacttctgtg taaaaaaaaa a |

FIG. 2B

Amino Acid Sequence and Nucleotide Sequence Encoding Murine Beta2 Chain

MEWASGEPGRGRQGQPLPWELRLGLLLSVLAATLAQAPSLDVPGCSRGS
CYPATGDLLVGRADRLTASSTCGLHSPQPYCIVSHLQDEKKCFLCDSRRP
FSARDNPNSHRIQNVVTSFAPQRRTAWWQSENGVPMVTIQLDLEAEFHFT
HLIMTFKTFRPAAMLVERSADFGRTWHVYRYFSYDCGADFPGIPLAPPRR
WDDVVCESRYSEIEPSTEGEVIYRVLDPAIPIPDPYSSRIQNLLKITNLRVNL
TRLHTLGDNLLDPRREIREKYYYALYELVIRGNCFCYGHASQCAPAPGAP
AHAEGMVHGACICKHNTRGLNCEQCQDFYQDLPWHPAEDGHTHACRKC
ECNGHTHSCHFDMAVYLASGNVSGGVCDGCQHNTAGRHCEFCRPFFYR
DPTKDMRDPAVCRPCDCDPMGSQDGGRCDSHDDPVLGLVSGQCRCKEH
VVGTRCQQCRDGFFGLSASDPRGCQRCQCNSRGTVPGSSPCDSSSGTCFC
KRLVTGHGCDRCLPGHWGLSHDLLGCRPCDCDVGGALDPQCDEATGQC
PCRQHMIGRRCEQVQPGYFRPFLDHLTWEAEAAQGQVLEVVERLVTNRE
TPSWTGPGFVRLREGQEVEFLVTSLPRAMDYDLLLRWEPQVPEQWAELE
LMVQRPGPVSAHSPCGHVLPKDDRIQGMLHPNTRVLVFPRPVCLEPGISY
KLKLKLIGTGGRAQPETSYSGLLIDSLVLQPHVLVLEMFSGGDAAALERR
TTFERYRCHEEGLMPSKAPLSETCAPLLISVSALIYNGALPCQCDPQGSLSS
ECSPHGGQCRCKPGVVGRRCDVCATGYYGFGPAGCQACQCSPDGALSA
LCEGTSGQCPCRPGAFGLRCDHCQRGQWGFPNCRPCVCNGRADECDTHT
GACLGCRDYTGGEHCERCIAGFHGDPRLPYGGQCRPCPCPEGPGSQRHFA
TSCHRDGYSQQIVCHCRAGYTGLRCEACAPGPFGDPSKPGGRCQLCECSG
NIDPMDPDACDPHTGQCLRCLHNTEGPHCGYCKPGFHGQAARQSCHRCT
CNLLGTDPRRCPSTDLCHCDPSTGQCPCLPHVQGLNCDHCAPNFWNFTSG
RGCQPCACHPSRARGPTCNEFTGQCHCHAGFGGRTCSECQELYWGDPGL
QCRACDCDPRGIDKPQCHRSTGHCSCRPGVSGVRCDQCARGFSGVFPAC
HPCHACFGDWDRVVQDLAARTRRLEQWAQELQQTGVLGAFESSFLNMQ
GKLGMVQAIMSARNASAASTAKLVEATEGLRHEIGKTTERLTQLEAELTA
VQDENFNANHALSGLERDGFALNLTLRQLDQHLEILKHSNFLGAYDSIRH
AHSQSTEAERRANASTFAVPSPVSNSADTRRRTEVLMGAQKENFNRQHL
ANQQALGRLSAHAHTLSLTGINELVCGAPGDAPCATSPCGGAGCRDEDG
QPRCGGLGCSGAAAPADLALGRARHSQAELQRALVEGGGILSRVSETRR
QAEAAQQRAQAALDKANASRGQVEQANQELRELIQNVKDFLSQEGADP
DSIEMVATRVLDISIPASPEQIQRLASEIAERVRSLADVDTILAHTMGDVRR
AEQLLQDAHRARSRAEGERQKAETVQAALEEAQRAQGAAQGAIRGAVV
DTQNTEQTLQRVQERMAGAEKSLNSAGERARQLDALLEALKLKRAGNSL
AASTAEETAGSAQSRAREAEKQLREQVGDQYQTVRALAERKAEGVLAA
QARAEQLRDEARDLLQAAQDKLQRLQELEGTYEENERALEGKAAQLDG
LEARMRSVLQAINLQVQIYNTCQ

```
  1 aaagggcctc gagcttccaa gtaatctttg cttgatctcc aagagtctgt catagcgtgg
 61 cactcaaacg aagccgtacg acctgaacca acctcttccg cctgttgtcc aggggtctgg
121 gtggnnngcg cctagtgggt gcgcgcattc caaccctcgc tcccggcctg ccaggcgact
181 ggaaagtccg gcgtggataa atagtcacaa gattcggatt cacttgttgc tggtggtcca
241 gagtctgtca cccagaaccc atcctctggg taactgagta gccacagccc attttaatca
```

FIG. 3A

```
 301 ggaaacaggc aacctttctc gcaacccatt tgctggagtg cttatggacg gtcgagttcc
 361 tcggagttct gtttcaggca gtagtgcgtg gcctttccag tatctccgag agctcagtcc
 421 tagtctatcc tttgggcgtc ctaaaccttt ccacaggtac aatagaattc tagcttgcac
 481 ctttcccatc catctcccga ctgatgctgt aaccctggga gccccgcggc tgatttgtgg
 541 tttccatagt gacaccagga caaaggccat aagctccttc catctgcctt cctgatacac
 601 aaagatcaca aacctctcga tttacctctg ccacccgcca actccacgag ccctcttcct
 661 gtccctgaa tgccatgctt gccagcaacc cctggttcac atcgggactt aagggatccg
 721 atgaagatat gtggaccagg atgctctgtc tttgagcagc ctactctaat ttcttttggg
 781 atgctcccttt ttagttcctc gaactaagct gcttctttgc taagtacaca tctgctaaat
 841 aaacttcagc ttaaaaagaa agtggatgaa gtaaccaaag tctggttctt aggatgaggg
 901 ttgtctgcag cgggcagggg tatggtaggg grtggggtgc tatcctcagt tataatccta
 961 ttttagatcc actccgtgtt ttacttcctt cccttgcttt ccaactttac tcaaagtcgt
1021 cagagtctct cagattgtgg aggagtgact gctaggtccg accctggaca gattgagggc
1081 ctggagggac accagcccag tacccacacg gtcgggtcag catcagcccc aagggaggtg
1141 gtgggctttc gtctgtggac tctttatctc tctttatctc tattttactt ttcttcagga
1201 tggagtgggc ctcaggagaa ccagggaggg gcaggcaggg acagcctttg ccatgggaac
1261 ttcgcttggg cctacttcta agtggtgagg gggcctggtg aggcctaagg ttgtgggatg
1321 tgatggtagg tccaggggtg gcaggctgtt cccaggggcc caagggggtgg ggctagtcac
1381 caggagtcct gctgagctga ttgacccact gtcctcagtg ctggctgcca cattggccca
1441 ggccccgtcc ttggatgtac ctggctgttc tcgaggaagc tgctatccag ccaccggtga
1501 cctgttggtg ggccgtgcgg acagactgac ggcctcatcc acgtgtggct tgcatagccc
1561 tcaaccctac tgtattgtca gtcacctgca ggtgcttctg gggccccaga ggagagggct
1621 gggtcagggt ggggtcggcc ccagctaagg tacctatcct acactccacc caatccagga
1681 cgaaaagaag tgtttcctgt gtgactcccg acgtcccttc tctgctcgag acaacccaaa
1741 tagtcatcgg atccagaatg tagtcaccag ctttgcgcca caacgccgga cggcctggtg
1801 gcaatcggag aacggtgagc ccctgagtag gtcatcagga tgactagggc ttgtaaccag
1861 taaccgcaga accttgaccc cctattcctg ctgcagggt tccaatggtc accatccaac
1921 tggacctgga agctgagttt catttcaccc acctcattat gacgttcaag gtgcctgtgc
1981 gtcagcgaac ccgcctgatt ttgctttgct tctcagtacc ccctaacaga gtcctagctc
2041 tacaacgaag cttccctgag ctcctgtgtt gtgctctatg tgtgaagcat ggtcacgtcc
2101 tgcatggctt ccatagttga acacctctgc acatgctctc ttgtgcccca ttcctaggct
2161 aagtcagata cagtctctct gggtctcgtg gtattttaac ctgcctgtca gaggtggctg
2221 tcctccctgg tctgatcatg gtctggctt cctagtcttt cccatgtgtc tgagatgctc
2281 agcagtgatc atgactaagc agagctctcc gtaacctagg ctggactgaa gtctggttcc
2341 tgctagtcag acatgtcctc cttccccatc cagacgttcc ggcctgctgc tatgctggtg
2401 gagcgttctg cagactttgg ccgcacctgg cacgtgtacc gatatttttc ctatgactgc
2461 ggggctgact tcccgggaat cccactggcc ccgccacgtc gctgggatga tgtagtgtgt
2521 gagtcccgct actcagaaat cgagccgtct acggaaggcg aggtaagggc tgggacccag
2581 ctagtggggt ctgtgatgga cgtggacgag gttcattatc tgtggacttc ttgccctgct
2641 aggtcatcta tcgtgtgctg gaccctgcta ttcccatccc agacccctac agctcacgga
2701 ttcagagtga gtgttctact atggacattg gcacagtctc agtgtccgga tgggactatt
2761 tggggcctca gtaactattt taggtgcttc ctagggcaaa tgccaagccc agtttagctc
2821 tgggagcaat agaaaagagg tctcccaagg tgaccttggc agctgcaacc aatggtggca
2881 ctggtgggga cgaggcaaca aggggccacc tgcttagttg gacgagaccc tcttcccttt
2941 cttagacctg ttgaagatca ccaacctacg agtgaactta acccggcttc acacactggg
3001 agacaacttg cttgacccac ggagggagat ccgggaaaaa tactattatg ctctctatga
```

FIG. 3B

```
3061 acttgtcatc cgtggcaact gcttctgcta tggccacgcc tcacagtgtg cgcctgcacc
3121 aggggcgccg gcccatgctg agggcatggt aagggacttc ggatgactgg aacagggttg
3181 ccggggaggg acaggcattt ctagatggtc ccgtcaacct cccctcgtat ctgcacaggt
3241 acacggagcc tgtatctgca agcacaatac tcgtggactc aactgtgagc agtgtcagga
3301 tttctatcag gaccttccct ggcaccctgc agaggacggc catactcacg cctgtcggag
3361 tgagtgagac acagaactct aaccgggctg tgctctgggt gagccaaaaa gctagttggt
3421 caagccctaa atacctaggc ytttgtctga agggtatcag gccttgatgg cctcaaccca
3481 tgtgctctgc tacagtccaa agttggagct tgaagctaag ctgcaccaca aattctagct
3541 atggtaccat aggctgatga tactagcccc actcgcgtgt ccttacctag gacctggttt
3601 ccaattggtc tttgccttct ctccagagtg tgagtgcaac gggcatactc atagctgcca
3661 ctttgacatg gctgtctacc tggcatctgg aaatgtaagt ggaggcgtat gcgatgggtg
3721 tcagcacaac acagctgggc gccattgtga gttctgccgg cccttcttct accgtgaccc
3781 caccaaggac atgcgggacc cagctgtgtg ccgtcgtaag gctgggattg ggcatgaggc
3841 tgantctcag aactagaact aggaacgtgg attatatgac gttcccagga ttggtgtggt
3901 cagggcttgg ggtagaacca gaacagggaa agggaaggct caggatggtc actgcgatgg
3961 ggtgacttta tactctcctt tttctcagct tgtgactgtg accctatggg ttctcaagat
4021 ggtggtcgct gtgattctca tgatgaccct gtgctaggac tggtctcagg ccagtgtcgc
4081 tgcaaagaac acgtggttgg cactcgctgc cagcaatgcc gtgatggctt ctttggactt
4141 agtgccagtg accctcgagg gtgccagcgt atgtgcctcc tgccctaact cctgtgtcga
4201 cctttaaccc caggcctctt gttcttgatg cagttgaacc tgcttttact ccctaaaatg
4261 ggctgctttt cactacaggt tgccagtgta attcacgggg cacagtgcct gggagctccc
4321 cttgtgactc cagtagtgga acctgtttct gcaagcgtct ggtgaccgga catggctgtg
4381 accgctgtct ggtacgactg agggatctgg ggtcctggga tcctgggttt gttctcaaag
4441 cacatgggca aagtccagtg ggtggacact gagagcctag agtctagtcc tggaagacaa
4501 gcgtctggtc tggcaggtca agggtctaga ccagtggtct ggggctttgc attcaccagt
4561 ccaagtggta aattgctgac tacctggtgg gtggcaagga ggtctgttcc tggcttccag
4621 caattccttt tccctagcct ggccactggg gcctgagcca tgacctgctg ggctgccgtc
4681 cctgtgactg tgatgtgggc ggtgccttgg atcctcagtg agtattgtta caggtgcttg
4741 ggaggtggat gggaaggcga agcatgggtc ctttggtaac cacagcattc ctcaggtgtg
4801 atgaggccac cggtcagtgc ccgtgccgcc aacacatgat tgggcggcgc tgcgaacaag
4861 tgcagcctgg ctacttccgg ccttttctgg accatttaac ctgggaggct gaggctgccc
4921 aagggcagtg ggagcactca tatgatgtgg gtggtgtggt agagaggagg ggttgtgggt
4981 ggtgtcttgg ggggtctagg ttgctattca gtcttggggg aggtcttggc acaggacatg
5041 gtgtttgggg ctggctgtgg cagaagagac agtggttcac ctgacacctc atctctgctt
5101 tgactgcatt gactcagggt gcttgaggtg gtagagcggc tggtgaccaa ccgagagact
5161 ccgtcctgga ctggcccagg ctttgtgcgg ctgcgagaag gtcaggaagt ggagttcctg
5221 gtgacctctt tgcctagggc catggactat gacctgctac tgcgctggga gccccaggtt
5281 agaccctgtg gtggctgacc tgtgctgaca ttctgggtgt ggaagcaccc tctccactgt
5341 cctctctccc caggtccctg agcaatgggc agagctggaa ctgatggtgc agcgtccggg
5401 gcctgtgtct gctcacagtc cgtgcgggca tgtgctgcct aaggatgacc gcattcaggg
5461 gatgcttcac ccaaacacca ggtgaggcgg ngggtaagga ttgcccacag acctcctgaa
5521 agactgacat tgcgctgtgt tgttccttct ttaagtccct cctcctggct gctgttcgtc
5581 aggtccatgg ctgtgactca caggaaagac atagataaca catggcctgc ttcctcaagg
5641 gtataagttt cagaaggcaa gacattaatt ggtctgttac tccgaaacag ccttatgatg
5701 gtgacagttg cagtggcgta agatatgtaa ctggactagt taaggttttg ttacatttta
5761 gaagtaatta tttcctgtat cttttcctc actactctct gctcttctct tctcttctct
5821 tctcttctct tctcttctct actcttctct tctctactct actagtctaa acttatcttc
5881 tgctcttacc tctctctctc tctcaacctg agacagggtt tctctgtata gccccagggt
5941 gtcctggaac tcactac
```

FIG. 3C

Amino Acid Sequence and Nucleotide Sequence Encoding Human Beta2 Chain

MELTSTERGRGQPLPWELRLPLLLSVLAATLAQAPAPDVPGCSRGSCYPATADLL
VGRADRLTASSTCGLNGRQPYCIVSHLQDEKKCFLCDSRRPFSARDNPHTHRIQN
VVTSFAPQRRAAWWQSQNGIPAVTIQLDLEAEFHFTHLIMTFKTFRPAAMLVERS
ADFGRTWHVYRYFSYHCGADFPGVPLAPPRHWDDVVCESRYSEIEPSTEGEVIY
RVLDPAIPIPDPYSSRIQNLLKITNLRVNLTRLHTLGDNLLDPRREIREKYYYALYE
LVVRGNCFCYGHASECAPAPGAPAHAEGMVHGACICKHNTRGLNCEQCQDFYR
DLPWRPAEDGHSHACRKCDRHGHTHSCHFDMAVYLGSGNVSGGVCDGCQHNT
AWRHCELCRPFFYRDPTKDLRDPAVCRSCDCDPMGSQDGGRCDSHDDPALGLV
SGQCRCKEHVVGTRCQQCRDGFFGLSISDPSGCRRCQCNARGTVPGSTPCDPNS
GSCYCKRLVTGRGCDRCLPGHWGLSLDLLGCRPCDCDVGGALDPQCDEGTGQC
HCRQHMVGRRCEQVQPGYFRPFLDHLIWEAENTRGQVLDVVERLVTPGETPSW
TGSGFVRLQEGQTLEFLVASVPNAMDYDLLLRLEPQVPEQWAELELIVQRPGPV
PAHSLCGHLVPRDDRIQGTLQPHARYLIFPNPVCLEPGISYKLHLKLVRTGGSAQP
ETPYSGPGLLIDSLVLLPRVLVLEMFSGGDAAALERQATFERYQCHEEGLVPSKT
SPSEACAPLLISLSTLIYNGALPCQCNPQGSLSSECNPHGGQCLCKPGVVGRRCDT
CAPGYYGFGPTGCQACQCSPRGALSSLCERTSGQCLCRTGAFGLRCDACQRGQ
WGFPSCRPCVCNGHADECNTHTGACLGCRDLTGGEHCERCIAGFHGDPRLPYG
AQCRPCPCPEGPGSQRHFATSCHQDEYSQQIVCHCRAGYTGLRCEACAPGQFGD
PSRPGGRCQLCECSGNIDPMDPDACDPHPGQCLRCLHHTEGPHCAHSKPGFHGQ
AARQSCHRCTCNLLGTNPQQCPSPDQCHCDPSSGQCPCLPNVQALAVDRCAPNF
WNLTSGHGCQPCACLPSPEEGPTCNEFTGQCHCLCFGGRTCSECQELHWGDPG
LQCHACDCDSRGIDTPQCHRFTGHCTCRPGVSGVRCDQCARGFSGIFPACHPCH
ACFGDWDRVVQDLAARTQRLEQRAQELQQTGVLGAFESSFWHMQEKLGIVQGI
VGARNTSAASTAQLVEATEELRREIGEATEHLTQLEADLTDVQDENFNANHALS
GLERDRLALNLTLRQLDQHLDLLKHSNFLGAYDSIRHAHSQSAEAERRANTSAL
AVPSPVSNSASARHRTEALMDAQKEDFNSKHMANQRALGKLSAHTHTLSLTDIN
ELVCGAQGLHHDRTSPCGGAGCRDEDGQPRCGGLSCNGAAATADLALGRARHT
QAELQRALAEGGSILSRVAETRRQASEAQQRAQAALDKANASRGQVEQANQEL
QELIQSVKDFLNQEGADPDSIEMVATRVLELSIPASAEQIQHLAGAIAERVRSLAD
VDAILARTVGDVRRAEQLLQDARRARSWAEDEKQKAETVQAALEEAQRAQGIA
QGAIRGAVADTRDTEQTLYQVQERMAGAERALSSAGERARQLDALLEALKLKR
AGNSLAASTAEETAGSAQGRAQEAEQLLRGPLGDYQTVKALAERKAQGVLAA
QARAEQLPDEARDLLQAAQDKLQRLQELEGTYEENERALESKAAQLDGLEARM
RSVLQAINLQVQIYNTCQ

```
  1      ccgcccggtg ttgcgctcct tcccagaatc cgctccggcc tttccttcct gccgcgattc
 61      ccaactttgc tcaaagtcgc cggactctaa gctgtcggag ggaccgctgg acagacctgg
121      gaactgacag agggcctgga gggaaatagg ccaaagaccc acaggatgga gctgacctca
181      accgaaagag ggaggggaca gcctctgccc tgggaacttc gactgcccct actgctaagc
241      gtgctggctg ccacactggc acaggcccct gccccggatg tcctggctg ttccagggga
301      agctgctacc ccgccacggc cgacctgctg gtgggccgag ctgacagact gactgcctca
361      tccacttgtg gcctgaatgg ccgccagccc tactgcatcg tcagtcacct gcaggacgaa
421      aagaagtgct tcctttgtga ctcccggcgc cccttctctg ctagagacaa cccacacacc
```

FIG. 4A

```
 481  catcgcatcc agaatgtagt caccagcttt gcaccacagc ggcgggcagc ttggtggcag
 541  tcacagaatg gtatccctgc ggtcaccatc cagctggacc tggaggctga gtttcatttc
 601  acacacctca ttatgacctt caagacattt cgccctgctg ccatgctggt cgaacgctca
 661  gcagactttg gccgcacctg gcatgtgtac cgatatttct cctatcactg tggggctgac
 721  ttcccaggag tcccactagc accccacgg cactgggatg atgtagtctg tgagtcccgc
 781  tactcagaga ttgagccatc cactgaaggc gaggtcatct atcgtgtgct ggaccctgcc
 841  atccctatcc cagacccta cagctcacgg attcagaacc tgttgaagat caccaaccta
 901  cgggtgaacc tgactcgtct acacacgttg ggagacaacc tactcgaccc acggagggag
 961  atccgagaga agtactacta tgccctctat gagctggttg tacgtggcaa ctgcttctgc
1021  tacggacacg cctcagagtg tgcacccgcc ccaggggcac cagcccatgc tgagggcatg
1081  gtgcacggag cttgcatctg caaacacaac acacgtggcc tcaactgcga gcagtgtcag
1141  gatttctatc gtgacctgcc ctggcgtccg gctgaggacg gccatagtca tgcctgtagg
1201  aagtgtgatc ggcatgggca cacccacagc tgccacttcg acatggccgt atacctcgga
1261  tctggcaatg tgagtggagg tgtgtgtgat ggatgtcagc ataacacagc gtggcgccac
1321  tgtgagctct gtcggcccct cttctaccgt gacccaacca aggacctgcg ggatccggct
1381  gtgtgccgct cctgtgattg tgaccccatg ggttctcaag acggtggtcg ctgtgattcc
1441  catgatgacc ctgcactggg actggtctcc ggccagtgtc gctgcaaaga acacgtggtg
1501  ggcactcgct gccagcaatg ccgtgatggc ttctttgggc tcagcatcag tgacccgtct
1561  gggtgccggc gatgtcaatg taatgcacgg ggcacagtgc ctgggagcac tccttgtgac
1621  cccaacagtg gatcctgtta ctgcaaacgt ctagtgactg gacgtggatg tgaccgctgc
1681  ctgcctggcc actggggcct gagcctcgac ctgctcggct gccgcccctg tgactgcgac
1741  gtgggtggtg ctttggatcc ccagtgtgat gagggcacag gtcaatgcca ctgccgccag
1801  cacatggttg ggcgacgctg tgagcaggtg caacctggct acttccggcc cttcctggac
1861  cacctaattt gggaggctga gaacacccga gggcaggtgc tcgatgtggt ggagcgcctg
1921  gtgacccccg gggaaactcc atcctggact ggctcaggct tcgtgcgact acaggaaggt
1981  cagaccctgg agttcctggt ggcctctgtg ccgaacgcga tggactatga cctgctgctg
2041  cgcttagagc cccaggtccc tgagcaatgg gcagagttgg aactgattgt gcagcgtcca
2101  gggcctgtgc ctgcccacag cctgtgtggg catttggtgc cagggatga tcgcatccaa
2161  gggactctgc aaccacatgc caggtacttg atatttccta atcctgtctg ccttgagcct
2221  ggtatctcct acaagctgca tctgaagctg gtacggacag ggggaagtgc ccagcctgag
2281  actcccctact ctggacctgg cctgctcatt gactcgctgg tgctgctgcc ccgtgtcctg
2341  gtgctagaga tgtttagtgg gggtgatgct gctgccctgg agcgccaggc cacctttgaa
2401  cgctaccaat gccatgagga gggtctggtg cccagcaaga cttctcccctc tgaggcctgc
2461  gcacccctcc tcatcagcct gtccaccctc atctacaatg gtgccctgcc atgtcagtgc
2521  aaccctcaag gttcactgag ttctgagtgc aaccctcatg gtggtcagtg cctgtgcaag
2581  cctggagtgg ttgggcgccg ctgtgacacg tgtgccctg gctactatgg ctttggcccc
2641  acaggctgtc aagcctgcca gtgcagccca cgaggggcac tcagcagtct ctgtgaaagg
2701  accagtgggc aatgtctctg tcgaactggt gcctttgggc ttcgctgtga cgcctgccag
2761  cgtggccagt ggggattccc tagctgccgg ccatgtgtct gcaatgggca tgcagatgag
2821  tgcaacaccc acacaggcgc ttgcctgggc tgccgtgatc tcacaggggg tgagcactgt
2881  gaaaggtgca ttgctggttt ccacgggga ccacggctgc catatggggc gcagtgccgg
2941  ccctgtccct gtcctgaagg ccctgggagc caacggcact tgctactct ttgccaccag
3001  gatgaatatt cccagcagat tgtgtgccac tgccgggcag gctatacggg gctgcgatgt
3061  gaagcttgtg ccctgggca gtttggggac ccatcaaggc caggtggccg gtgccaactg
3121  tgtgagtgca gtgggaacat tgacccaatg gatcctgatg cctgtgaccc acacccccggg
3181  caatgcctgc gctgtttaca ccacacagag ggtccacact gtgcccactc gaagcctggc
```

FIG. 4B

```
3241  ttccatggcc aggctgcccg gcagagctgt caccgctgca catgcaacct gctgggcaca
3301  aatccgcagc agtgcccatc tcctgaccag tgccactgtg atccaagcag tgggcagtgc
3361  ccatgcctcc ccaatgtcca ggccctagct gtagaccgct gtgcccccaa cttctggaac
3421  ctcaccagtg gccatggttg ccagccttgt gcctgcctcc caagcccgga agaaggcccc
3481  acctgcaacg agttcacagg gcagtgccac tgcctgtgcg gctttggagg gcggacttgt
3541  tctgagtgcc aagagctcca ctggggagac cctgggttgc agtgccatgc ctgtgattgt
3601  gactctcgtg gaatagatac acctcagtgt caccgcttca caggtcactg cacgtgccgc
3661  ccagggggtgt ctggtgtgcg ctgtgaccag tgtgcccgtg gcttctcagg aatctttcct
3721  gcctgccatc cctgccatgc atgcttcggg gattgggacc gagtggtgca ggacttggca
3781  gcccgtacac agcgcctaga gcagcgggcg caggagttgc aacagacggg tgtgctgggt
3841  gcctttgaga gcagcttctg gcacatgcag gagaagctgg gcattgtgca gggcatcgta
3901  ggtgcccgca cacctcagc cgcctccact gcacagcttg tggaggccac agaggagctg
3961  cggcgtgaaa ttggggaggc cactgagcac ctgactcagc tcgaggcaga cctgacagat
4021  gtgcaagatg agaacttcaa tgccaaccat gcactaagtg gtctggagcg agataggctt
4081  gcacttaatc tcacactgcg gcagctcgac cagcatcttg acttgctcaa acattcaaac
4141  ttcctgggtg cctatgacag catccggcat gcccatagcc agtctgcaga ggcagaacgt
4201  cgtgccaata cctcagccct ggcagtacct agccctgtga gcaactcggc aagtgctcgg
4261  catcggacag aggcactgat ggatgctcag aaggaggact caacagcaa acacatggcc
4321  aaccagcggg cacttggcaa gctctctgcc catacccaca ccctgagcct gacagacata
4381  aatgagctgg tgtgtggggc ccagggattg catcatgatc gtacaagccc ttgtggggt
4441  gccggctgtc gagatgagga tgggcagccg cgctgtgggg gcctcagctg caatggggca
4501  gcggctacag cagacctagc actgggccgg gcccggcaca cacaggcaga gctgcagcgg
4561  gcactggcag aaggtggtag catcctcagc agagtggctg agactcgtcg gcaggcaagc
4621  gaggcacagc agcgggccca ggcagccctg gacaaggcta atgcttccag gggacaggtg
4681  gaacaggcca accaggaact tcaagaactt atccagagtg tgaaggactt cctcaaccag
4741  gaggggctg atcctgatag cattgaaatg gtggccacac gggtgctaga gctctccatc
4801  ccagcttcag ctgagcagat ccagcacctg gcgggcgcga ttgcagagcg agtccggagc
4861  ctggcagatg tggatgcgat cctggcacgt actgtaggag atgtgcgtcg tgccgagcag
4921  ctactgcagg atgcacggcg ggcaaggagc tgggctgagg atgagaaaca gaaggcagag
4981  acagtacagg cagcactgga ggaggcccag cgggcacagg gtattgccca gggtgccatc
5041  cgggggggcag tgctgacac acgggacaca gagcagaccc tgtaccaggt acaggagagg
5101  atggcaggtg cagagcgggc actgagctct gcaggtgaaa gggctcggca gttggatgct
5161  ctcctggagg ctctgaaatt gaaacgggca ggaaatagtc tggcagcctc tacagcagaa
5221  gaaacggcag gcagtgccca gggtcgtgcc caggaggctg agcagctgct acgcggtcct
5281  ctgggtgatc agtaccagac ggtgaaggcc ctagctgagc gcaaggccca aggtgtgctg
5341  gctgcacagg caagggcaga acaactgccg gatgaggctc gggacctgtt gcaagccgct
5401  caggacaagc tgcagcggct acaggaattg gaaggcacct atgaggaaaa tgagcgggca
5461  ctggagagta aggcagccca gttggacggg ttggaggcca ggatgcgcag cgtgcttcaa
5521  gccatcaact tgcaggtgca gatctacaac acctgccagt gacccctgcc caaggcctac
5581  cccagttcct agcactgccc cacatgcatg tctgcctatg cactgaagag ctcttggccc
5641  ggcagggccc ccaataaacc agtgtgaacc cccaaaaaaa aaa
```

FIG. 4C

Amino Acid Sequence and Nucleotide Sequence Encoding Gamma3 Chain

MAAAALLLGLALLAPRAAGAGMGACYDGAGRPQRCLPVFENAAFGRLAQASH
TCGSPPEDFCPHVGAAGAGAHCQRCDAADPQRHHNASYLTDFHSQDESTWWQS
PSMAFGVQYPTSVNITLRLGKAYEITYVRLKFHTSRPESFAIYKRSRADGPWEPY
QFYSASCQKTYGRPEGQYLRPGEDERVAFCTSEFSDISPLSGGNVAFSTLEGRPSA
YNFEESPGLQEWVTSTELLISLDRLNTFGDDIFKDPKVLQSYYYAVSDFSVGGRC
KCNGHASECGPDVAGQLACRCQHNTTGTDCERCLPFFQDRPWARGTAEAAHEC
LPCNCSGRSEECTFDRELFRSTGHGGRCHHCRDHTAGPHCERCQENFYHWDPR
MPCQPCDCQSAGSLHLQCDDTGTCACKPTVTGWKCDRCLPGFHSLSEGGCRPCT
CNPAGSLDTCDPRSGRCPCKENVEGNLCDRCRPGTFNLQPHNPAGCSSCFCYGH
SKVCASTAQFQVHHILSDFHQGAEGWWARSVGGSEHSPQWSPNGVLLSPEDEEE
LTAPGKFLGDQRFSYGQPLILTFRVPPGDSPLPVQLRLEGTGLALSLRHSSLSGPQ
DARASQGGRAQVPLQETSEDVAPPLPPFHFQRLLANLTSLRLRVSPGPSPAGPVF
LTEVRLTSARPGLSPPASWVEICSCPTGYTGQFCESCAPGYKREMPQGGPYASCV
PCTCNQHGTCDPNTGICVCSHHTEGPSCERCLPGFYGNPFAGQADDCQPCPCPGQ
SACTTIPESGEVVCTHCPPGQRGRRCEVCDDGFFGDPLGLFGHPQPCHQCQCSGN
VDPNAVGNCDPLSGHCLRCLHNTTGDHCEHCQEGFYGSALAPRPADKCMPCSC
HPQGSVSEQMPCDPVTGQCSCLPHVTARDCSRCYPGFFDLQPGRGCRSCKCHPL
GSQEDQCHPKTGQCTCRPGVTGQACDRCQLGFFGSSIKGCRACRCSPLGAASAQ
CHYNGTCVCRPGFEGYKCDRCHYNFFLTADGTHCQQCPSCYALVKEETAKLKA
RLTLTEGWLQGSDCGSPWGPLDILLGEAPRGDVYQGHHLLPGAREAFLEQMMG
LEGAVKAAREQLQRLNKGARCAQAGSQKTCTQLADLEAVLESSEEEILHAAAIL
ASLEIPQEGPSQPTKWSHLAIEARALARSHRDTATKIAATAWRALLASNTSYALL
WNLLEGRVALETQRDLEDRYQEVQAAQKALRTAVAEVLPEAESVLATVQQVG
ADTAPYLALLASPGALPQKSRAEDLGLKAKALEKTVASWQHMATEAARTLQTA
AQATLRQTEPLTMARSRLTATFASQLHQGARAALTQASSSVQAATVTVMGART
LLADLEGMKLQFPRPKDQAALQRKADSVSDRLLADTRKKTKQAERMLGNAAPL
SSSAKKKGREAEVLAKDSAKLAKALLRERKQAHRRASRLTSQTQATLQQASQQ
VLASEARRQELEEAERVGAGLSEMEQQIRESRISLEKDIETLSELLARLGSLDTHQ
APAQALNETQWALERLRLQLGSPGSLQRKLSLLEQESQQQELQIQGFESDLAEIR
ADKQNLEAILHSLPENCASWQ

```
  1 ccccgcaggg gaaggcgggt cctggcggcc agcgcgcggt ccgcgcccac cctagccgac
 61 ggggccggca gagcgcgcgg cgtcggtgcc cttgaccatg gcggcggctg cgcttctgct
121 ggggctggcg ctgctggcac cgcgggcggc cggcgcgggc atgggcgcgt gctatgacgg
181 cgcagggcgc ccgcagcgct gcctgccggt gttcgagaac gcggcgtttg gcggctcgc
241 ccaggcctcg cacacgtgcg gcagcccgcc cgaggacttc tgtccccacg tgggcgccgc
301 gggcgcgggg gctcattgcc agcgctgcga cgccgccgac ccccagcgcc accacaacgc
361 ctcctacctc accgacttcc acagccagga cgagagcacc tggtggcaga gcccgtccat
421 ggccttcggc gtgcagtacc ccacctcggt caacatcacc ctccgcctag ggaaggctta
481 tgagatcacg tatgtgaggc tgaagttcca caccagtcgc cctgagagct ttgccatcta
541 caagcgcagc cgcgccgacg gcccatggga gccctaccag ttctacagcg cctcctgcca
601 gaagacctac ggccggcccg agggccagta cctgcgcccc ggcgaggacg agcgcgtggc
661 cttctgcacc tctgagttca gcgacatctc cccgctgagt ggcggcaacg tggccttctc
721 caccctggag ggccggccca gcgcctacaa cttcgaggag agccctgggc tgcaggagtg
```

FIG. 5A

```
 781 ggtcaccagc accgaactcc tcatctctct agaccggctc aacacgtttg gggacgacat
 841 cttcaaggac cccaaggtgc tccagtccta ctattatgcc gtgtccgact tctctgtggg
 901 cggcaggtgc aagtgcaacg ggcatgccag cgagtgcggc cccgacgtgg caggccagtt
 961 ggcctgccgg tgccagcaca acaccaccgg cacagactgt gagcgctgcc tgcccttctt
1021 ccaggaccgc ccgtgggccc ggggcaccgc cgaggctgcc cacgagtgtc tgccctgcaa
1081 ctgcagtggc cgctccgagg aatgcacgtt tgatcgggag ctcttccgca gcacaggcca
1141 cggcgggcgc tgtcaccact gccgtgacca cacagctggg ccacactgtg agcgctgtca
1201 ggagaatttc tatcactggg acccgcggat gccatgccag ccctgtgact gccagtcggc
1261 aggctcccta cacctccagt gcgatgacac aggcacctgc gcctgcaagc ccacagtgac
1321 tggctggaag tgtgaccgct gtctgcccgg gttccactcg ctcagtgagg gaggctgcag
1381 accctgcact tgcaatcccg ctggcagcct ggacacctgt gaccccgca gtgggcgctg
1441 cccctgcaaa gagaatgtgg aaggcaacct atgtgacaga tgtcgcccgg ggacctttaa
1501 cctgcagccc cacaatccag ctggctgcag cagctgtttc tgctatggcc actccaaggt
1561 gtgcgcgtcc actgccagt tccaggtgca tcacatcctc agcgatttcc accgggagc
1621 cgaaggctgg tgggccagaa gtgtgggggg ctctgagcac tccccacaat ggagcccaaa
1681 tggggtcctc ctgagcccag aagacgagga ggagctcaca gcaccaggga agttcctggg
1741 agaccagcgg ttcagctatg ggcagcccct catactgacc ttccgggtgc ccccggggga
1801 ctccccactc cctgtacagc tgaggctgga agggacaggc ttggccctgt ccctgaggca
1861 ctctagcctg tctggccccc aggatgccag ggcatcccag ggaggtagag ctcaggttcc
1921 actgcaggag acctccgagg acgtggcccc tccactgccc cccttccact tccagcggct
1981 cctcgccaac ctgaccagcc tccgcctccg cgtcagtccc ggcccagcc ctgccggtcc
2041 agtgttcctg actgaggtcc ggctcacatc cgcccggcca gggctttccc cgccagcctc
2101 ctgggtggag atttgttcat gtcccactgg ctacacgggc cagttctgtg aatcctgtgc
2161 tccgggatac aagagggaga tgccacaggg gggtccctat gccagctgtg tccctgcac
2221 ctgtaaccag catggccacct gtgacccca cacagggatc tgtgtctgca gccaccatac
2281 cgagggccca tcctgtgaac gctgtttgcc aggtttctat ggcaacccct tcgcgggcca
2341 agccgacgac tgccagcct gtccctgccc tggccagtcg gcctgtacga ccatcccaga
2401 gagcggggag gtggtgtgta cccactgccc cccgggccag agagggcggc gctgtgaggt
2461 ctgtgatgat ggcttttttg gggacccgct ggggctcttt gggcacccc agccctgcca
2521 ccagtgccag tgtagcggga acgtggaccc caatgccgtg ggcaactgtg accccctgtc
2581 tggccactgc ctgcgctgcc tgcacaacac cacgggtgac cactgtgagc actgtcagga
2641 aggcttctac gggagcgccc tggcccctcg accgcagac aaatgcatgc cttgcagctg
2701 tcacccacag ggctcggtca gtgagcagat gccctgcgac ccagtgacag gccaatgctc
2761 ctgcctgcct catgtgactg cacgggactg cagccgctgc taccctggct tcttcgacct
2821 ccagcctggg agggggctgcc ggagctgcaa gtgtcaccca ctgggctccc aggaggacca
2881 gtgccatccc aagactggac agtgcacctg ccgcccaggt gtcacaggcc aggcctgtga
2941 caggtgccag ctgggtttct tcggctcctc aatcaagggc tgccgggcct gcaggtgctc
3001 cccactgggc gctgcctcgg cccagtgcca ctataacggc acatgcgtgt gcaggcctgg
3061 cttcgagggc tacaaatgtg accgctgcca ctacaacttc ttcctcacgg cagacggcac
3121 acactgccag caatgtccgt cctgctacgc cctggtgaag gaggagacag ccaagctgaa
3181 ggccagactg actttgacgg aggggtggct ccaagggtcc gactgtggca gtccctgggg
3241 accactagac attctgctgg gagaggcccc aaggggggac gtctaccagg ccatcacct
3301 gcttccaggg gctcgggaag ccttcctgga gcagatgatg ggcctcgagg gtgctgtcaa
3361 ggccgcccgg gagcagctgc agaggctgaa caagggtgcc cgctgtgccc aggccggatc
3421 ccagaagacc tgcacccagc tggcagacct ggaggcagtg ctggagtcct cggaagagga
3481 gattctgcat gcagctgcca ttctcgcgtc tctggagatt cctcaggaag gtcccagtca
```

FIG. 5B

LAMININ 15

This application claims the benefit of U.S. Provisional Application No. 60/200,863, filed on May, 1, 2000.

BACKGROUND OF THE INVENTION

Laminins are large heterotrimeric glycoproteins of the extracellular matrix. Each laminin heterotrimer is composed of an α, a β, and a γ chain, chosen from a number of possible homologues of each chain. Currently, eleven laminin chains have been identified: five α chains, three β chains, and three γ chains (Timpl (1996) *Curr Opin Cell Biol* 8: 618–624).

SUMMARY OF THE INVENTION

The invention is based, in part, on the discovery of a novel member of the laminin family, laminin 15. Accordingly, the invention features a purified or isolated preparation, a recombinant preparation, or a composition of laminin 15, which includes laminin chains α5, β2, and γ3. In a preferred embodiment, the laminin 15 is a trimer of an α5, β2, and γ3 chain. In a preferred embodiment the laminin 15 is human laminin 15.

In a preferred embodiment the α5 chain has a molecular weight of 380 kD, or 330 kD, the β2 chain has a molecular weight of 190 kD or 170 kD, the γ3 chain has a molecular weight of 220 kD, 200 kD or 170 kD.

In another preferred embodiment, the α5 chain is reactive with or specifically binds an α5-specific antibody, e.g., the mouse monoclonal antibody 4C7 (Engvall et al. (1986) *J Cell Biol* 103:2457–2465), or an antibody of the same laminin chain-specificity, e.g., one which can compete for the 4C7 epitope. In another preferred embodiment, the β2 chain is reactive with or specifically binds a β2 specific antibody, e.g., a guinea pig polyclonal GP1 (Sanes et al. (1990) *J Cell Biol* 111:1685–1699), mouse monoclonal C4 (Sanes et al. (1983) *Cold Spring Harb Symp Quant Biol* 48: 667–678), or an antibody of the same laminin chain-specificity, e.g., one which can compete for the GP1 or C4 epitope. In another preferred embodiment, the γ3 chain is reactive with or specifically binds γ3 specific a antibody, e.g., the rabbit antibody R16 or the rabbit antibody R21 (Koch et al. (1999) *J Cell Biol* 145: 605–618), or an antibody of the same laminin chain specificity, e.g., one which competes for the R16 or R21 binding site.

In yet another preferred embodiment, the α5 chain has the amino acid sequence of SEQ ID NO: 2 or SEQ ID NO: 4. In a preferred embodiment, the α5 chain is at least 60%, 65%, 70%, 75%, 80%, 85%, 90%, 95% 98%, 99% homologous to the amino acid sequence of SEQ ID NO: 2 or SEQ ID NO: 4. In a preferred embodiment, the α5 chain differs from the amino acid sequence of SEQ ID NO: 2 or SEQ ID NO: 4, by at least one, but less than 5, 10, 15 amino acid residues, e.g., by at least one, but less than 5, 10, 15 non-essential amino acid residues. Preferably, the α5 chain retains the ability to form a heterotrimer with the β2 chain and the γ3 chain.

In another preferred embodiment, the β2 chain has the amino acid sequence of SEQ ID NO: 6 or SEQ ID NO: 8. In a preferred embodiment, the β2 chain is at least 60%, 65%, 70%m, 75%, 80%, 85%, 90%, 95%, 98%, 99% homologous to the amino acid sequence of SEQ ID NO: 6 or SEQ ID NO: 8. In a preferred embodiment, the β2 chain differs from the amino acid sequence of SEQ ID NO: 6 or SEQ ID NO: 8, by at least one, but less than 5, 10, 15 amino acid residues, e.g., by at least one, but less than 5, 10, 15 non-essential amino acid residues. Preferably, the β2 chain retains the ability to form a heterotrimer with the α5 chain and the γ3 chain.

In another preferred embodiment, the γ3 chain has the amino acid sequence of SEQ ID NO: 10. In a preferred embodiment, the γ3 chain is at least 60%, 65%, 70%, 75%, 80%, 85%, 90%, 95%, 98% 99% homologous to the amino acid sequence of SEQ ID NO: 10. In a preferred embodiment, the γ3 chain differs from the amino acid sequence of SEQ ID NO: 10, by at least one, but less than 5, 10, 15 amino acid residues, e.g., by at least one, but less than 5, 10, 15 non-essential amino acid residues. Preferably, the γ3 chain retains the ability to form a heterotrimer with the α5 chain and the β2 chain.

In another aspect, the invention features, a purified or isolated preparation, a recombinant preparation, or composition of laminin 15, which includes laminin chains α5, β2, γ3. In a preferred embodiment, the laminin 15 is a trimer of an α5, β2, and γ3 chain. In a preferred embodiment, the laminin 15 is human laminin 15.

The laminin chains of any laminin as disclosed herein can be the initial translation product or a degradation product, e.g., a naturally occurring degradation product of a laminin chain.

In another aspect, the invention features an isolated nucleic acid, e.g., DNA, RNA or cDNA encoding laminin 15, i.e., which encodes α5, β2, or γ3. The isolated nucleic acid can be a combination of nucleic acids each encoding one or more laminin 15 chains or a single nucleic acid, e.g., if in a vector, one or more of the chains can be in one vector or each chain can be in a separate vector. The α5 can be, e.g., any α5 chain described herein. In a preferred embodiment, the nucleic acid encoding the α5 chain has the nucleotide sequence of SEQ ID NO: 1 or SEQ ID NO: 3. In a preferred embodiment, the nucleic acid encoding the α5 chain has at least 60%, 65%, 70%, 75%, 80%, 85%, 90%, 95%, 98%, 99% homology, or has the nucleotide sequence of SEQ ID NO: 1 or SEQ ID NO: 3. In another preferred embodiment, the nucleic acid encoding the α5 chain hybridizes, e.g., hybridizes under stringent conditions, to the nucleotide sequence of SEQ ID NO: 1 or SEQ ID NO: 3. The β2 chain can be, e.g., any β2 chain described herein. In a preferred embodiment, the nucleic acid encoding the β2 chain has the nucleotide sequence of SEQ ID NO: 5 or SEQ ID NO: 7. In a preferred embodiment, the nucleic acid encoding the β2 chain has at least 60%, 65%, 70%, 75%, 80%, 85%, 90%, 95%, 98%, 99% homology, or has the nucleotide sequence of SEQ ID NO: 5 or SEQ ID NO: 7. In another preferred embodiment, the nucleic acid encoding the 132 chain hybridizes, e.g., hybridizes under stringent conditions, to the nucleotide sequence of SEQ ID NO: 5 or SEQ ID NO: 7. The γ3 chain can be, e.g., any γ3 chain described herein. In a preferred embodiment, the nucleic acid encoding the γ3 chain has the nucleotide sequence of SEQ ID NO: 9. In a preferred embodiment, the nucleic acid encoding the γ3 chain has at least 60%, 65%, 70%, 75%, 80%, 85%, 90%, 95%, 98%, 99% homology, or has the nucleotide sequence of SEQ ID NO: 9. In another preferred embodiment, the nucleic acid encoding the γ3 chain hybridizes, e.g., hybridizes under stringent conditions, to the nucleotide sequence of SEQ ID NO: 9.

In a preferred embodiment, the isolated nucleic acid can be expressed in one or more vectors, e.g., an expression vector or expressed directly in a cell. A vector (or vectors) containing a sequence corresponding to the sequence of the isolated nucleic acid can express the isolated nucleic acid in a suitable cell or a suitable in vitro environment.

In another aspect, the invention features producing laminin 15 from a cell transfected with nucleic acid encoding a laminin 15, e.g., a laminin 15 described herein.

In another aspect, the invention features producing laminin 15 from a cell transfected with nucleic acid which encodes one or more of an α5 chain, a β2 chain and/or a γ3 chain, e.g., a nucleic acid described herein.

In another aspect, the invention features a recombinant laminin 15 which can be produced, e.g., by expressing the laminin chains of laminin 15 in a suitable cell host and under a condition suitable for the laminin chains to form laminin 15.

In a preferred embodiment, the laminin 15 differs from a naturally occurring laminin 15 by at least 1, but less than 5, 10, or 15 amino acid residues. In another embodiment, one, two, or each laminin chain of a laminin, differs from its naturally occurring counterpart by at least 1, but less than 5, 10, or 15 amino acid residues.

The invention provides a method for treating a disorder associated with abnormal functions of synapses, e.g., insufficient stability, viability, formation, and/or defective organization of synapses. The method comprises administering to a subject an effective amount of: laminin 15, laminin 14, or a combination thereof.

The invention further provides a method for modulating retinal development, e.g., in the subretinal space, in the interphotoreceptor matrix, and/or in the outer plexiform layer. The method comprises administering to a subject an effective amount of: laminin 15, laminin 14, or a combination thereof.

The invention provides a method for treating a disorder associated with: insufficient neural cell growth, healing and regeneration, e.g., axon outgrowth; a disorder associated with abnormal subretinal space or interphotoreceptor matrix (IPM) such as inadequate stability of IPM; a disorder associated with retina contact, continuity, and/or adhesion; a disorder associated with abnormal and/or insufficient formation of synapses; a disorder associated with viability of a neural cell, e.g., photoreceptor or an element thereof, e.g., outer segment, inner segment, cell body, and/or synapses. The method comprises administering to a subject an effective amount of laminin 15, laminin 14, or a combination thereof.

Another feature of the present invention provides a method of treating a disorder associated with retinal abnormality, e.g., rod dystrophy, rod-cone dystrophy, macular degeneration, retinitis pigmentosa, or retinal detachment. The method includes administering to a subject an effective amount of: laminin 15, laminin 14, or a combination thereof Another feature of the present invention provides a method of inducing neural cell growth and/or regeneration, e.g., axon outgrowth. The method includes administering to a subject an effective amount of laminin 15, laminin 14, or a combination thereof. In a preferred embodiment, the method can be used to induce neural cell growth or regeneration in the central nervous system (CNS) and/or the peripheral nervous system (PNS).

In a preferred embodiment, the method includes administering to a wound an effective amount of: laminin 15, laminin 14, or a combination thereof.

Still another feature of the invention provides a method of promoting a condition, e.g., promoting retina interphotoreceptor matrix stability; promoting the production, stability, and/or development of a retina photoreceptor or an element thereof, e.g., outer segment, inner segment, cell body, and/or synapses; promoting retinal contact, continuity, and/or adhesion; promoting the stability of synapses; and/or promoting the formation of synapses. The method includes administering an effective amount of: laminin 15, laminin 14, or a combination thereof.

Another feature of the invention provides a method for preparing an implant. For example, a method of preparing an implantable tip, an implantable catheter, a retinal implant, a timed releasing device, a neural cell growth guide, an artificial tissue, an implant of the central nervous system, or an implant of the peripheral nervous system. The method includes contacting, e.g., coating or incubating, the implant with laminin 15. In a preferred embodiment, laminin 15, laminin 14, or combinations thereof, can be used for treatment of a damaged eye, e.g., to increase photosentivity in an eye, e.g., by implanting a tip coated with laminin 15, laminin 14, or a combination thereof, into the eye.

In a preferred embodiment, the implant is a subretinal implant, e.g., subretinal microphotodiodes, a visual prosthesis, e.g., a photoreceptive prosthesis (e.g., as reviewed in Peachey, *J Rehabil Res Dev* (1999) 36(4) :371–6), an implant for photoreceptor replacement, a phototransistor, or a subretinally implanted microphotodiode array (MPDA) implant. Such implants are described in Zrenner et al. (1997) *Ophthalmic Res* 29(5):269–80; Zrenner et al. (1999) *Vision Res* 39(15):2555–67, or in the abstract entitled "Can Subretinal Microphotodiodes Successfully Replace Degenerated hotoreceptors?" submitted by E. Zrenner et al. at the Vision Research Conference held on May 9, 1998. An example of a corneal keratoprosthesis (the Aachen-Keratoprosthesis) is described in Kompa et al. (2000) *Int J Artif Organs* 23(5):345–8.

A method of evaluating a compound for the ability to interact with, e.g., bind, a subject laminin 15 is provided. The method includes: contacting the compound with the subject laminin 15; and evaluating ability of the compound to interact with, e.g., to bind or form a complex with the subject laminin 15. This method can be performed in vitro, e.g., in a cell free system, or in vivo. This method can be used to identify naturally occurring molecules which interact with subject laminin 15. It can also be used to find natural or synthetic inhibitors of subject laminin 15. Screening methods are discussed in more detail below.

In one embodiment, an assay is a cell-based assay in which a cell which expresses laminin 15 or biologically active portion thereof is contacted with a test compound, and the ability of the test compound to modulate laminin 15 activity is determined.

The ability of the test compound to modulate laminin 15 binding to a compound, e.g., a laminin 15 substrate, or to bind to laminin 15 can also be evaluated.

Soluble and/or membrane-bound forms of isolated proteins (e.g., laminin 15 or biologically active portions thereof can be used in the cell-free assays of the invention. When membrane-bound forms of the protein are used, it may be desirable to utilize a solubilizing agent. Examples of such solubilizing agents include non-ionic detergents such as n-octylglucoside, n-dodecylglucoside, n-dodecylmaltoside, octanoyl-N-methylglucamide, decanoyl-N-methylglucamide, Triton® X-100, Triton® X-114, Thesit®, Isotridecypoly(ethylene glycol ether)$_n$, 3-[(3-cholamidopropyl)dimethylamminio]-1-propane sulfonate (CHAPS), 3-[(3-cholamidopropyl) dimethylamminio]-2-hydroxy-1-propane sulfonate (CHAPSO), or N-dodecyl=N, N-dimethyl-3-ammonio-1-propane sulfonate.

Cell-free assays involve preparing a reaction mixture of the target gene protein and the test compound under conditions and for a time sufficient to allow the two components to interact and bind, thus forming a complex that can be removed and/or detected.

In a preferred embodiment, the assay includes contacting laminin 15 or biologically active portion thereof with a known compound which binds laminin 15 to form an assay mixture, contacting the assay mixture with a test compound, and determining the ability of the test compound to interact with laminin 15, wherein determining the ability of the test compound to interact with laminin 15 includes determining the ability of the test compound to preferentially bind to laminin 15 or biologically active portion thereof, or to modulate the activity of a target molecule, as compared to the known compound.

In another aspect, the invention provides, a method of determining if a subject is at risk for a disorder, e.g., a disorder described herein.

In a preferred embodiment, the disorder is related to a lesion in or the misexpression of a gene which encodes one or more of a laminin 15 chain, e.g., one or more of an α5 chain, the β2 chain, and/or γ3 chain.

Such disorders include, e.g., a disorder associated with the misexpression of a laminin 15 chain, a disorder associated with the central nervous system and/or the peripheral nervous system, a retinal disorder.

The method includes one or more of the following:

detecting, in a tissue of the subject, the presence or absence of a mutation which affects the expression of one or more of a laminin 15 chain gene, e.g., one or more of an α5 chain, the β2 chain, or γ3 chain, or detecting the presence or absence of a mutation in a region which controls the expression of the gene, e.g., a mutation in the 5' control region;

detecting, in a tissue of the subject, the presence or absence of a mutation which alters the structure one or more of a laminin 15 chain gene, e.g., one or more of an α5 chain, the β2 chain, or γ3 chain gene;

detecting, in a tissue of the subject, the misexpression of one or more of a laminin 15 chain gene, e.g., one or more of an α5 chain, the β2 chain, or γ3 chain gene, at the mRNA level, e.g., detecting a non-wild type level of a mRNA;

detecting, in a tissue of the subject, the misexpression of the gene, at the protein level, e.g., detecting a non-wild type level of laminin 15.

In preferred embodiments the method includes: ascertaining the existence of at least one of: a deletion of one or more nucleotides from one or more of a laminin 15 chain gene, e.g., one or more of an α5 chain, the β2 chain, or γ3 chain gene; an insertion of one or more nucleotides into the gene, a point mutation, e.g., a substitution of one or more nucleotides of the gene, a gross chromosomal rearrangement of the gene, e.g., a translocation, inversion, or deletion.

For example, detecting the genetic lesion can include: (i) providing a probe/primer including an oligonucleotide containing a region of nucleotide sequence which hybridizes to a sense or antisense sequence from SEQ ID NO: or naturally occurring mutants thereof or 5' or 3' flanking sequences naturally associated with one or more of a laminin 15 chain gene, e.g., one or more of an α5 chain, the β2 chain, or γ3 chain gene; (ii) exposing the probe/primer to nucleic acid of the tissue; and detecting, by hybridization, e.g., in situ hybridization, of the probe/primer to the nucleic acid, the presence or absence of the genetic lesion.

In preferred embodiments detecting the misexpression includes ascertaining the existence of at least one of: an alteration in the level of a messenger RNA transcript of one or more of a laminin 15 chain gene, e.g., one or more of an α5 chain, the β2 chain, or γ3 chain gene; the presence of a non-wild type splicing pattern of a messenger RNA transcript of the gene; or a non-wild type level of laminin 15.

Methods of the invention can be used prenatally or to determine if a subject's offspring will be at risk for a disorder.

In preferred embodiments the method includes determining the structure of one or more of a laminin 15 chain gene, e.g., one or more of an α5 chain, the β2 chain, or γ3 chain gene, an abnormal structure being indicative of risk for the disorder.

In preferred embodiments the method includes contacting a sample from the subject with an antibody to one or more of the α5 chain, the β2 chain, or γ3 chain, or a nucleic acid, which hybridizes specifically with the gene.

In another aspect, the invention provides a method for preventing in a subject, a disease or condition associated with an aberrant or unwanted expression of one or more of a laminin 15 chain or a laminin 15 activity, by administering to the subject laminin 15 or an agent which modulates expression of one or more laminin 15 chain or at least one laminin 15 activity. Subjects at risk for a disease which is caused or contributed to by aberrant or unwanted laminin 15 activity or expression of one or more laminin 15 chain can be identified by, for example, any or a combination of diagnostic or prognostic assays as described herein. Administration of a prophylactic agent can occur prior to the manifestation of symptoms characteristic of the laminin 15 aberrance, such that a disease or disorder is prevented or, alternatively, delayed in its progression. Depending on the type of laminin 15 aberrance, for example, a laminin 15 agonist or laminin 15 antagonist agent can be used for treating the subject. The appropriate agent can be determined based on screening assays described herein.

It is possible that some laminin 15 disorders can be caused, at least in part, by an abnormal level of gene product, or by the presence of a gene product exhibiting abnormal activity. As such, the reduction in the level and/or activity of such gene products would bring about the amelioration of disorder symptoms.

The term "effective amount" means the amount that is sufficient to reduce or alleviate at least one adverse effect or symptom of a disorder and/or to induce or enhance at least one biological activity of laminin 15. A biological activity of laminin 15 includes one or more of the ability to: 1) modulate retinal development, e.g., in the subretinal space, the interphotoreceptor matrix, the outer plexiform layer; 2) modulate, e.g., promote, neural cell growth and regeneration, e.g., axonal outgrowth; 3) modulate, e.g., promote, adhesion between cells and/or extracellular matrix, e.g., retinal contact; 4) modulate, e.g., promote, synaptic formation; 5) modulate, e.g., promote, viability of a neural cell, e.g., a neural retinal cell, e.g., a photoreceptor or an element thereof, e.g., outer segment, inner segment, cell body or synapses; 6) interact, e.g., form a complex, with a dystrophin and/or a P-dystroglycan. An effective amount can be determined by one skilled in the art, e.g., based on the disease stage, age, sex, and weight of the to be treated subject and the condition of the treatment. As a reference, the amount administered can be at a concentration of at least from about 0.1 to 500 pg/ml, from about 1 to 200 g/ml, from about 10 to 150 g/ml, or from about 10 to 100 g/ml.

The term "isolated or purified nucleic acid molecule" includes nucleic acid molecules which are separated from other nucleic acid molecules which are present in the natural source of the nucleic acid. For example, with regards to genomic DNA, the term "isolated" includes nucleic acid molecules which are separated from the chromosome with which the genomic DNA is naturally associated. Preferably, an "isolated" nucleic acid is free of sequences which naturally flank the nucleic acid (i.e., sequences located at the 5' and/or 3' ends of the nucleic acid) in the genomic DNA of the organism from which the nucleic acid is derived. For example, in various embodiments, the isolated nucleic acid molecule can contain less than about 5 kb, 4kb, 3kb, 2kb, 1 kb, 0.5 kb or 0.1 kb of 5' and/or 3' nucleotide sequences which naturally flank the nucleic acid molecule in genomic DNA of the cell from which the nucleic acid is derived. Moreover, an "isolated" nucleic acid molecule, such as a cDNA molecule, can be substantially free of other cellular material, or culture medium when produced by recombinant techniques, or substantially free of chemical precursors or other chemicals when chemically synthesized.

As used herein, the term "hybridizes under stringent conditions" describes conditions for hybridization and washing. Stringent conditions are known to those skilled in the art and can be found in *Current Protocols in Molecular Biology*, John Wiley &Sons, N. Y. (1989), 6.3.1–6.3.6. Aqueous and nonaqueous methods are described in that reference and either can be used. A preferred, example of stringent hybridization conditions are hybridization in 6× sodium chloride/sodium citrate (SSC) at about 45° C., followed by one or more washes in 0.2× SSC, 0.1% SDS at 50° C. Another example of stringent hybridization conditions are hybridization in 6× sodium chloride/sodium citrate (SSC) at about 45° C., followed by one or more washes in 0.2× SSC, 0.1% SDS at 55° C. A further example of stringent hybridization conditions are hybridization in 6× sodium chloride/sodium citrate (SSC) at about 45° C., followed by one or more washes in 0.2× SSC, 0.1% SDS at 60° C. Preferably, stringent hybridization conditions are hybridization in 6× sodium chloride/sodium citrate (SSC) at about 45° C., followed by one or more washes in 0.2× SSC, 0.1%SDS at 65° C. Particularly preferred stringency conditions (and the conditions that should be used if the practitioner is uncertain about what conditions should be applied to determine if a molecule is within a hybridization limitation of the invention) are 0.5M Sodium Phosphate, 7% SDS at 65° C., followed by one or more washes at 0.2× SSC, 1% SDS at 65° C. Preferably, an isolated nucleic acid molecule of the invention that hybridizes under stringent conditions to the sequence of SEQ ID NO: 1,3, 5, 7, or 9, or corresponds to a naturally-occurring nucleic acid molecule.

As used herein, a "naturally-occurring" nucleic acid molecule refers to an RNA or DNA molecule having a nucleotide sequence that occurs in nature (e.g., encodes a natural protein).

An "isolated" or "purified" polypeptide or protein is substantially free of cellular material or other contaminating proteins from the cell or tissue source from which the protein is derived, or substantially free from chemical precursors or other chemicals when chemically synthesized. In one embodiment, the language "substantially free" means preparation of laminin 15 having less than about 30%, 20%, 10% and more preferably 5% (by dry weight), of non-laminin 15 protein (also referred to herein as a "contaminating protein"), or of chemical precursors or non-laminin 15 chemicals. When the protein or biologically active portion thereof is recombinantly produced, it is also preferably substantially free of culture medium, i.e., culture medium represents less than about 20%, more preferably less than about 10%, and most preferably less than about 5% of the volume of the protein preparation. The invention includes isolated or purified preparations of at least 0.01, 0.1, 1.0, and 10 milligrams in dry weight.

A "non-essential" amino acid residue is a residue that can be altered from the wild-type sequence of a laminin 15 chain (e.g., the sequence of SEQ ID NO: 1, 3, 5, 7, or 9) without abolishing or more preferably, without substantially altering a biological activity, whereas an "essential" amino acid residue results in such a change. For example, amino acid residues that are conserved among the polypeptides of the present invention, e.g., those present which mediate assembly and are predicted to be particularly unamenable to alteration.

A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), betabranched side chains (e.g., threonine, valine, isoleucine) and aromatic side chains (e.g., tyrosine, phenylalanine, tryptophan, histidine). Thus, a predicted nonessential amino acid residue in a protein is preferably replaced with another amino acid residue from the same side chain family. Alternatively, in another embodiment, mutations can be introduced randomly along all or part of a laminin 15 chain coding sequence, such as by saturation mutagenesis, and the resultant mutants can be screened for a laminin 15 biological activity to identify mutants that retain activity. Following mutagenesis of SEQ ID NO: 1, 3, 5, 7, or 9, the encoded protein can be expressed recombinantly and the activity of the protein can be determined.

Calculations of homology or sequence identity between sequences (the terms are used interchangeably herein) are performed as follows.

To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 30%, preferably at least 40%, more preferably at least 50%, even more preferably at least and even 60%, more preferably at least 70%, 80%, 90%, 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In a preferred embodiment, the percent identity between two amino acid sequences is determined using the Needleman and Wunsch ((1970) *J Mol Biol* (48): 444–453) algorithm which has been incorporated into the GAP program in the GCG software package (available online), using either a Blossum 62 matrix or a PAM250 matrix, and a gap weight of 16, 14, 12, 10, 8,6, or 4 and a length weight of 1, 2, 3, 4, 5, or 6. In yet another preferred embodiment, the percent identity between two nucleotide sequences is determined using the GAP program in the GCG software package (available online), using a NWSgapdna. CMP matrix and a gap weight of 40, 50,60, 70, or 80 and a length weight of 1, 2, 3, 4, 5, or 6. A particularly preferred set of parameters (and the one that should be used if the practitioner is uncertain about what parameters should be applied to determine if a molecule is within a sequence identity or homology limitation of the invention) are a Blossum 62 scoring matrix with a gap penalty of 12, a gap extend penalty of 4, and a frameshift gap penalty of 5.

The percent identity between two amino acid or nucleotide sequences can be determined using the algorithm of E. Meyers and W. Miller (CABIOS, 4:11–17 (1989)) which has been incorporated into the ALIGN program (version 2.0), using a PAM 120 weight residue table, a gap length penalty of 12 and a gap penalty of 4.

"Misexpression or aberrant expression", as used herein, refers to a non-wild type pattern of gene expression, at the RNA or protein level. It includes: expression at nonwild type levels, i.e., over or under expression; a pattern of expression that differs from wild type in terms of the time or stage at which the gene is expressed, e.g., increased or decreased expression (as compared with wild type) at a predetermined developmental period or stage; a pattern of expression that differs from wild type in terms of decreased expression (as compared with wild type) in a predetermined cell type or tissue type; a pattern of expression that differs from wild type in terms of the splicing size, amino acid sequence, post-transitional modification, or biological activity of the expressed polypeptide; a pattern of expression that differs from wild type in terms of the effect of an environmental stimulus or extracellular stimulus on expression of the gene, e.g., a pattern of increased or decreased expression (as compared with wild type) in the presence of an increase or decrease in the strength of the stimulus.

A "purified preparation of cells", as used herein, refers to, in the case of plant or animal cells, an in vitro preparation of cells and not an entire intact plant or animal. In the case of cultured cells or microbial cells, it consists of a preparation of at least 10% and more preferably 50% of the subject cells.

The term "subject" as used herein refers to a mammal. Examples of mammals include human and nonhuman primates, e.g., a monkey, a goat, or a rodent, e.g., a rat or a mouse, having a disorder associated with insufficient laminin, e.g., laminin 15 activity. The mammal is preferably a primate, e.g., a human.

As used herein the term "administering" refers to delivery of a preparation, composition, an active portion, or an active fragment of laminin 15 alone, in combination with another laminin (e.g., laminin 5, laminin 14) and/or at least one other compound or preparation.

The term "stability" means structural, anatomic molecular, and/or functional integrity, intactness, or completeness which is testable or observable by any suitable means. For example, the stability of retina photoreceptor can be tested by ERG, e.g., indicated by a wave and b wave.

The term "pharmaceutically acceptable carrier" is intended to include a solvent, dispersion media, coatings, antibacterial and antifungal agents, isotonic and absorption delaying agents, and the like, compatible with pharmaceutical administration. The use of such media and agents for pharmaceutically active substances is well known in the art. Such carriers include, but are not limited to, large, slowly metabolized macromolecules, such as proteins, polysaccharides, polylactic acids, polyglycolic acids, polymeric amino acids, amino acid copolymers, and inactive virus particles. Pharmaceutically acceptable salts can also be used in the composition, for example, mineral salts such as hydrochlorides, hydrobromides, phosphates, or sulfates, as well as the salts of organic acids such as acetates, proprionates, malonates, or benzoates. The composition can also contain liquids, such as water, saline, glycerol, and ethanol, as well as substances such as wetting agents, emulsifying agents, or pH buffering agents.

Liposomes, such as those described in U.S. Pat. No. 5,422,120; WO 95/13796; WO 91114445; or EP 524,968 B1, can also be used as a carrier. Typically, the therapeutic laminin composition is prepared as an injectable, either as a liquid solution or suspension; however, solid forms suitable for solution in, or suspension in, liquid vehicles prior to injection can also be prepared. The composition can also be formulated into an entericcoated tablet or gel capsule according to known methods in the art, such as those described in U.S. Pat. No. 4,853,230; EP 225,189; AU 9,224,296; and AU 9,230,801.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

BRIEF DESCRIPTION OF THE FIGURES

FIGS. 1A–1F depicts the nucleotide sequence of murine α5 (SEQ ID NO: 1) and the amino acid sequence of murine α5 (SEQ ID NO: 2).

FIGS. 2A–2B depicts the nucleotide sequence of human α5 (SEQ ID NO: 3) and the amino acid sequence of human α5 (SEQ ID NO: 4).

FIGS. 3A–3C depicts the nucleotide sequence of murine β2 (SEQ ID NO: 5) and the amino acid sequence of murine β2 (SEQ ID NO: 6).

FIGS. 4A–4C depicts the nucleotide sequence of human β2 (SEQ ID NO: 7) and the amino acid sequence of human β2 (SEQ ID NO: 8).

FIGS. 5A–5B depicts the nucleotide sequence of murine γ3 (SEQ ID NO: 9) and the amino acid sequence of murine γ3 (SEQ ID NO: 10).

DETAILED DESCRIPTION

The invention features a novel member of the laminin family, i.e., laminin 15, and methods of making and using this novel laminin, e.g., in neural associated disorders.

In the methods of treating a disorder, such as a disorder described herein, laminin 15 can be administered alone, or in combination with at least one other laminin (e.g., laminin 5 and/or laminin 14) and/or with at least one other compound or preparation. Administration can include local or systemic administration, including injection, oral administration, particle gun, or catheterized administration, and topical administration. Various methods can be used to administer a therapeutic composition of laminin 15 alone, or in combination with one another laminin, and/or compound, directly to a specific site in the body. For example, a small neural wound can be located and the therapeutic composition can be applied, e.g., once or several times in one or several different locations, within the wound. A therapeutic laminin 15 composition can be directly administered to the surface of a neural wound, for example, by topical application of the composition, or can be injected into the site of a neural wound, e.g., as part of a liquid solution or suspension. X-ray imaging can be used to assist in delivery of laminin 15 to a site, e.g., the site of a neural wound. Combination therapeutic agents, including a laminin 15 protein, a laminin 15 polypeptide, or a subgenomic laminin 15 polynucleotide, and other therapeutic agents, can be administered simultaneously or sequentially. The administration of therapeutic agents can be repeated.

Receptor-mediated targeted delivery of therapeutic compositions containing laminin 15 subgenomic polynucleotides to specific tissues can also be used. Receptor mediated DNA delivery techniques are described in, for example, Findeis et al., 1993, *Trends in Biotechnol. II* 202–0.5; Chiou et al., 1994, GENE THERAPEUTICS: METHODS AND APPLICATIONS OF DIRECT GENE TRANSFER (J. A. Wolff, ed.); Wu & Wu., 1988, *J. Biol. Chem.* 263,621–24; Wu et al. (1994) *J Biol Chem* 269, 542–546; Zenke et al. (1990) *Proc Natl Acad Sci U.S.A.* 87:3655–59; Wu et al. (1991) *J Biol Chem* 266:338–42.

Alternatively, a laminin 15 composition can be introduced into human cells ex vivo, and the cells then replaced into the human. Cells can be removed from a variety of locations including, for example, from a selected neural tissue or from an affected organ. Both the dose of the laminin 15 composition and the means of administration can be determined based on the specific qualities of the therapeutic composition, the condition, age, and weight of the patient, the progression of the disease, and other relevant factors. If the composition contains a laminin 15 protein or polypeptide, effective dosages of the composition are in the range of about 5 pg to about 50 pg/kg of patient body weight, about 50 pg to about 5 mg/kg, about 100 pg to about 500 pg/kg of patient body weight, and about 200 to about 250 pg/kg.

Therapeutic compositions containing a laminin 15 subgenomic polynucleotide can be administered in a range of about 100 ng to about 200 mg of DNA for local administration in a gene therapy protocol. Concentration ranges of about 500 ng to about 50 mg, about 1 pg to about 2 mg, about 5 pg to about 500 pg, and about 20 pg to about 100 pg of DNA can also be used during a gene therapy protocol. Factors such as method of action and efficacy of transformation and expression should be considered in determining the dosage of laminin 15 polynucleotide required. Where greater expression is desired over a larger area of tissue, larger amounts of laminin 15 subgenomic polynucleotides and/or the same amounts of laminin 15 subgenomic polynucleotides can be readministered, e.g., in a successive protocol of administrations, or several administrations to different adjacent or in close proximity to the targeted tissue portions.

For example, a tumor site may be required to effect a positive therapeutic outcome. In all cases, routine experimentation in clinical trials will determine specific ranges for optimal therapeutic effect.

Isolation or recombinant production of laminin 15 (α5 β2 β3)

Laminin 15 consists of an α5 chain, a β2 chain and a γ3 chain. The laminin chain can be isolated and purified from a natural source, e.g., from a retinal tissue such as the retina inter-photoreceptor matrix, the retina outer plexiform layer, the neural retina, a Müller cell, and/or a preparation of retinal neurons.

Alternatively, laminin 15 can be produced recombinantly or chemically synthesized by conventional methods. The nucleotide and amino acid sequences of the laminin chains are known and described, for example, at Genbank Accession Number U37501 (murine α5 chain), Genbank Accession Number: AW4 11963 (murine β2 chain), and in Koch et al., *J Cell Biol* (1999) 145: 605–618 (murine γ3 chain).

Methods of generating a recombinant laminin 15 protein are well known in the art. For example, the laminin 15 protein can be generated by cloning the nucleic acid sequence encoding each of the laminin chains into an expression vector, where it is operably linked to one or more expression control sequences.

A vector can include one or more of an α5 chain, the β2 chain, and γ3 chain nucleic acid in a form suitable for expression of the nucleic acid in a host cell. Preferably the recombinant expression vector includes one or more regulatory sequences operatively linked to the nucleic acid sequence to be expressed. The term "regulatory sequence" includes promoters, enhancers and other expression control elements (e.g., polyadenylation signals). Regulatory sequences include those which direct constitutive expression of a nucleotide sequence, as well as tissue-specific regulatory and/or inducible sequences. The design of the expression vector can depend on such factors as the choice of the host cell to be transformed, the level of expression of protein desired, and the like. The expression vectors of the invention can be introduced into host cells to thereby produce proteins or polypeptides, including fusion proteins or polypeptides, encoded by nucleic acids as described herein (e.g., laminin 15 proteins, mutant forms of laminin 15 proteins, fusion proteins, and the like).

The recombinant expression vectors of the invention can be designed for expression of laminin 15 proteins in prokaryotic or eukaryotic cells. For example, polypeptides of the invention can be expressed in *E. coli*, insect cells (e.g., using baculovirus expression vectors), yeast cells or mammalian cells. Suitable host cells are discussed further in Goeddel, *Gene Expression Technology: Methods in Enzymology* 185, Academic Press, San Diego, Calif. (1990). Alternatively, the recombinant expression vector can be transcribed and translated in vitro, for example using T7 promoter regulatory sequences and T7 polymerase.

The laminin 15 expression vector can be a yeast expression vector, a vector for expression in insect cells, e.g., a baculovirus expression vector or a vector suitable for expression in mammalian cells.

When used in mammalian cells, the expression vector's control functions are often provided by viral regulatory elements. For example, commonly used promoters are derived from polyoma, Adenovirus 2, cytomegalovirus and Simian Virus 40.

In another embodiment, the recombinant mammalian expression vector is capable of directing expression of the nucleic acid preferentially in a particular cell type (e.g., tissue-specific regulatory elements are used to express the nucleic acid).

The invention further provides a recombinant expression vector comprising a DNA molecule of the invention cloned into the expression vector in an antisense orientation. Regulatory sequences (e.g., viral promoters and/or enhancers) operatively linked to a nucleic acid cloned in the antisense orientation can be chosen which direct the constitutive, tissue specific or cell type specific expression of antisense RNA in a variety of cell types. The antisense expression vector can be in the form of a recombinant plasmid, phagemid or attenuated virus. For a discussion of the regulation of gene expression using antisense genes see Weintraub, H. et al., Antisense RNA as a molecular tool for genetic analysis, *Reviews—Trends in Genetics*, Vol. 1 (1) 1986.

In another aspect, the invention features, a cell or purified preparation of cells which include one or more exogenously introduced laminin 15 chain nucleic acid, e.g., one or more of an α5 chain, the β2 chain, and/or γ3 chain, or which otherwise misexpress one or more laminin 15 chain. The cell preparation can consist of human or non-human cells, e.g., rodent cells, e.g., mouse or rat cells, rabbit cells, or pig cells. In preferred embodiments, the cell or cells includes one or more of a laminin 15 chain nucleic acid, e.g., a heterologous form of a laminin 15 chain nucleic acid, e.g., a gene derived from humans (in the case of a non-human cell). The laminin 15 chain or chains can be misexpressed, e.g., overexpressed or underexpressed. In other preferred embodiments, the cell or cells include one or more gene(s) which misexpress an endogenous laminin 15 chain, e.g., a gene the expression of which is disrupted, e.g., a knockout. Such cells can serve as a model for studying disorders which are related to mutated or misexpressed laminin 15 chain alleles or for use in drug screening.

In another aspect, the invention features, a human cell, e.g., a hematopoietic stem cell, transformed with nucleic acid which encodes a subject laminin 15 chain polypeptide.

Also provided are cells, preferably human cells, e.g., human hematopoietic or fibroblast cells, in which one or more endogenous laminin 15 chain is under the control of a regulatory sequence that does not normally control the expression of the endogenous laminin 15 chain gene. The expression characteristics of an endogenous gene within a cell, e.g., a cell line or microorganism, can be modified by inserting a heterologous DNA regulatory element into the genome of the cell such that the inserted regulatory element is operably linked to the endogenous laminin 15 chain gene. For example, an endogenous laminin 15 gene which is "transcriptionally silent," e.g., not normally expressed, or expressed only at very low levels, may be activated by inserting a regulatory element which is capable of promoting the expression of a normally expressed gene product in that cell. Techniques such as targeted homologous recombinations, can be used to insert the heterologous DNA as described in, e.g., Chappel, U.S. Pat. No. 5,272,071; WO 91/06667, published in May 16, 1991.

Implants

Implants described herein can be neural implants, e.g., neuromuscular stimulators; auditory prostheses, e.g., speech processors; or retinal implants. Preferred neural implants are retinal implants. Retinal implants can be, e.g., subretinal or epiretinal. Subretinal devices, e.g., MPDAs, are less than 1 cm, e.g., approximately 2 millimeters, in diameter and can be composed of tiny electrodes that are powered by a large number, e.g., 3,500, microscopic solar cells. Subretinal devices include the Optobionics™ silicon chip, in which light coming into the eye both powers the device and is transmitted to the brain as an image by the device. Epiretinal devices can go on top of a damaged retina. A retinal implant can also be a biocompatible device or material designed to carry or deliver a compound or composition to the retina, e.g., an implantable tip, catherer, or tissue; or an electronic device that replaces photoreceptor function, e.g., a phototransistor.

Such implants can be contacted, e.g., coated, with the compositions described herein, e.g., for use in a subject.

Transgenic Animals

The invention provides non-human transgenic animals. Such animals are useful for studying the function and/or activity of laminin 15 and for identifying and/or evaluating modulators of a laminin 15 activity. As used herein, a "transgenic animal" is a non-human animal, preferably a mammal, more preferably a rodent such as a rat or mouse, in which one or more of the cells of the animal includes a transgene. Other examples of transgenic animals include non-human primates, sheep, dogs, cows, goats, chickens, amphibians, and the like. A transgene is exogenous DNA or a rearrangement, e.g., a deletion of endogenous chromosomal DNA, which preferably is integrated into or occurs in the genome of the cells of a transgenic animal. A transgene can direct the expression of an encoded gene product in one or more cell types or tissues of the transgenic animal, other transgenes, e.g., a knockout, reduce expression. Thus, a transgenic animal can be one in which one or more of an endogenous laminin 15 chain gene, e.g., one or more of a α5 chain, the β2 chain, or γ3 chain, has been altered by, e.g., by homologous recombination between the endogenous gene and an exogenous DNA molecule introduced into a cell of the animal, e.g., an embryonic cell of the animal, prior to development of the animal.

EXAMPLES

Example 1

Laminin Expression

Antibodies which recognize the eleven known laminin chains were used to catalog the laminin chains in adult rat and human retina. The reactivity for antibodies directed against each of these chains was assessed using immunohistochemistry (Libby et al., *Invest Ophthalmol Vis Sci* (1996) 37: 1651–1661; Libby et al., *J Comp Neural* (1997) 389: 355–367). Adult rat eyecups were embedded in O.C.T. compound (Miles, Elkhart, Ind.) and frozen by immersion in liquid nitrogen-cooled isopentane. Transverse, 10 pm thick sections, were cut with a Leica cryostat and placed onto Superfrost Plus slides (Fisher, Pittsburgh, Pa.). Human retina specimens were obtained as unfixed transverse sections. Slides were stored at −20° C. until use. For use, slides were returned to room temperature, immersed briefly in acetone (or, interchangeably, for all but the α5,93, and γ2 chains, MeOH) at −20° C., washed in phosphate-buffered saline (PBS; 137 mM NaCl, 2.68 mM KCl, 10 mM $Na_2HPO_4$, 1.76 mM $KH_2PO_4$, pH 7.4), and then incubated in primary antibodies for two hours at room temperature or overnight at 4° C. Primary antibodies were diluted in PBS containing 2% goat serum, or 2% bovine serum albumin, or both. Sections were washed in PBS and incubated in species-appropriate, affinity purified, fluorescently-labeled secondary antibodies diluted in 2% goat serum in PBS for 1 hour at room temperature. Following washes in PBS, slides were mounted in 90% glycerol and 10% water, containing paraphenylenediamine (1 mg/ml; Sigma, St. Louis, Mo.) to reduce photobleaching or in Prolong (Molecular Probes, Eugene, Oreg.). The antibodies used were: laminin 1, cc1 Ply1 (Life Technologies; rabbit polyclonal); laminin cr2 chain (Life Technologies; mouse monoclonal); laminin α3 chain (BM-2, made in one of our laboratories (REB); mouse monoclonal); laminin α4 chain (Miner et al. (1997) *J Cell Biol* 137:685–701; rabbit polyclonal and R17, made in one of our laboratories (REB); rabbit polyclonal), laminin α5 chain (Miner et al. (1995) *J Biol Chem.* 270: 28523–28526; rabbit polyclonal and 4C7, Engvall et al. (1986) *J Cell Biol* 103: 2457–2465; Tiger et al. (1997) *J Biol. Chem.* 272: 28590–28595); laminin β1 chain (C21, Sanes and Chiu, *Cold Spring Harbor Symp. Quant. Biol.* (1983) 48:667–678; mouse monoclonal); laminin β2 chain (GP1, Sanes et al., *J Cell Biol.* (1990) 111:1685–1699; guinea pig polyclonal, C4, Sanes and Chiu, (1983) supra; mouse monoclonal and D5, Hunter et al., *Nature* (1989) 338:229–234; mouse monoclonal); laminin β3 chain (6F12, Rouselle et al. (1991) *J Cell Biol* 114:567–576, mouse monoclonal); laminin γ1 chain (D18, Sanes et al. (1990) supra; mouse monoclonal); laminin γ2 chain (Sugiyama et al. (1995) *Eur. J Biochem.* 228:120–128; rabbit polyclonal); laminin γ3 chain (R16, R21, Koch et al. (1999) *J Cell Biol* 145:605–618; rabbit polyclonals); laminin 5, α3β3γ2 (4101, Rouselle et al. (1991) supra; Marinkovich et al., *J Biol Chem* (1992) 267:17900–17906, 8Ln5 and 9Ln5, made in one of our laboratories (REB); rabbit polyclonals). 8Ln5 and 9Ln5 were made to the same antigen as the published antiserum 4101 and have the same reactivity.

Laminin Alpha Chains

Results showed that a polyclonal antiserum which recognized the three chains of laminin 1 (α1β1γ1) reacted only with the vasculature in the rat and human, and not with the matrix of the neural retina itself. Laminin 1 immunoreactivity was seen on the basal side of the retinal pigmented epithelium, i.e., Bruch's membrane; and in those sections in which the inner limiting membrane was present. Laminin 1 was expressed there as well. These observations suggested that the laminin α1 chain, a component of laminin 1, was not associated with the matrix of either the neural retina or the IPM but was a component of the basement membranes of the retina: Bruch's membrane and the internal limiting membrane.

The laminin α2 chain was also present in the retinal vasculature, but was not detected as being associated with ganglion cell bodies or associated with this basement membrane. The α2 chain does not appear to be a component of Bruch's membrane.

In contrast, the laminin α3 chain was present in the interphotoreceptor matrix, prominent at the external limiting membrane and at the tips of the photoreceptor inner segments. Laminin α3 chain immunoreactivity was also present in the outer plexiform layer. However, in contrast to the chains of laminin 1 and the laminin α2 chain, which were associated with elements of the vasculature in the outer plexiform layer, the laminin α3 chain did not appear to be associated with the larger vessels in this region. Nevertheless, the laminin α3 chain did appear to be present in the outer plexiform layer. It was difficult to discern whether the laminin α3 chain was associated with small vessels or associated with the synaptic connections in this layer. In the human retina, weak immunoreactivity for the laminin α3 chain was also present surrounding cell bodies of the outer and inner nuclear layers. Finally, in human retina, the laminin α3 chain is diffusely associated with the inner plexiform layer.

In contrast to the laminin α1-3 chains, the laminin α4 chain appeared to have a broad distribution in rat and human retina. Immunoreactivity for the laminin α4 chain was present in the IPM, as well as diffusely in both the inner and outer plexiform layers. This extensive immunoreactivity in both plexiform layers, and the lack of any association with the retinal vasculature, suggested that the laminin α4 chain is contained within the extracellular matrix of the plexiform layers. However, the most prominent reactivity for the laminin α4 chain was in what appeared to be Müller cell fibers coursing through the retina. These fibers were confirmed as Muller cell processes, based on co-localization of the laminin α4 chain with a Müller cell marker (vimentin). Reactivity for the laminin α4 chain was also present in the ganglion cell layer which may reflect that laminin α4 chain associated with the endfeet of Müller cells. The presence of the laminin α4 chain within the Müller cell suggested that the Müller cell was a source of the laminin α4 chain in the neural retina, consistent with the data that confirmed the Müller cell as a source of another laminin chain, β2 (Libby et al. (1997) supra).

Our initial localization studies using a polyclonal antiserum raised against the laminin α5 chain (Miner et al. (1995) supra) suggested that the laminin α5 chain was only a component of the true basement membranes of the retina, i.e., the internal limiting membrane, Bruch's membrane, and vascular basement membranes. However, a monoclonal antibody that specifically recognizes the laminin α5 chain (4C7, Engvall et al. (1986) supra; Tiger et al. (1997) supra) demonstrated that the laminin α5 chain is more broadly distributed within the neural retina: the laminin α5 chain had a distribution similar to that for the laminin γ3 chain. Specifically, the laminin α5 chain was present in both rat and human interphotoreceptor matrices, as well as in the outer plexiform layer in the rat. In addition, the laminin α5 chain, like the laminin α1 and α2 chains, was associated with the retinal vasculature. This was particularly notable in the human. Laminin α5 chain immunoreactivity was present in the choroid, the hyaloid vessels, the outer plexiform layer vessels and the vasculature which extends through the retina from the hyaloid vessels to the outer plexiform layer. This expression in the vasculature was similar to the expression pattern for the laminin α5 chain in the brain.

Together, these data suggested that all five laminin α chains were expressed in the retina, but two—the laminin α1 and α2 chains—may be associated exclusively with the retinal vasculature. In contrast to these two laminin u chains, three chains, the laminin α3, α4 and α5 chains, were associated with the IPM and, potentially, associated with the neural retina at synapses in the plexiform layers. Laminins at each of these locations could be provided from the cell that spans the entire thickness of the retina, the Muller cell; the Müller cell is the likely source for at least one other laminin chain, β2 (Libby et al. (1997) *J Comp Neural* 389:355–367).

Laminin Beta Chains

As noted above, a polyclonal serum that recognized all three chains of laminin 1, including the laminin β1 chain, reacted only with the vasculature in rat and human retina. For the human retina, this pattern was consistent with the previously reported expression of laminin 1 (Toti et al. (1997) *Neuromusc Disord* 7:21–25). Thus, the laminin β1 chain was not an element of the matrix of either the IPM or the neural retina. A rat reactive antibody against the β1 chain confirmed this observation. However, as there was little authentic laminin α1 chain in the retina, and little authentic laminin β1 chain in the retinal vasculature of the rat, it was likely that the polyclonal serum against laminin 1 was detecting largely the laminin γ1 chain in the vasculature of both rat and human.

As previously reported in the rat (Libby et al. (1997) supra), the laminin β2 chain was present in the interphotoreceptor matrix, and appeared to be associated with the external limiting membrane. Here, a similar distribution in the human retina was demonstrated. The laminin β2 chain, a known component of brain vasculature, was also associated with the vessels of the retina. In the human, immunoreactivity was also present surrounding cell bodies in the inner nuclear layer, as well as in the inner limiting membrane. In both species, the laminin β2 chain was also diffusely associated with the outer plexiform layer. A comparison of this diffuse immunoreactivity to that for laminin 1 or the laminin α2 chain suggested that the laminin β2 chain was not only associated with the vasculature within the outer plexiform layer. The laminin β2 chain may also be associated with the extracellular matrix of the outer plexiform layer and localized to synapses in the central nervous system, as it is in the peripheral nervous system (Hunter et al. (1989) *Nature* 338:229–234).

Laminin β3 chain immunoreactivity was also present in the mature rat retina, as well as the mature human retina. The β3 chain seems largely limited to the inter-photoreceptor matrix, suggesting that laminins containing the laminin β3 chain are components of this matrix. As laminin β3 has a tightly restricted tissue distribution in rodent (Utani et al. (1995) *Lab Invest* 72: 300–310), and has, so far, only been demonstrated as a component of laminin 5 (α3 β3 γ2), it is likely that this reflects the presence of laminin 5 in the interphotoreceptor matrix.

Together, these data suggested that, although the laminin β1 chain was associated with the basement membrane of the retinal vasculature in both rat and human retina, only two β chains, the laminin β2 and β3 chains, were expressed in the matrix of the IPM. Moreover, the laminin β2 chain was also expressed in the matrix of the outer plexiform layer.

Laminin Gamma Chains

As noted above, a polyclonal serum that recognized all three chains of laminin 1, including the laminin γ1 chain, reacted largely with the vasculature. Consistent with this observation, an antibody directed against the laminin γ1 chain reacted only with the vasculature in both rat and human, suggesting that the anti-laminin 1 serum was reacting with at least the γ1 chain. In addition, in the human, the laminin γ1 chain was present at the internal limiting membrane. This may reflect production by astrocytes, the hyaloid blood vessels, and retinal ganglion cells (Sarthy and Fu (1990) *J Cell Biol* 110: 2099–2108; compare Sarthy, *Vis. Sci.* (1993) 34: 145–152). There was also some punctate immunoreactivity for the laminin γ1 chain within the ganglion cell layer. Importantly, there was no laminin γ1 chain reactivity in the IPM or plexiform layers. Thus, the laminin γ1 chain was confined to the vitread side of the retina.

In contrast to the laminin γ1 chain, the laminin γ2 chain was present in the inter-photoreceptor matrix of rat and human retina. It was also present in the hyaloid vessels, and, to a limited extent, the intraretinal capillaries of the human. Some laminin γ2 chain was also present in the outer plexiform layer of the rat; this immunoreactivity may reflect capillary-associated laminins. As for the laminin β3 chain, previous reports have suggested a restricted distribution of the laminin γ2 chain (Kalhmki et al. (1992) *J Cell Biol* 119:679–693).

The laminin γ3 chain was the most recently isolated of the growing family of laminins (Koch et al. (1999) supra). The tissue distribution of this chain was quite limited. However, it was most extensively expressed in the nervous system.

The results showed the presence of the laminin γ3 chain in a portion of the human and rat central nervous system. Prominent laminin γ3 chain immunoreactivity was present in the interphotoreceptor matrix; notably, throughout the region of photoreceptor inner segments. In addition, there was marked laminin γ3 chain immunoreactivity associated with the external limiting membrane in the rat and surrounding cell bodies within the outer and inner nuclear layers in the human. Finally, the laminin γ3 chain was diffusely present in the outer plexiform layer, at least in the rat. As with the laminin α3, α4, and β2 chains, it cannot be said conclusively that the laminin γ3 chain immunoreactivity in the outer plexiform layer was concentrated at points of synaptic contacts in the outer plexiform layer. However, the laminin γ3 chain was not associated with the vasculature present at the vitread side of the retina, and its pattern of expression was distinct from that. For laminin chains in the vasculature, such as the γ1 chain. Therefore, it was probable that the laminin γ3 chain in the outer plexiform layer was contained within the matrix of the plexiform layer.

Together, these data suggest that the laminin γ2 and γ3 chains were the only known laminin γ chains in the IPM. Furthermore, the laminin γ3 chain appears to be the only laminin γ chain found potentially associated with the synaptic regions of the outer plexiform layer in both rat and human.

Thus, in the IPM, seven laminin chains: α3, α4, α5, β2, 133, γ2 and γ3 were present. This was consistent with the presence of one previously isolated laminin, laminin 5 (α3β3γ2), as well as several novel laminin heterotrimers. If the other chains were to combine, there would be at least two such novel laminin trimers in the IPM: α4β2γ3 and α5β2, γ3. In the matrix of the outer plexiform layer, these two trimers also appear to be present, as their component chains are present. In contrast, only one laminin chain, α4, is prominent in the matrix of the inner plexiform layer, suggesting that other, uncharacterized, β and γ chains may be expressed in the retina.

Example 2

RNA Expression cRNA probes which recognize the RNAs encoding the eleven known laminin chains were used to catalog these RNAs in the retina and to localize them to particular cell types using in situ hybridization. As laminin trimers are assembled prior to secretion, the RNAs encoding all three chains of any given trimer should be present in the same cell.

In situ hybridization was performed as follows. Adult rat eye cups were dissected and fixed overnight at 4° C. in 4% paraformaldehyde in PBS (pH 7.4), dehydrated, and embedded in paraffin. Fifteen micron-thick sections were cut and placed onto Probe-on Plus slides (Fisher). Human retina specimens were obtained as fixed transverse sections. Rehydrated rat sections or frozen human sections were then processed for in situ hybridizations as previously described (Libby et al. (1997) supra).

cRNA probes for the laminin chains were generated as previously described (Libby et al. (1997) supra). Probes for the laminin β1 and β2 chains and for cellular retinaldehyde binding protein were those used previously (Libby et al. (1997) supra). A cRNA probe for the laminin α5 chain (Miner et al. (1995) supra) was generated. cRNAs were labeled during transcription by the incorporation of digoxigenin-UTP (Boehringer Mannheim, Indianapolis, Ind.); 1 µg/ml of cRNA was used for hybridization.

Laminin Alpha Chains

RNAs encoding the laminin α1 and α2 chains were not readily detected in the rat or human retina, suggesting that both of these RNAs were not abundant in the retina. However, for both chains, some RNA was detected in the inner nuclear layer. This may reflect production of these two chains by components of the vasculature.

In contrast, the RNA encoding the laminin α3 chain was readily detectable in the rat and human retina. This expression agrees with the high expression levels of the laminin α3 chain in the retina from the human expressed sequence tag database. Interestingly, laminin α3 chain RNA was not localized to perinuclear sites. Rather, the RNA was in fibers coursing through the inner and outer nuclear layers and the outer plexiform layer. This location was consistent with production of laminin α3 chain RNA by Müller cells.

The RNA encoding the laminin cc4 chain was present in a pattern similar to that encoding the laminin α3 chain. The RNA appeared to be located in fibers coursing through the inner and outer nuclear layers, which were likely to be Müller cell processes. Unlike laminin α3 chain RNA, there did seem to be perinuclear laminin α4 chain RNA in the inner nuclear layer, particularly of the human retina, suggesting that the source of the RNA encoding the laminin α4 chain was a cell whose nucleus resides in the inner nuclear layer. Müller cell nuclei were in this layer. Finally, in human retina, laminin α4 chain RNA was present in the ganglion cell layer, in what was presumed to be Müller cell endfeet.

Similar to the laminin α1 and α2 chain, RNA encoding the laminin α5 chain was not detectable within the rat retina. This suggests that the RNA encoding the laminin α5 chain was not abundant in the rat retina. In an example of species variation, RNA encoding the laminin α5 chain within the human neural retina of the human was detected. The pattern of expression for laminin α5 chain RNA in the human retina was similar to, albeit considerably less intense than, that detected with a probe for laminin α4 chain RNA.

Together, the patterns of expression for the RNAs encoding the laminin α chains suggest that the laminin α3, α4 and α5 chain RNAs were expressed in the neural retina, consistent with the presence of laminin α3, α4 and α5 chain protein noted above. Specifically, they suggested that laminin α3, α4 and α5 chains were produced in the neural retina and deposited in the matrices of the IPM and outer plexiform layer, and, in the case of the laminin α4 chain, the inner plexiform layer.

Laminin Beta Chains

RNA encoding the laminin β1 chain was not highly expressed in the neural retina, as previously reported (Libby et al. (1997) supra). These data were consistent with the lack of laminin β1 chain protein in neural structures within the retina.

It was previously shown that the laminin β2 chain was expressed in the adult rat retina (Libby et al. (1997) supra). RNA encoding the laminin β2 chain was present in fibers in the outer and inner nuclear layers of the rat. In the human retina, RNA encoding the laminin β2 chain was present in what appear to be fibers in the inner and outer nuclear layers. It was striking at the external limiting membrane, and was also present in the ganglion cell layer. It had been previously ascribed that the laminin β2 chain RNA was in the ganglion cell layer to Müller cell endfeet (Libby et al. (1997)). There was also perinuclear RNA present in and around some cell bodies in the inner nuclear layer, suggesting a cell in the inner nuclear layer, possibly the Müller cell, was a source of the laminin β2 chain in the neural retina. Finally, as shown here, for the rat, and here for the human, this pattern of RNA expression was similar to that for cellular retinaldehyde binding protein, an authentic marker of the Müller cell (Bunt-Milam and Saari (1983) *J Cell Biol* 97:703–712).

Laminin β3 chain RNA appears to be expressed in the adult rat retina. RNA encoding the laminin β3 chain was located in fibers coursing through the inner and outer nuclear layers, in the outer plexiform layer, and at the outer limiting membrane. In another example of species variation, laminin β3 chain RNA could not be detected within the human neural retina.

Together, these data suggested that, in both rat and human, the laminin β2 chain was the prominent β chain expressed in the neural retina. In addition, the laminin β3 chain appeared to be a component of the neural retina. Finally, the laminin β1 chain was not likely to be expressed in the mature neural retina.

Laminin Gamma Chains

The RNA encoding the laminin γ1 chain could not be detected in the neural retina. This suggested that the laminin γ1 chain protein in the internal limiting membrane was not derived from the neural retina. The laminin γ1 chain in the internal limiting membrane must, therefore, be derived from one of the non-neural retinal cells that contact it. Both astrocytes and the hyaloid vessels contact the internal limiting membrane and have been suggested as sources for protein components of the internal limiting membrane (Sarthy and Fu (1990) supra; Sarthy (1993) supra).

RNA encoding the laminin γ2 chain was consistently difficult to detect in the retina.

However, the RNA was detectable in the inner nuclear layer of the human retina, and to a lesser extent, the rat retina.

In contrast, RNA encoding the laminin γ3 chain was readily detected in both the rat and human retina. Laminin γ3 chain RNA was expressed in a pattern that is similar to that for several other laminin chain RNAs. In fibers coursing through the outer nuclear layer, at the external limiting membrane, and in presumed Müller cell endfeet in the ganglion cell layer. The γ3 chain was, therefore, a likely y component of mature retinal laminin.

Thus, the expression patterns for the laminin chain RNAs detected in the neural retina demonstrated that RNAs encoding the laminin α3, α4, β2, γ2 and γ3 chains are expressed in the rat and human retina; in addition, RNA encoding the laminin α5 chain was detected in human retina, and that encoding the laminin β3 chain was detected in rat retina. Although slightly different, the basic distribution of all of these RNAs was the same: largely within fibers coursing through the inner and outer nuclear layers. RNAs for the laminin α4 and β2 chains also appear to be present at perinuclear sites in the inner nuclear layer as well as within the ganglion cell layer. Together, these data suggested that the Müller cell is the source of these laminin chain-encoding RNAs. In addition, it supports that the retina produces two novel laminin trimers: laminin 14 (α4β2γ3) and laminin 15 (α5β2γ3).

Example 3

Biochemical Identification of Laminin 14 and 15 in the Retina

The protein and RNA localization data suggested that laminins 5, 14 and 15 were expressed in the neural retina. These findings were extended by isolating laminins, and their component chains, from the retina.

The biochemical isolation of laminin heterotrimers was preformed as follows. Bovine eyes were obtained from Pel-Freez (Rogers, Ark.) and dissected to isolate the retina. About 50 retina were pooled, washed in PBS containing the protease inhibitors phenylmethylsulfonyl fluoride (150 mg/l) and N-ethylmaleimide (650 mg/l), frozen in liquid nitrogen, ground in a Waring blender and resuspended in 100 ml of 2 M urea, 0.5M NaCl, 10 mM EDTA, 1 mM phenylmethylsulfonyl fluoride, 5 mM N-ethylmaleimide, and 50 mM Tris-HCl (pH 7.8), then stirred for 24 hours at 4° C. The retinal extract was cleared by centrifugation at 30,000 g for 60 min, dialyzed in 0.5M NaCl and 50 mM Tris-HCl (PH 7.8), then cleared by centrifugation at 100,000 g for 60 min. Glycoproteins were isolated by applying the extract to a Concanavalin-A-Sepharose column (Pharmacia, Piscataway, N.J.). Unbound material was removed by washing with 0.5M NaCl, 5m. M $CaCl_2$, 5 mM $MgCl_2$ and 50 mM Tris-HCl (pH 7.4). The column was washed with 10 mM α-D-methylmannopyranoside in 0.5 M NaCl and 50 mM Tris-HCl (PH 7.4) and then eluted with 1 M a-D-methylglucopyranoside in 0.5 M NaCl and 50 mM Tris-HCl pH 7.4).

To isolate laminin 14 and laminin 15, the Concanavalin-A eluate was separated without sulfhydryl reduction on a 3–5% polyacrylamide-SDS gel. After staining with Coomassie Brilliant Blue R-250 (Sigma), bands containing the high molecular weight proteins were excised, washed in 0.5 M Tris-HCl pH 6.8), incubated in SDS sample buffer containing 10% P-mercaptoethanol for 30 minutes at ambient temperature, and the different laminin chains were separated on a 5% polyacrylamide-SDS gel. Proteins were analyzed by protein transfer ("Western") blot analysis using an anti-laminin α4 chain antiserum (R17), an anti-laminin β2 chain antibody (D5), and an anti-laminin γ3 chain antiserum (R21).

The 380 kD protein isolated by this method was not reactive with any of the anti-laminin antibodies. Therefore, following digestion by the protease Lys-C, peptide fragments of this protein were sequenced using matrix-assisted laser desorption time-of-flight mass spectrometry (Chait and Kent (1992) *Science* 257:1885–1894) performed on a Finnegan Lasermat 2000.

Although the presence of the laminin α3 chain protein on protein transfer blots of retinal extracts was demonstrated, it has been impossible to isolate any heterotrimeric laminins containing the laminin α3 chain from retinal extracts, and have, therefore, been unable to confirm biochemically the presence of laminins 5 (α3β3γ2) or 13 (α3β2γ3). This may reflect a relative dearth of these trimers in the retina, or a difficulty in extracting them in a native form. However, it has been previously shown that the laminin β2 chain is present in retinal extracts (Hunter et al. (1992) *Neuron* 8:399–413). In addition, laminins eluted from an anti-laminin β2 chain resin contain the α4 chain, demonstrating that the β2 chain is associated with at least this chain in the retina.

Retinal laminins were isolated from retinal matrix by chromatography on Concanavalin A-Sepharose followed by size fractionation on polyacrylamide gels. Two high-molecular weight components were selected from this purification scheme. Each was reduced and separated on polyacrylamide gels. The first (band "A") resolved into components of approximately 190, 220, and 380 kD. Two of these proteins were identified immunologically as the laminin β2 (190 kD) and γ3 (220 kD) chains. The third did not react with any of the anti-laminin antibodies (e.g., anti-α4). The second high molecular weight component (band "B") resolved into components of approximately 190 and 220 kD. The 190 kD component consisted of both the α4 and β2 chains, and the 220 kD component was identified as the γ3 chain. No other chains were detected as components of this complex; therefore, band "B" consists of the novel laminin composed 5 of α4, β2, and γ3 chains, which was term laminin 14.

The high molecular weight of this protein suggested that band "A", was a laminin α chain, perhaps the laminin α5 chain. However, as antibodies did not react with this protein, it was excised from a polyacrylamide gel, digested, and microsequenced. The resultant fragments were compared to known laminin sequences, and all were identical to sequences within the laminin α5 chain (Table One), demonstrating that this third component is the laminin α5 chain. Therefore, band "B" consists of the novel laminin composed of α5, β2, and γ3 chains, which was term laminin 15.

TABLE ONE

| | |
|---|---|
| peptide 1 | AHPVSNAIDGTER (SEQ ID NO:11) |
| mouse laminin α5 (36–48) | AHPVSNAIDGTER (amino acid residues 36–48 of SEQ ID NO:2) |
| peptide 2 | WWQSPPLSR (SEQ ID NO:12) |
| mouse laminin α5 (53–61) | WWQSPPLSR (amino acid residues 49–57 of SEQ ID NO:2) |
| peptide 3 | FANSPRPDLWVLER (SEQ ID NO:13) |
| mouse laminin α5 (83–96) | FANSPRPDLWVLER (amino acid residues 83–96 OF SEQ ID NO:2) |
| peptide 4 | TNTLLGHLMGK (SEQ ID NO:14) |
| mouse laminin α5 (188–198) | TNTLLGHLMGK (amino acid residues 188–198 of SEQ ID NO:2) |
| peptide 5 | FGFNPLEFENFSWR (SEQ ID NO:15) |
| mouse laminin α5 (797–810) | FGFNPLEFENFSWR (amino acid residues 183–826 of SEQ ID NO:2) |

TABLE ONE-continued

| | | |
|---|---|---|
| peptide 6 | | LELEEAATPEGHAVR (SEQ ID NO:16) |
| mouse laminin α5 | (813–827) | LELEEAATPEGHAVR (amino acid residues 798–48 812 of SEQ ID NO:2) |
| peptide 7 | | AGALLPAIR (SEQ ID NO:17) |
| mouse laminin α5 | (2099–2107) | AGALLPAIR (amino acid residues 2100–2108 of SEQ ID NO:2) |
| peptide 8 | | KLIAQAR (SEQ ID NO:18) |
| mouse laminin α5 | (2640–2646) | KLIAQAR (amino acid residues 2640–2646 of SEQ ID NO:2) |

Expression of Laminins 5, 14, and 15 During Retinal Development

It was previously shown that the laminin β2 chain was expressed throughout retinal development (Libby et al. (1996) supra; Libby et al. (1997) supra), at first in the subretinal space, and subsequently in the interphotoreceptor matrix and the outer plexiform layer. In addition, it was recently shown that the laminin β2 chain is critical for proper formation and function of synapses in the outer plexiform layer (Libby et al. (1999) *J Neurosci.* 19: 9399–9411) These observations were extended by examining the expression of potential partners for the laminin β2 chain, i.e., components of laminins 14 and 15, during development of the interphotoreceptor matrix and outer plexiform layer. In the course of these experiments, it was also found that the components of laminin 5 (α3 β3γ2) were expressed in the developing retina. The expression of the components of laminins 14 and 15 were examined, as well as those of laminin 5 (the laminin α3, α4, α5, β2, β3, γ2, and γ3 chains) from postnatal day 0 (P0) through postnatal day 15 (P15). The appearance of these chains was compared with that for two components of the photoreceptor synapse, dystrophins and pdystroglycan.

At P0, few rod photoreceptors have differentiated in the rat retina, and the outer plexiform layer had not yet formed (and, therefore, no dystrophins are present). At this age, the laminin β2 chain is prominently expressed in the subretinal space, as previously reported at E2 1 (Libby et al., 1996, supra), and in fibers spanning the width of the retina, as are the other components of laminins 14 and 15, the laminin α4, α5, and γ3 chains. In addition, the laminin α3, β3, and γ2 chains are also expressed in these locations, and an antiserum against laminin 5 displays similar immunoreactivity. These immunohistochemical data are consistent with the expression of laminins 14 (α4β2γ3), 15 (α5β2γ3), and 5 (α3β3γ2) at P0. However, none of the laminin chains were concentrated in the region that will eventually become the outer plexiform layer.

At P5, the central portion of the retina had begun to elaborate an outer plexiform layer, in which dystrophins were expressed, whereas the peripheral portion had not. At this age, the components of laminins 14 and 15 were still present in the subretinal space and in fibers spanning the thickness of the retina. In addition, in the central portion of the retina, these laminin chains were beginning to be concentrated in the developing outer plexiform layer. Components of laminin 5 remained associated with the subretinal space and in fibers spanning the thickness of the retina. At P10, the entire retina had developed an outer plexiform layer, in which dystrophins were prominently expressed. Interestingly, another component of the adult photoreceptor synapse, β-dystroglycan, was not detectable at this age. The components of laminins 14 and 15 (the α4, α5, β2, and γ3 chains) were concentrated in the developing interphotoreceptor matrix and the outer plexiform layer. In addition, laminin 5 immunoreactivity remained associated with the subretinal space and the outer plexiform layer. In addition, monoclonal antibodies against all three chains of laminin 5 (α3, β3 and γ2) were reactive, suggesting that laminin 5 expression continues.

At P15, the outer plexiform layer was beginning to reach maturity, as judged by the continued presence of dystrophins and now detectable levels of β-dystroglycan. In other respects, the retina at P15 is similar to the adult: the components of laminins 14 and 15, including the laminin α4, β2, and γ3 chains are prominently expressed in the interphotoreceptor matrix and outer plexiform layer, the α4 chain is prominent in fibers spanning the retina, and laminin 5 remains. Expression of one component of the outer plexiform layer, β-dystroglycan, appeared to lag behind the others. By β26, however, the expression closely mimics that of the adult.

In summary, the developing retina contained components of laminins 14 and 15 throughout the period of interphotoreceptor matrix and outer plexiform layer formation. Initially, these chains were expressed in the subretinal space and in fibers spanning the thickness of the retina. With time, they became more restricted to, the interphotoreceptor matrix and outer plexiform layer, reflecting the distribution present in the adult. In addition, components of laminin 5 are expressed in the interphotoreceptor matrix and outer plexiform layer of the developing retina, but become somewhat restricted to the interphotoreceptor matrix by the time a mature morphology is attained. Remarkably, one component of the putative laminin-binding dystrophin complex, β-dystroglycan, is expressed relatively late in retinal synaptogenesis, well after the dystrophins and laminins.

Laminins in the Immunophotoreceptor Matrix (IPM) and Retinal Synaptic Layers

The immunohistochemical studies reported herein, on rat and human retina, show laminin chains α3, α4, α5, β3, γ2, and γ3 surround inner segments, which are likely to reflect a location in the IPM. In the IPM, laminins may be important in maintaining the proper mature environment for photoreceptors. The proposed role for laminins in the IPM, given that laminins are known to be involved in adhesion and that the IPM is thought to be important in retinal adhesion is in retinal adhesion. This is particularly likely for laminin 5, previously shown to be critical for dermal adhesion. It is described herein that photoreceptors can adhere to recombinant laminin β2 chain. It will now be possible to determine whether the heterotrimeric laminins in the IPM are involved in photoreceptor adhesion. Several laminin chains are also present in the mature plexiform layers. In particular, the laminin α3, α4, α5, β2, and γ3 chains were expressed in the outer plexiform layer in a location not likely to be associated with the vasculature.

Müller Cells Produce Retinal Laminins

The RNA encoding the laminin chains that are expressed in the mature neural retina are located in cells that span the retina. This location was consistent with the production of laminins by Müller cells. Muller cell cytoplasm is spread across the retina (Rasmussen (1972) *J Ultrustruct Res* 39:413–429) and RNA is distributed throughout these processes. In addition, it was shown that the distribution of RNA encoding CRALBP, in both rat and human retina (Libby et al. (1997) supra), is similar to that of the laminins: throughout the retina, in fibers coursing through the retinal cell layers. Together with the immunohistochemical data noted above, these data support a Müller cell source for laminins in the IPM and synaptic layers.

Laminins in the Nervous System

In the peripheral nervous system, several cell types produce a variety of laminins. For example, the glial elements that wrap peripheral nerves, Schwann cells, have long been known to produce laminins, including at least one that contains the β2 chain. Conversely, laminins are thought to be important during Schwann cell differentiation. Also in the periphery, muscle cells appear to express several different laminin trimers on their surface, which are likely to be important in guiding innervating motor neurons to their synaptic targets in the muscle, as well as for stabilization of the synapse (Hunter et al. (1989) *Nature* 338:229–234). Importantly, one laminin chain, α2, has been shown to be involved in muscular dystrophies: mutations in α2 have been found in murine muscular dystrophies (Xu et al.,(1994) *Nut Genet* 8:297–302; Sunada et al. (1995) *Hum Mol Genet* 4:1055–1061) and in some cases of a human congenital muscular dystrophy (Helbling-Leclerc et al. (1995) *Nut Genet* 11:216–218).

Similarly, in the central nervous system, laminins are present in a variety of areas, particularly during development. The cellular sources of their component chains include all three major cell classes of the central nervous system: glia, neurons, and neuroglial progenitors. Glial cells, including astrocytes, Bergmann glia, and Müller cells, are thought to be a major source of laminins in the adult and developing CNS (Libby et al. (1997) supra). Neurons may also produce laminins (Sarthy and Fu (1990) *J Cell Biol* 110: 2099–2108). Finally, it has been shown that the retinal neuroglial progenitor may be a source of laminins during development (Libby et al. (1997) supra).

The ability of all of the major neural cell types of the CNS to produce laminins is consistent with the profusion of roles that have been proposed for laminins in the CNS. Most notably, as with laminins in the peripheral nervous system, laminins in the CNS are thought to be involved with axon outgrowth, based upon the laminins known roles in axon outgrowth in vitro (reviewed in Sanes (1989) *Ann Rev Neurosci* 12:491–516; Liesi (1990) *Experientia* 46:900–907) and their distribution along many developing pathways (see, for example, Cohen et al. (1987) *Dev Biol* 22: 407–418; and Liesi and Silver (1988) *Dev Biol* 130:774–785; Zhou (1990) *Dev Brain Res* 55:191–201). Laminins are also thought to be involved with neuronal differentiation in the CNS. For example, it has been shown that retinal laminins containing the β2 chain can promote rod photoreceptor differentiation in vitro (Hunter and Brunken (1997) *Mol Cell Neurosci* 10:7–15). In addition, it has been shown that β2 chain-containing laminins are vital during the differentiation of photoreceptors and their synapses in vivo (Libby et al. (1999) supra).

Novel Laminin Trimers in the Central Nervous System

Retinal basement membranes contain the laminin α1, α5, β1, β2, and γ1 chains. In contrast, the neural retina has a different complement of at least seven laminin chains: α3, α4, α5, β2, β3, γ2 and γ3. Of these, it is probable that the α3, β3, and γ2 chains assemble to form laminin 5, although laminin 5 has not been purified from retinal extracts. However, together with the biochemical data, the expression data suggest that there are at least two novel laminin trimers, laminin 14 (α4 β2 γ3) and laminin 15 (α5 β2 γ3), in the CNS. The apparent loss of the β3 chain in the adult outer plexiform layer suggests that there could be an additional novel laminin present, laminin 13 α3 β2 γ3).

Intriguingly, laminins 14 and 15 appear to be expressed in two locations: (1) within the inter-photoreceptor matrix, and (2) in the outer plexiform layer. The location of these laminins in the outer plexiform layer suggests that they may serve to stabilize retinal synapses, in a manner analogous to that suggested for β2-containing laminins, perhaps including laminin 11, at the neuromuscular junction. Laminins 14 and 15 are the first laminins that could be involved in formation or stabilization of synapses within the CNS. Moreover, these laminins are present at the same location as two components of the dystrophin complex—dystrophins and β-dystroglycan. The ability to examine the presence of all known laminin chains has allowed the demonstration that laminins are, in fact, associated with dystrophin complexes at central synapses, just as they are at the neuromuscular junction. However, as laminin expression precedes that of one component of the dystrophin complex (β-dystroglycan), it seems likely that it is not necessary to assemble the entire complex in order to stabilize laminins at the photoreceptor synapse.

The data describing the presence of laminin 5 during development suggests that this trimer may also be involved in retinal differentiation. This data, along with the data that suggest the presence of laminins 14 and 15 during development, provide support that laminins are critical components of the extracellular environment during differentiation of the nervous system. Laminins are also ubiquitously expressed in the vertebrate nervous system. All patents and references cited herein are incorporated in their entirety by reference. Other embodiments are within the following claims.

What is claimed:

1. An isolated laminin-15, wherein the laminin-15 consists of an α5 chain, a β2 chain, and a γ3 chain.

2. A composition comprising the laminin-15 of claim 1 and a pharmaceutically acceptable carrier.

3. The laminin-15 of claim 1, wherein the laminin-15 is recombinant.

* * * * *

SEQUENCE LISTING

<160> NUMBER OF SEQ ID NOS: 18

<210> SEQ ID NO 1
<211> LENGTH: 11009
<212> TYPE: DNA
<213> ORGANISM: Mus musculus

<400> SEQUENCE: 1

```
gacctctact gcaagctggt tgggggtccg gtggctggcg gagatcccaa tcagacaatc      60
cagggccagt actgtgacat ctgtacagct gccaacagca caaggcaca ccctgtgagc     120
aacgccatcg atggcacgga gcgctggtgg cagagcccac ccctgtcccg tggcctggag     180
tacaatgagg tcaacgtcac actggacctg gccaggtgt tccatgtggc ctatgtgctc     240
atcaagtttg ccaactcacc tcggcctgac ctctgggtgc tggagcggtc cacagacttc     300
ggtcacactt atcagccgtg gcagttcttt gcctcctcca agagggattg tttggagcgg     360
tttggacctc ggactctaga gcgcatcacg caggacgacg acgtcatctg caccacagaa     420
tactcgcgaa tagtgccttt ggagaatggc gagattgtg tgtccttggt aaatgggcgc     480
cctggggcct tgaacttctc ctactcaccg ttacttcgag acttcaccaa agccaccaac     540
atccgcttgc ggtttctgcg aaccaacacg ctactgggcc acctcatggg caaggcgctg     600
cgggaccca cagtcacccg caggtattat tacagcatca agacatcag cattggtggg     660
cgctgtgtct gtcatggcca cgcagatgtc tgtgacgcca aggacccatt ggatcctttc     720
aggctgcagt gtgcctgcca gcacaataca tgtggaggct cttgtgaccg atgctgtcca     780
ggcttcaacc agcagccgtg gaagcccgcc accacggaca cgccaatga gtgccagtcc     840
tgcaattgcc acggccatgc ctacgactgt tactacgacc ctgaggtgga tcggcgcaat     900
gccagccaga accaggacaa cgtgtaccag ggtggaggtg tctgcctgga ttgccagcat     960
cacactacgg gtatcaactg tgagcgttgt ctgcctggct tcttccgtgc ccctgaccag    1020
cctctcgact cacctcatgt ctgtcggccc tgcgactgtg agtcagactt cacggatggg    1080
acctgtgaag acttgacggg ccgctgttac tgcaggccga acttcacagg agagctatgt    1140
gctgcctgcg ctgagggcta cacggacttc ccacactgct accctctgcc ttcatttcct    1200
cacaatgaca cgagagaaca ggtgcttccc gctggacaaa tcgtgaactg tgattgcaat    1260
gctgcaggga cccagggcaa tgcctgccgg aaggacccaa ggttgggacg gtgtgtctgc    1320
aaacccaact tccggggtgc ccactgtgag ctctgtgctc ctggattcca cgggcctagc    1380
tgccaccat gccagtgttc cagccctggg gtagccaaca gctctgtga cccagagtct    1440
ggccagtgca tgtgccgcac cggctttgag ggggacaggt gtgaccactg tgcccttggc    1500
tatttccact tccctctctg tcagctgtgt ggctgcagcc cagcagggac cctgcctgaa    1560
ggctgtgacg aggctggccg ctgccagtgc cgacctggct ttgacggtcc tcactgtgac    1620
cgatgccttc caggatacca tgggtatccc gactgtcacg cttgtgcctg tgaccctcgg    1680
ggggccctgg atcaacagtg tggagtgggc ggtttgtgcc actgccgtcc tggcaacaca    1740
ggtgccactt gtcaggaatg tagccccggc ttctacggct ccccagctg catcccctgc    1800
cactgctctg ccgatggctc cttgcataca acctgtgacc cgacaaccgg ccagtgtagg    1860
tgtcgacccc gagtgacagg actacattgt gatatgtgtg taccaggcgc ctataacttc    1920
ccctactgtg aagctggctc ttgtcatcct gctggtctgg ccccagccaa tcctgcccctt    1980
cctgagacac aggctccctg tatgtgccgg gctcacgtgg aagggccaag ctgtgatcgc    2040
tgtaaacctg ggtactgggg gctgagcgcc agcaaccctg aaggctgcac acgctgcagc    2100
tgtgacccac gaggcacccct gggtggagtt actgagtgcc agggcaatgg gcagtgcttc    2160
tgcaaggctc acgtgtgtgg caagaccgt gcagcctgca aggatggctt ctttggcctg    2220
gattatgctg actactttgg ctgccgtagc tgtaggtgtg atgttggtgg tgccctgggt    2280
```

```
cagggctgtg aaccaaagac aggtgcctgc aggtgccgcc ctaacaccca aggacccacc    2340
tgtagcgagc cagcgaagga ccactacttg ccagacctgc accacatgcg gctggaacta    2400
gaggaggcgg ccactcccga gggccacgct gtacgctttg gcttcaaccc cctggagttt    2460
gagaacttta gctggagagg ctacgcacac atgatggcta tccagcccag gattgtggcc    2520
aggctgaacg tgacctcccc tgacctcttt cgactggttt tccgatatgt caaccgtgga    2580
tcaaccagcg tgaatgggca gatctctgtt cgtgaagagg gcaagctttc cagctgtacc    2640
aactgcacag agcagagcca gccagtggct ttcccaccca gcactgagcc tgcctttgtc    2700
actgtgcccc agagggcctt tggggaaccc tttgtgctga accccggcat ctgggccttg    2760
ctggtcgagc tgaaggtgt actcttggac tacgtggtcc tactgcccag cacctactat    2820
gaggcagctc tcctacagca tcgagtaacg gaggcctgta cctaccgtcc ctcagccctg    2880
cactccacag agaactgtct tgtctatgct cacctccccc tggatggctt cccttcagca    2940
gctggaactg aggccctgtg tcgccatgac aacagcctgc cccggccctg ccccacagag    3000
cagctcagcc cctcacaccc accgctggcg acctgcttcg gcagtgatgt ggacatccag    3060
ctcgagatgg ccgtgcctca gcctggccaa tatgttctcg tggtggaata tgtcggtgag    3120
gattcacacc aagagatggg agtggctgtg cacaccccctc agagagcccc ccagcaaggg    3180
gtgctcaacc tccacccctg cccatacagc tccctgtgcc ggagtccggc tcgggacacc    3240
cagcatcatc tagccatctt ccacctggac tctgaggcta gcatccggct cacagctgag    3300
caagctcact tcttcctgca cagcgtcacc ctggtacctg tggaggagtt cagtactgag    3360
tttgtggagc cccgggtctt ctgtgtgagc agtcatggaa ctttcaaccc cagcagtgct    3420
gcctgtctag cctcccgatt cccgaagcca ccgcagccca tcatccttaa ggactgccag    3480
gtcttgccgc tgcctcccga cctgcctctg actcagtctc aggagctctc accaggtgca    3540 cccccccgagg gaccacagcc tcggccgcca actgcggtgg atcctaatgc agaacccacc    3600
ttgctgcgcc accccagggg cacggtggtc ttcaccaccc aggtgcccac cctgggccgc    3660
tatgccttcc tgctgcacgg ctaccagccg gtccaccccct ccttccctgt ggaggtactc    3720
attaatggtg gccgcatctg gcagggccac gccaacgcca gcttttgtcc tcatggttat    3780
ggctgccgta ccctggtgtt gtgtgagggt cagacgatgc tggatgttac agacaacgag    3840
ctcaccgtga ctgtgcgtgt gccagaaggc cggtggctct ggctggacta cgtactcatt    3900
gtccctgagg atgcttacag ctccagttac ctccaagagg agccctttgga caaatcctat    3960 gacttcatca gccactgtgc cacccagggc taccacatta gccccagcag ctcatctcca    4020
ttctgccgga atgccgccac ctccttgtct ctcttctaca caacgggggc cctcccttgt    4080
ggctgccacg aggtgggtgc cgtaagcccc acgtgcgaac ccttcggggg ccagtgtccc    4140
tgccggggcc acgttattgg ccgtgactgt ccccgctgtg ccaccggcta ctggggtttc    4200
cccaactgca ggccctgtga ctgtggagcc cgcctgtgtg acgagctcac gggccagtgt    4260
atctgtccac cacgcactgt tcccccctgac tgcttggtct gccagccaca gagctttggt    4320
tgccacccct tggtgggctg tgaggagtgt aactgctcag ggcccggcgt ccaggagctg    4380
acggacccta cctgtgacat ggacagcggc cagtgcagat gcagacccaa tgtagctgga    4440
cgtcgctgtg atacctgtgc cccgggcttc tatggctatc ctagctgtcg ccctgtgac     4500 tgccatgagg caggcaccat ggctagcgtg tgtgaccccc tcacaggcca atgccattgc    4560
aaggagaacg tgcagggctc aagatgtgac cagtgtcgcg tggggacctt ctccttggat    4620
gctgctaacc ccaagggctg tacccgctgc ttctgtttcg gggccacaga gcgctgtggg    4680
```

-continued

```
aactctaacc tcgcccgcca tgagttcgtg gacatggagg gctgggtgct gttgagcagt    4740
gaccggcagg tggtacccca cgagcatcgg cctgagatag agctgctgca cgcagatctg    4800
cgctctgtgg ctgacacttt ctcagagctg tactggcagg ctccgccctc ctatctggga    4860
gacagggtgt catcctacgg tggaaccctc cactatgagc tgcactcaga gacccagcga    4920
ggtgatatct tcattcccta cgagagccgg ccggacgtcg tgctgcaggg caaccaaatg    4980
agcatcgcct tcctggaact ggcgtaccct ccgcctggcc aggttcaccg aggacagcta    5040
cagctggtag aggggaactt ccggcacttg agagactcaca accccgtgtc ccgagaagaa    5100
ctcatgatgg tgctggccgg cctggagcag ctgcagatcc gtgctctctt ctcgcagacc    5160
tcttccagtg tctccttgcg tagagtggta ctggaggtgg ctagcgaggc tggtaggggg    5220
cctccagcca gcaatgtgga actgtgtatg tgccctgcca actaccgtgg ggactcgtgc    5280
caggaatgtg ccctggcta ttaccgggac accaagggtc tcttcctagg ccgatgtgtc    5340
ccctgtcagt gccatggcca ttcagatcgc tgccttcctg gctctggcat tgtgtgggc    5400 tgccagcaca acacagaagg ggaccaatgt gagcgctgta ggcctggctt tgtcagcagt    5460
gatcccagta acctgcatc cccatgtgtg agctgccctt gcccttggc agtgccctcc    5520 aataattttg cagacggttg cgtcttaaga aatggccgaa cccagtgcct ctgcaggcca    5580
ggctatgctg gtgcctcctg cgagcggtgt gcacctggct tttttgggaa cccctggtg    5640 ctaggcagct cctgtcagcc ctgcgactgc agcggtaatg gagacccaa catgatcttc    5700 agtgactgcg accccctgac gggtgcctgt cgaggctgcc tccgtcacac cactgggccc    5760
cactgtgaac gctgtgcccc aggcttctat ggcaatgctt tgttgccagg caactgcacc    5820
cggtgtgact gttccccatg tgggacagaa acctgtgatc cccagagtgg acgctgcctg    5880
tgcaaagcag gcgtgactgg acaacgttgt gaccgctgtt tggaaggata cttcggtttt    5940
gagcaatgcc agggctgccg cccttgtgcc tgtggaccag ctgccaaggg ctccgagtgc    6000
caccctcaga gcggtcagtg tcactgccag ccagggacca caggacccca gtgcctcgag    6060
tgcgcccctg gctactgggg cctcccagag aagggctgca ggcgctgcca gtgtcccga    6120 ggccactgtg acccacacac gggccactgc acctgtcccc cggggctcag cggggaacgc    6180
tgtgacacct gcagccagca gcaccaggtg cctgtaccgg gcaagcctgg gggccatggc    6240
atacactgtg aagtgtgtga ccactgtgtg gttctccttc tggatgacct cgagcgggct    6300
ggtgccctcc tccccgctat ccgtgagcag ctgcagggta tcaatgccag ctccgcggcc    6360
tgggccaggc tgcacaggct gaatgcctcc attgctgacc tgcagagtaa actccggagg    6420
ccaccgggac cccgctacca gcagcacag cagctacaga ctctagagca gcagagtata    6480
agccttcaac aggacacgga gaggctgggc agtcaggcca cagggtccaa ggtcaggca    6540 ggccagctac tggacaccac agagtccaca ctgggccggg cacagaagtt gttggagtct    6600
gtgcgagctg tgggccgtgc cctgaatgag ctggcatctc gcatgggcca aggatctcca    6660
ggcgatgcct tggtaccgtc tggcgagcag ctgcgctggg ctctggctga agtggagcgg    6720
ctgctctggg atatgcggac gcgtgacctg ggggcccagg gggcagtggc agaggccgaa    6780
ctggccgaag cccagaggct gatggctcgt gtccaggagc agctgaccag cttctgggag    6840
gagaaccagt cattggccac acacattcgg gaccagctgg ctcagtatga gtctggcctc    6900
atggatcttc gtgaggccct gaaccaggcc gttaatacca cccggaggc tgaggaactc    6960 aacagccgca accaggaacg ggtgaaggaa gccctgcaat ggaaacagga actgtcccag    7020
```

```
gacaatgcca ccctgaaggc cactcttcaa gctgccagtc tcatcttggg ccatgtttct    7080
gagcttctgc agggcataga ccaggctaag gaggacctag agcacctggc ggccagcctg    7140
gatggagcct ggacacccc tt actgaagagg atgcaggcct tttccctgc cagcagcaag    7200 gtggacttgg tagaggctgc tgaggcccac gctcagaagc tgaaccagct ggcaatcaac    7260
ctgtctggca tcatccttgg catcaatcag gaccgcttca tccagagggc tgtggaagcc    7320
tccaatgcct acagcagcat ccttcaggcc gttcaggctg ccgaggatgc ggcaggccag    7380
gcactgaggc aggccagccg cacatgggag atggtggtgc agcggggcct agcagctgga    7440
gcccggcagc tgttagccaa cagcagtgcc ctggaggaga ccatccttgg acaccagggg    7500
aggctgggcc ttgctcaggg ccgtctgcag gctgcgggga tccagcttca taatgtctgg    7560
gccaggaaga accagctagc agcccagatc caggaggcac aagccatgct ggccatggac    7620
acgagcgaga ccagtgagaa gattgctcac gccaaggctg tggctgccga agccctcagt    7680
acggccaccc acgtgcagtc tcagcttcag ggtatgcaga agaatgtgga gaggtggcag    7740
agccagctgg gaggcctgca aggccaggac ctgagccagg tggaacggga tgcaagcagt    7800
tcagtgtcca ccctggagaa gacattgcca cagctgctgg ccaaactgag ccgtctagag    7860
aaccgtggag ttcacaatgc cagcctggct ttgtctgcca acattggtcg tgtgcgcaag    7920
ctcattgccc aagcccggag tgccgccagc aaggtcaagg tgtccatgaa gttcaatggg    7980
cgttcagggg tacgactgcg tcccccacga gaccttgccg accttgctgc gtacactgcc    8040
ctcaagttcc acatccagag cccagtgcca gcgcccgaac ctggcaagaa cacggggga c    8100 cactttgttc tgtacatggg cagccgccag gccactgggg actacatggg agtgtctctg    8160
cgtaatcaga aggtgcactg ggtgtacagg ctaggaaagg ctggcccca c aactctcagc    8220 atcgacgaga catcgggga gcagtttgca gccgtcagca tcgacaggac cctccagttt    8280
ggccacatgt ctgtcaccgt ggagaaacag atggttcatg atcaagggg a gacacggtg    8340 gcccctggga gcgagggact actcaacctg catcctgacg attttgtctt ctacgtggga    8400
ggataccccc gcaacttcac gcccctgaa ccctccgat tccctggcta cctgggctgc    8460
attgagatgg aaacactgaa tgaggaggtg gtcagcctct acaattttga gcagaccttc    8520
atgctggaca cggcagtaga taaaccttgt gctcgctcca aggccaccgg tgacccatgg    8580
ctcacagatg gctcctacct ggatggcagt ggctttgccc gcatcagctt tgagaagcag    8640
ttcagcaaca caaaacgctt tgaccaggag ctgcggcttg tgtcctacaa tgggatcatc    8700 ttttcctca agcaagagag ccagttcttg tgcctggcag tgcaggaagg caccctggtg    8760
ctcttctatg acttcggctc tggcctgaag aaggccgacc cactgcagcc cccacaagcc    8820
ttgacggcag ccagcaaggc gatccaagtg tttctattgg ctggcaatcg caaacgtgtg    8880
ttggtgcgtg tggagcgggc cactgtgttc agcgtagacc aggataacat gctggagatg    8940
gctgatgcct actacttggg aggdgtgcca cctgaacagc tgcccttgag cctacggcag    9000 ctcttccct ccggaggctc tgtccgtggy tgcatcaagg gtattaaggc tctgggcaag    9060
tacgtggacc tcaaacggtt gaacaccacg ggcatcagtt tcggctgcac cgctgacctg    9120
ctagtgggac gcaccatgac ttttcacggc cacggcttcc tgcccctggc acttcctgat    9180
gtggcaccca tcaccgaagt ggtctattct ggctttggct ttcgtggcac ccaggacaac    9240
aacctgctgt attaccgtac ctccccggat gggccgtacc aggtatccct gagggagggc    9300
cacgtgacac tccgttttat gaaccaagag gtggaaactc aaagggtctt tgctgatggt    9360
gctcctcact atgttgcctt ctatagcaat gtcacagggg tatggctgta tgtggatgac    9420
```

```
cagctacaac tagtaaagtc tcatgagaga caaactccca tgctccaact acagcccgag    9480
gaaccctcac ggcttctcct gggaggcctg cctgtgtctg gtaccttcca caacttcagt    9540
ggctgcatca gcaatgtttt tgtacagcga cttcggggac cacagcgtgt gtttgaccta    9600
caccagaaca tggggagtgt caatgtaagc gtaggctgta caccagccca actcatcgag    9660
acctcaaggg ccacggctca gaaggtttcc cgccgtagtc gacaacccag ccaggacctt    9720
gcctgcacga caccctggct ccctgggact attcaggatg cataccagtt tggggga ccc    9780 ctgcccagtt acctacagtt tgtgggtatc tctccgtccc acaggaatag ctccacctc    9840 tccatgcttg tccgtccaca tgcggcttcc cagggcctcc tgctctctac agccccatg    9900 tcgggccgca gcccttcgtt ggtactcttt ctaaaccatg acactttgt cgcacagact    9960 gagggccctg gccccggct ccaggtccag agtcgccagc actcacgggc tggccagtgg   10020
cacagggtgt ccgtccgctg gggaatgcag cagatccagc ttgtggtgga cggcagccag   10080
acctggagcc agaaggctct ccaccatcgg gtccccaggg cagagcgacc acagccctac   10140
accctctctg taggaggtct tcctgccagc agttacagtt ccaagctccc tgtgtctgtg   10200
gggttcagcg gctgtctgaa gaaattacag ctggataagc agccactgag gaccccaacg   10260
caaatggtgg gggtcacacc ctgtgtctca ggccccctgg aagatggcct gttcttccca   10320
ggcagtgagg gagttgtcac attagagctc cccaaggcca agatgcccta tgtgagcctg   10380
gagctagaga tgcggcccct tggcagctgct ggcctcatct tccacctggg ccaggccctg   10440
gccactccct acatgcagct gaaggtgctg acagaacagg tcctgctgca ggcaaatgat   10500
ggggcagggg agttttccac gtgggtgacc taccccaagc tttgtgatgg acggtggcac   10560
cgagtggcag tgatcatggg cagggacaca ctccggctgg aggtagacac acagagcaac   10620
cacaccacag gccgtttgcc agagagcttg gctggttctc cagcacttct gcacctcggg   10680
agcctgccca gtcttcaac tgctcggcca gagctccctg cctaccgagg atgcttgagg   10740
aagctgctga tcaatggggc ccctgtcaac gtgactgctt ctgtacaaat ccaggggggca   10800 gtggggatgc gcggatgccc ctcaggaacc ctagcacttt ccaagcaggg aaaggcactg   10860
acccagaggc acgccaagcc cagtgtctcc ccgctacttt ggcattgagg gttcccagac   10920
cttggggttt gcctacactt tctatgaata acaagtcatt tctggttac actgtcttt    10980 agaggaaaag gactctgtag aacagatat                                     11009
```

<210> SEQ ID NO 2
<211> LENGTH: 3635
<212> TYPE: PRT
<213> ORGANISM: Mus musculus

<400> SEQUENCE: 2

Asp Leu Tyr Cys Lys Leu Val Gly Gly Pro Val Ala Gly Gly Asp Pro
1               5                   10                  15

Asn Gln Thr Ile Gln Gly Gln Tyr Cys Asp Ile Cys Thr Ala Ala Asn
            20                  25                  30

Ser Asn Lys Ala His Pro Val Ser Asn Ala Ile Asp Gly Thr Glu Arg
        35                  40                  45

Trp Trp Gln Ser Pro Pro Leu Ser Arg Gly Leu Glu Tyr Asn Glu Val
    50                  55                  60

Asn Val Thr Leu Asp Leu Gly Gln Val Phe His Val Ala Tyr Val Leu
65                  70                  75                  80

Ile Lys Phe Ala Asn Ser Pro Arg Pro Asp Leu Trp Val Leu Glu Arg

-continued

```
                85                  90                  95
Ser Thr Asp Phe Gly His Thr Tyr Gln Pro Trp Gln Phe Ala Ser
                    100                 105                 110
Ser Lys Arg Asp Cys Leu Glu Arg Phe Gly Pro Arg Thr Leu Glu Arg
            115                 120                 125
Ile Thr Gln Asp Asp Val Ile Cys Thr Thr Glu Tyr Ser Arg Ile
        130                 135                 140
Val Pro Leu Glu Asn Gly Glu Ile Val Val Ser Leu Val Asn Gly Arg
145                 150                 155                 160
Pro Gly Ala Leu Asn Phe Ser Tyr Ser Pro Leu Leu Arg Asp Phe Thr
                165                 170                 175
Lys Ala Thr Asn Ile Arg Leu Arg Phe Leu Arg Thr Asn Thr Leu Leu
            180                 185                 190
Gly His Leu Met Gly Lys Ala Leu Arg Asp Pro Thr Val Thr Arg Arg
        195                 200                 205
Tyr Tyr Tyr Ser Ile Lys Asp Ile Ser Ile Gly Gly Arg Cys Val Cys
        210                 215                 220
His Gly His Ala Asp Val Cys Asp Ala Lys Asp Pro Leu Asp Pro Phe
225                 230                 235                 240
Arg Leu Gln Cys Ala Cys Gln His Asn Thr Cys Gly Gly Ser Cys Asp
                245                 250                 255
Arg Cys Cys Pro Gly Phe Asn Gln Pro Trp Lys Pro Ala Thr Thr
            260                 265                 270
Asp Ser Ala Asn Glu Cys Gln Ser Cys Asn Cys His Gly His Ala Tyr
        275                 280                 285
Asp Cys Tyr Tyr Asp Pro Glu Val Asp Arg Arg Asn Ala Ser Gln Asn
        290                 295                 300
Gln Asp Asn Val Tyr Gln Gly Gly Val Cys Leu Asp Cys Gln His
305                 310                 315                 320
His Thr Thr Gly Ile Asn Cys Glu Arg Cys Leu Pro Gly Phe Phe Arg
                325                 330                 335
Ala Pro Asp Gln Pro Leu Asp Ser Pro His Val Cys Arg Pro Cys Asp
            340                 345                 350
Cys Glu Ser Asp Phe Thr Asp Gly Thr Cys Glu Asp Leu Thr Gly Arg
        355                 360                 365
Cys Tyr Cys Arg Pro Asn Phe Thr Gly Glu Leu Cys Ala Ala Cys Ala
        370                 375                 380
Glu Gly Tyr Thr Asp Phe Pro His Cys Tyr Pro Leu Pro Ser Phe Pro
385                 390                 395                 400
His Asn Asp Thr Arg Glu Gln Val Leu Pro Ala Gly Gln Ile Val Asn
                405                 410                 415
Cys Asp Cys Asn Ala Ala Gly Thr Gln Gly Asn Ala Cys Arg Lys Asp
            420                 425                 430
Pro Arg Leu Gly Arg Cys Val Cys Lys Pro Asn Phe Arg Gly Ala His
        435                 440                 445
Cys Glu Leu Cys Ala Pro Gly Phe His Gly Pro Ser Cys His Pro Cys
        450                 455                 460
Gln Cys Ser Ser Pro Gly Val Ala Asn Ser Leu Cys Asp Pro Glu Ser
465                 470                 475                 480
Gly Gln Cys Met Cys Arg Thr Gly Phe Glu Gly Asp Arg Cys Asp His
                485                 490                 495
Cys Ala Leu Gly Tyr Phe His Phe Pro Leu Cys Gln Leu Cys Gly Cys
            500                 505                 510
```

-continued

```
Ser Pro Ala Gly Thr Leu Pro Glu Gly Cys Asp Glu Ala Gly Arg Cys
        515                 520                 525

Gln Cys Arg Pro Gly Phe Asp Gly Pro His Cys Asp Arg Cys Leu Pro
    530                 535                 540

Gly Tyr His Gly Tyr Pro Asp Cys His Ala Cys Ala Cys Asp Pro Arg
545                 550                 555                 560

Gly Ala Leu Asp Gln Gln Cys Gly Val Gly Leu Cys His Cys Arg
                565                 570                 575

Pro Gly Asn Thr Gly Ala Thr Cys Gln Glu Cys Ser Pro Gly Phe Tyr
                580                 585                 590

Gly Phe Pro Ser Cys Ile Pro Cys His Cys Ser Ala Asp Gly Ser Leu
                595                 600                 605

His Thr Thr Cys Asp Pro Thr Thr Gly Gln Cys Arg Cys Arg Pro Arg
610                 615                 620

Val Thr Gly Leu His Cys Asp Met Cys Val Pro Gly Ala Tyr Asn Phe
625                 630                 635                 640

Pro Tyr Cys Glu Ala Gly Ser Cys His Pro Ala Gly Leu Ala Pro Ala
                645                 650                 655

Asn Pro Ala Leu Pro Glu Thr Gln Ala Pro Cys Met Cys Arg Ala His
                660                 665                 670

Val Glu Gly Pro Ser Cys Asp Arg Cys Lys Pro Gly Tyr Trp Gly Leu
                675                 680                 685

Ser Ala Ser Asn Pro Glu Gly Cys Thr Arg Cys Ser Cys Asp Pro Arg
                690                 695                 700

Gly Thr Leu Gly Gly Val Thr Glu Cys Gln Gly Asn Gly Gln Cys Phe
705                 710                 715                 720

Cys Lys Ala His Val Cys Gly Lys Thr Cys Ala Ala Cys Lys Asp Gly
                725                 730                 735

Phe Phe Gly Leu Asp Tyr Ala Asp Tyr Phe Gly Cys Arg Ser Cys Arg
                740                 745                 750

Cys Asp Val Gly Gly Ala Leu Gly Gln Gly Cys Glu Pro Lys Thr Gly
                755                 760                 765

Ala Cys Arg Cys Arg Pro Asn Thr Gln Gly Pro Thr Cys Ser Glu Pro
    770                 775                 780

Ala Lys Asp His Tyr Leu Pro Asp Leu His His Met Arg Leu Glu Leu
785                 790                 795                 800

Glu Glu Ala Ala Thr Pro Glu Gly His Ala Val Arg Phe Gly Phe Asn
                805                 810                 815

Pro Leu Glu Phe Glu Asn Phe Ser Trp Arg Gly Tyr Ala His Met Met
    820                 825                 830

Ala Ile Gln Pro Arg Ile Val Ala Arg Leu Asn Val Thr Ser Pro Asp
        835                 840                 845

Leu Phe Arg Leu Val Phe Arg Tyr Val Asn Arg Gly Ser Thr Ser Val
    850                 855                 860

Asn Gly Gln Ile Ser Val Arg Glu Glu Gly Lys Leu Ser Ser Cys Thr
865                 870                 875                 880

Asn Cys Thr Glu Gln Ser Gln Pro Val Ala Phe Pro Pro Ser Thr Glu
                885                 890                 895

Pro Ala Phe Val Thr Val Pro Gln Arg Gly Phe Gly Glu Pro Phe Val
                900                 905                 910

Leu Asn Pro Gly Ile Trp Ala Leu Leu Val Glu Ala Glu Gly Val Leu
    915                 920                 925
```

-continued

```
Leu Asp Tyr Val Val Leu Leu Pro Ser Thr Tyr Tyr Glu Ala Ala Leu
    930                 935                 940

Leu Gln His Arg Val Thr Glu Ala Cys Thr Tyr Arg Pro Ser Ala Leu
945                 950                 955                 960

His Ser Thr Glu Asn Cys Leu Val Tyr Ala His Leu Pro Leu Asp Gly
                965                 970                 975

Phe Pro Ser Ala Ala Gly Thr Glu Ala Leu Cys Arg His Asp Asn Ser
            980                 985                 990

Leu Pro Arg Pro Cys Pro Thr Glu Gln Leu Ser Pro Ser His Pro Pro
        995                 1000                1005

Leu Ala Thr Cys Phe Gly Ser Asp Val Asp Ile Gln Leu Glu Met Ala
    1010                1015                1020

Val Pro Gln Pro Gly Gln Tyr Val Leu Val Glu Tyr Val Gly Glu
1025                1030                1035                1040

Asp Ser His Gln Glu Met Gly Val Ala Val His Thr Pro Gln Arg Ala
                1045                1050                1055

Pro Gln Gln Gly Val Leu Asn Leu His Pro Cys Pro Tyr Ser Ser Leu
            1060                1065                1070

Cys Arg Ser Pro Ala Arg Asp Thr Gln His His Leu Ala Ile Phe His
        1075                1080                1085

Leu Asp Ser Glu Ala Ser Ile Arg Leu Thr Ala Glu Gln Ala His Phe
    1090                1095                1100

Phe Leu His Ser Val Thr Leu Val Pro Val Glu Glu Phe Ser Thr Glu
1105                1110                1115                1120

Phe Val Glu Pro Arg Val Phe Cys Val Ser Ser His Gly Thr Phe Asn
                1125                1130                1135

Pro Ser Ser Ala Ala Cys Leu Ala Ser Arg Phe Pro Lys Pro Pro Gln
            1140                1145                1150

Pro Ile Ile Leu Lys Asp Cys Gln Val Leu Pro Leu Pro Pro Asp Leu
        1155                1160                1165

Pro Leu Thr Gln Ser Gln Glu Leu Ser Pro Gly Ala Pro Pro Glu Gly
    1170                1175                1180

Pro Gln Pro Arg Pro Pro Thr Ala Val Asp Pro Asn Ala Glu Pro Thr
1185                1190                1195                1200

Leu Leu Arg His Pro Gln Gly Thr Val Val Phe Thr Thr Gln Val Pro
                1205                1210                1215

Thr Leu Gly Arg Tyr Ala Phe Leu Leu His Gly Tyr Gln Pro Val His
            1220                1225                1230

Pro Ser Phe Pro Val Glu Val Leu Ile Asn Gly Gly Arg Ile Trp Gln
        1235                1240                1245

Gly His Ala Asn Ala Ser Phe Cys Pro His Gly Tyr Gly Cys Arg Thr
    1250                1255                1260

Leu Val Leu Cys Glu Gly Gln Thr Met Leu Asp Val Thr Asp Asn Glu
1265                1270                1275                1280

Leu Thr Val Thr Val Arg Val Pro Glu Gly Arg Trp Leu Trp Leu Asp
                1285                1290                1295

Tyr Val Leu Ile Val Pro Glu Asp Ala Tyr Ser Ser Ser Tyr Leu Gln
            1300                1305                1310

Glu Glu Pro Leu Asp Lys Ser Tyr Asp Phe Ile Ser His Cys Ala Thr
        1315                1320                1325

Gln Gly Tyr His Ile Ser Pro Ser Ser Ser Pro Phe Cys Arg Asn
    1330                1335                1340

Ala Ala Thr Ser Leu Ser Leu Phe Tyr Asn Asn Gly Ala Leu Pro Cys
```

-continued

```
          1345                1350                1355                1360

Gly Cys His Glu Val Gly Ala Val Ser Pro Thr Cys Glu Pro Phe Gly
                    1365                1370                1375

Gly Gln Cys Pro Cys Arg Gly His Val Ile Gly Arg Asp Cys Ser Arg
                    1380                1385                1390

Cys Ala Thr Gly Tyr Trp Gly Phe Pro Asn Cys Arg Pro Cys Asp Cys
                    1395                1400                1405

Gly Ala Arg Leu Cys Asp Glu Leu Thr Gly Gln Cys Ile Cys Pro Pro
                    1410                1415                1420

Arg Thr Val Pro Pro Asp Cys Leu Val Cys Gln Pro Gln Ser Phe Gly
   1425                1430                1435                1440

Cys His Pro Leu Val Gly Cys Glu Glu Cys Asn Cys Ser Gly Pro Gly
                    1445                1450                1455

Val Gln Glu Leu Thr Asp Pro Thr Cys Asp Met Asp Ser Gly Gln Cys
                    1460                1465                1470

Arg Cys Arg Pro Asn Val Ala Gly Arg Arg Cys Asp Thr Cys Ala Pro
                    1475                1480                1485

Gly Phe Tyr Gly Tyr Pro Ser Cys Arg Pro Cys Asp Cys His Glu Ala
                    1490                1495                1500

Gly Thr Met Ala Ser Val Cys Asp Pro Leu Thr Gly Gln Cys His Cys
   1505                1510                1515                1520

Lys Glu Asn Val Gln Gly Ser Arg Cys Asp Gln Cys Arg Val Gly Thr
                    1525                1530                1535

Phe Ser Leu Asp Ala Ala Asn Pro Lys Gly Cys Thr Arg Cys Phe Cys
                    1540                1545                1550

Phe Gly Ala Thr Glu Arg Cys Gly Asn Ser Asn Leu Ala Arg His Glu
                    1555                1560                1565

Phe Val Asp Met Glu Gly Trp Val Leu Leu Ser Ser Asp Arg Gln Val
                    1570                1575                1580

Val Pro His Glu His Arg Pro Glu Ile Glu Leu Leu His Ala Asp Leu
   1585                1590                1595                1600

Arg Ser Val Ala Asp Thr Phe Ser Glu Leu Tyr Trp Gln Ala Pro Pro
                    1605                1610                1615

Ser Tyr Leu Gly Asp Arg Val Ser Ser Tyr Gly Gly Thr Leu His Tyr
                    1620                1625                1630

Glu Leu His Ser Glu Thr Gln Arg Gly Asp Ile Phe Ile Pro Tyr Glu
                    1635                1640                1645

Ser Arg Pro Asp Val Val Leu Gln Gly Asn Gln Met Ser Ile Ala Phe
                    1650                1655                1660

Leu Glu Leu Ala Tyr Pro Pro Gly Gln Val His Arg Gly Gln Leu
   1665                1670                1675                1680

Gln Leu Val Glu Gly Asn Phe Arg His Leu Glu Thr His Asn Pro Val
                    1685                1690                1695

Ser Arg Glu Glu Leu Met Met Val Leu Ala Gly Leu Glu Gln Leu Gln
                    1700                1705                1710

Ile Arg Ala Leu Phe Ser Gln Thr Ser Ser Val Ser Leu Arg Arg
                    1715                1720                1725

Val Val Leu Glu Val Ala Ser Glu Ala Gly Arg Gly Pro Pro Ala Ser
   1730                1735                1740

Asn Val Glu Leu Cys Met Cys Pro Ala Asn Tyr Arg Gly Asp Ser Cys
   1745                1750                1755                1760

Gln Glu Cys Ala Pro Gly Tyr Tyr Arg Asp Thr Lys Gly Leu Phe Leu
                    1765                1770                1775
```

-continued

```
Gly Arg Cys Val Pro Cys Gln Cys His Gly His Ser Asp Arg Cys Leu
            1780                1785                1790
Pro Gly Ser Gly Ile Cys Val Gly Cys Gln His Asn Thr Glu Gly Asp
        1795                1800                1805
Gln Cys Glu Arg Cys Arg Pro Gly Phe Val Ser Ser Asp Pro Ser Asn
    1810                1815                1820
Pro Ala Ser Pro Cys Val Ser Cys Pro Cys Pro Leu Ala Val Pro Ser
1825                1830                1835                1840
Asn Asn Phe Ala Asp Gly Cys Val Leu Arg Asn Gly Arg Thr Gln Cys
            1845                1850                1855
Leu Cys Arg Pro Gly Tyr Ala Gly Ala Ser Cys Glu Arg Cys Ala Pro
        1860                1865                1870
Gly Phe Phe Gly Asn Pro Leu Val Leu Gly Ser Ser Cys Gln Pro Cys
    1875                1880                1885
Asp Cys Ser Gly Asn Gly Asp Pro Asn Met Ile Phe Ser Asp Cys Asp
        1890                1895                1900
Pro Leu Thr Gly Ala Cys Arg Gly Cys Leu Arg His Thr Thr Gly Pro
1905                1910                1915                1920
His Cys Glu Arg Cys Ala Pro Gly Phe Tyr Gly Asn Ala Leu Leu Pro
            1925                1930                1935
Gly Asn Cys Thr Arg Cys Asp Cys Ser Pro Cys Gly Thr Glu Thr Cys
        1940                1945                1950
Asp Pro Gln Ser Gly Arg Cys Leu Cys Lys Ala Gly Val Thr Gly Gln
        1955                1960                1965
Arg Cys Asp Arg Cys Leu Glu Gly Tyr Phe Gly Phe Glu Gln Cys Gln
    1970                1975                1980
Gly Cys Arg Pro Cys Ala Cys Gly Pro Ala Ala Lys Gly Ser Glu Cys
1985                1990                1995                2000
His Pro Gln Ser Gly Gln Cys His Cys Gln Pro Gly Thr Thr Gly Pro
            2005                2010                2015
Gln Cys Leu Glu Cys Ala Pro Gly Tyr Trp Gly Leu Pro Glu Lys Gly
        2020                2025                2030
Cys Arg Arg Cys Gln Cys Pro Arg Gly His Cys Asp Pro His Thr Gly
    2035                2040                2045
His Cys Thr Cys Pro Pro Gly Leu Ser Gly Glu Arg Cys Asp Thr Cys
2050                2055                2060
Ser Gln Gln His Gln Val Pro Val Pro Gly Lys Pro Gly Gly His Gly
2065                2070                2075                2080
Ile His Cys Glu Val Cys Asp His Cys Val Val Leu Leu Asp Asp
            2085                2090                2095
Leu Glu Arg Ala Gly Ala Leu Leu Pro Ala Ile Arg Glu Gln Leu Gln
        2100                2105                2110
Gly Ile Asn Ala Ser Ser Ala Ala Trp Ala Arg Leu His Arg Leu Asn
        2115                2120                2125
Ala Ser Ile Ala Asp Leu Gln Ser Lys Leu Arg Arg Pro Pro Gly Pro
    2130                2135                2140
Arg Tyr Gln Ala Ala Gln Gln Leu Gln Thr Leu Glu Gln Gln Ser Ile
2145                2150                2155                2160
Ser Leu Gln Gln Asp Thr Glu Arg Leu Gly Ser Gln Ala Thr Gly Val
            2165                2170                2175
Gln Gly Gln Ala Gly Gln Leu Leu Asp Thr Thr Glu Ser Thr Leu Gly
        2180                2185                2190
```

```
Arg Ala Gln Lys Leu Leu Glu Ser Val Arg Ala Val Gly Arg Ala Leu
        2195                2200                2205

Asn Glu Leu Ala Ser Arg Met Gly Gln Gly Ser Pro Gly Asp Ala Leu
        2210                2215                2220

Val Pro Ser Gly Glu Gln Leu Arg Trp Ala Leu Ala Glu Val Glu Arg
2225                2230                2235                2240

Leu Leu Trp Asp Met Arg Thr Arg Asp Leu Gly Ala Gln Gly Ala Val
            2245                2250                2255

Ala Glu Ala Glu Leu Ala Glu Ala Gln Arg Leu Met Ala Arg Val Gln
            2260                2265                2270

Glu Gln Leu Thr Ser Phe Trp Glu Glu Asn Gln Ser Leu Ala Thr His
        2275                2280                2285

Ile Arg Asp Gln Leu Ala Gln Tyr Glu Ser Gly Leu Met Asp Leu Arg
        2290                2295                2300

Glu Ala Leu Asn Gln Ala Val Asn Thr Thr Arg Glu Ala Glu Glu Leu
2305                2310                2315                2320

Asn Ser Arg Asn Gln Glu Arg Val Lys Glu Ala Leu Gln Trp Lys Gln
            2325                2330                2335

Glu Leu Ser Gln Asp Asn Ala Thr Leu Lys Ala Thr Leu Gln Ala Ala
            2340                2345                2350

Ser Leu Ile Leu Gly His Val Ser Glu Leu Leu Gln Gly Ile Asp Gln
        2355                2360                2365

Ala Lys Glu Asp Leu Glu His Leu Ala Ala Ser Leu Asp Gly Ala Trp
        2370                2375                2380

Thr Pro Leu Leu Lys Arg Met Gln Ala Phe Ser Pro Ala Ser Ser Lys
2385                2390                2395                2400

Val Asp Leu Val Glu Ala Ala Glu Ala His Ala Gln Lys Leu Asn Gln
            2405                2410                2415

Leu Ala Ile Asn Leu Ser Gly Ile Ile Leu Gly Ile Asn Gln Asp Arg
            2420                2425                2430

Phe Ile Gln Arg Ala Val Glu Ala Ser Asn Ala Tyr Ser Ser Ile Leu
        2435                2440                2445

Gln Ala Val Gln Ala Ala Glu Asp Ala Ala Gly Gln Ala Leu Arg Gln
        2450                2455                2460

Ala Ser Arg Thr Trp Glu Met Val Val Gln Arg Gly Leu Ala Ala Gly
2465                2470                2475                2480

Ala Arg Gln Leu Leu Ala Asn Ser Ser Ala Leu Glu Glu Thr Ile Leu
            2485                2490                2495

Gly His Gln Gly Arg Leu Gly Leu Ala Gln Gly Arg Leu Gln Ala Ala
        2500                2505                2510

Gly Ile Gln Leu His Asn Val Trp Ala Arg Lys Asn Gln Leu Ala Ala
        2515                2520                2525

Gln Ile Gln Glu Ala Gln Ala Met Leu Ala Met Asp Thr Ser Glu Thr
        2530                2535                2540

Ser Glu Lys Ile Ala His Ala Lys Ala Val Ala Ala Glu Ala Leu Ser
2545                2550                2555                2560

Thr Ala Thr His Val Gln Ser Gln Leu Gln Gly Met Gln Lys Asn Val
            2565                2570                2575

Glu Arg Trp Gln Ser Gln Leu Gly Gly Leu Gln Gly Asp Leu Ser
            2580                2585                2590

Gln Val Glu Arg Asp Ala Ser Ser Val Ser Thr Leu Glu Lys Thr
        2595                2600                2605

Leu Pro Gln Leu Leu Ala Lys Leu Ser Arg Leu Glu Asn Arg Gly Val
```

-continued

```
            2610                2615                2620
His Asn Ala Ser Leu Ala Leu Ser Ala Asn Ile Gly Arg Val Arg Lys
2625                2630                2635                2640

Leu Ile Ala Gln Ala Arg Ser Ala Ser Lys Val Lys Val Ser Met
            2645                2650                2655

Lys Phe Asn Gly Arg Ser Gly Val Arg Leu Arg Pro Pro Arg Asp Leu
            2660                2665                2670

Ala Asp Leu Ala Ala Tyr Thr Ala Leu Lys Phe His Ile Gln Ser Pro
            2675                2680                2685

Val Pro Ala Pro Glu Pro Gly Lys Asn Thr Gly Asp His Phe Val Leu
            2690                2695                2700

Tyr Met Gly Ser Arg Gln Ala Thr Gly Asp Tyr Met Gly Val Ser Leu
2705                2710                2715                2720

Arg Asn Gln Lys Val His Trp Val Tyr Arg Leu Gly Lys Ala Gly Pro
            2725                2730                2735

Thr Thr Leu Ser Ile Asp Glu Asn Ile Gly Glu Gln Phe Ala Ala Val
            2740                2745                2750

Ser Ile Asp Arg Thr Leu Gln Phe Gly His Met Ser Val Thr Val Glu
            2755                2760                2765

Lys Gln Met Val His Glu Ile Lys Gly Asp Thr Val Ala Pro Gly Ser
            2770                2775                2780

Glu Gly Leu Leu Asn Leu His Pro Asp Asp Phe Val Phe Tyr Val Gly
2785                2790                2795                2800

Gly Tyr Pro Ser Asn Phe Thr Pro Pro Glu Pro Leu Arg Phe Pro Gly
            2805                2810                2815

Tyr Leu Gly Cys Ile Glu Met Glu Thr Leu Asn Glu Glu Val Val Ser
            2820                2825                2830

Leu Tyr Asn Phe Glu Gln Thr Phe Met Leu Asp Thr Ala Val Asp Lys
            2835                2840                2845

Pro Cys Ala Arg Ser Lys Ala Thr Gly Asp Pro Trp Leu Thr Asp Gly
            2850                2855                2860

Ser Tyr Leu Asp Gly Ser Gly Phe Ala Arg Ile Ser Phe Glu Lys Gln
2865                2870                2875                2880

Phe Ser Asn Thr Lys Arg Phe Asp Gln Glu Leu Arg Leu Val Ser Tyr
            2885                2890                2895

Asn Gly Ile Ile Phe Phe Leu Lys Gln Glu Ser Gln Phe Leu Cys Leu
            2900                2905                2910

Ala Val Gln Glu Gly Thr Leu Val Leu Phe Tyr Asp Phe Gly Ser Gly
            2915                2920                2925

Leu Lys Lys Ala Asp Pro Leu Gln Pro Pro Gln Ala Leu Thr Ala Ala
            2930                2935                2940

Ser Lys Ala Ile Gln Val Phe Leu Leu Ala Gly Asn Arg Lys Arg Val
2945                2950                2955                2960

Leu Val Arg Val Glu Arg Ala Thr Val Phe Ser Val Asp Gln Asp Asn
            2965                2970                2975

Met Leu Glu Met Ala Asp Ala Tyr Tyr Leu Gly Gly Val Pro Pro Glu
            2980                2985                2990

Gln Leu Pro Leu Ser Leu Arg Gln Leu Phe Pro Ser Gly Gly Ser Val
            2995                3000                3005

Arg Gly Cys Ile Lys Gly Ile Lys Ala Leu Gly Lys Tyr Val Asp Leu
            3010                3015                3020

Lys Arg Leu Asn Thr Thr Gly Ile Ser Phe Gly Cys Thr Ala Asp Leu
3025                3030                3035                3040
```

-continued

Leu Val Gly Arg Thr Met Thr Phe His Gly His Gly Phe Leu Pro Leu
            3045                3050                3055

Ala Leu Pro Asp Val Ala Pro Ile Thr Glu Val Val Tyr Ser Gly Phe
            3060                3065                3070

Gly Phe Arg Gly Thr Gln Asp Asn Asn Leu Leu Tyr Tyr Arg Thr Ser
            3075                3080                3085

Pro Asp Gly Pro Tyr Gln Val Ser Leu Arg Glu Gly His Val Thr Leu
            3090                3095                3100

Arg Phe Met Asn Gln Glu Val Glu Thr Gln Arg Val Phe Ala Asp Gly
3105                3110                3115                3120

Ala Pro His Tyr Val Ala Phe Tyr Ser Asn Val Thr Gly Val Trp Leu
            3125                3130                3135

Tyr Val Asp Asp Gln Leu Gln Leu Val Lys Ser His Glu Arg Thr Thr
            3140                3145                3150

Pro Met Leu Gln Leu Gln Pro Glu Glu Pro Ser Arg Leu Leu Leu Gly
            3155                3160                3165

Gly Leu Pro Val Ser Gly Thr Phe His Asn Phe Ser Gly Cys Ile Ser
            3170                3175                3180

Asn Val Phe Val Gln Arg Leu Arg Gly Pro Gln Arg Val Phe Asp Leu
3185                3190                3195                3200

His Gln Asn Met Gly Ser Val Asn Val Ser Val Gly Cys Thr Pro Ala
            3205                3210                3215

Gln Leu Ile Glu Thr Ser Arg Ala Thr Ala Gln Lys Val Ser Arg Arg
            3220                3225                3230

Ser Arg Gln Pro Ser Gln Asp Leu Ala Cys Thr Thr Pro Trp Leu Pro
            3235                3240                3245

Gly Thr Ile Gln Asp Ala Tyr Gln Phe Gly Gly Pro Leu Pro Ser Tyr
            3250                3255                3260

Leu Gln Phe Val Gly Ile Ser Pro Ser His Arg Asn Arg Leu His Leu
3265                3270                3275                3280

Ser Met Leu Val Arg Pro His Ala Ala Ser Gln Gly Leu Leu Leu Ser
            3285                3290                3295

Thr Ala Pro Met Ser Gly Arg Ser Pro Ser Leu Val Leu Phe Leu Asn
            3300                3305                3310

His Gly His Phe Val Ala Gln Thr Glu Gly Pro Gly Pro Arg Leu Gln
            3315                3320                3325

Val Gln Ser Arg Gln His Ser Arg Ala Gly Gln Trp His Arg Val Ser
            3330                3335                3340

Val Arg Trp Gly Met Gln Gln Ile Gln Leu Val Val Asp Gly Ser Gln
3345                3350                3355                3360

Thr Trp Ser Gln Lys Ala Leu His His Arg Val Pro Arg Ala Glu Arg
            3365                3370                3375

Pro Gln Pro Tyr Thr Leu Ser Val Gly Gly Leu Pro Ala Ser Ser Tyr
            3380                3385                3390

Ser Ser Lys Leu Pro Val Ser Val Gly Phe Ser Gly Cys Leu Lys Lys
            3395                3400                3405

Leu Gln Leu Asp Lys Gln Pro Leu Arg Thr Pro Thr Gln Met Val Gly
            3410                3415                3420

Val Thr Pro Cys Val Ser Gly Pro Leu Glu Asp Gly Leu Phe Phe Pro
3425                3430                3435                3440

Gly Ser Glu Gly Val Val Thr Leu Glu Leu Pro Lys Ala Lys Met Pro
            3445                3450                3455

```
Tyr Val Ser Leu Glu Leu Glu Met Arg Pro Leu Ala Ala Gly Leu
        3460                3465                3470

Ile Phe His Leu Gly Gln Ala Leu Ala Thr Pro Tyr Met Gln Leu Lys
        3475                3480                3485

Val Leu Thr Glu Gln Val Leu Leu Gln Ala Asn Asp Gly Ala Gly Glu
        3490                3495                3500

Phe Ser Thr Trp Val Thr Tyr Pro Lys Leu Cys Asp Gly Arg Trp His
3505                3510                3515                3520

Arg Val Ala Val Ile Met Gly Arg Asp Thr Leu Arg Leu Glu Val Asp
                3525                3530                3535

Thr Gln Ser Asn His Thr Thr Gly Arg Leu Pro Glu Ser Leu Ala Gly
        3540                3545                3550

Ser Pro Ala Leu Leu His Leu Gly Ser Leu Pro Lys Ser Ser Thr Ala
        3555                3560                3565

Arg Pro Glu Leu Pro Ala Tyr Arg Gly Cys Leu Arg Lys Leu Leu Ile
        3570                3575                3580

Asn Gly Ala Pro Val Asn Val Thr Ala Ser Val Gln Ile Gly Ala
3585                3590                3595                3600

Val Gly Met Arg Gly Cys Pro Ser Gly Thr Leu Ala Leu Ser Lys Gln
                3605                3610                3615

Gly Lys Ala Leu Thr Gln Arg His Ala Lys Pro Ser Val Ser Pro Leu
        3620                3625                3630

Leu Trp His
        3635

<210> SEQ ID NO 3
<211> LENGTH: 3141
<212> TYPE: DNA
<213> ORGANISM: Homo sapiens

<400> SEQUENCE: 3 tcagggtgc agctgcgcac cccacgggat cttgccgacc ttgctgccta cactgccctc      60
aagttctacc tgcagggccc agagcctgag cctgggcagg gtaccgagga tcgctttgtg    120
atgtacatgg gcagccgcca ggccactggg gactacatgg gtgtgtctct gcgtgacaag    180
aaggtgcact gggtgtatca gctgggtgag gcgggccctg cagtcctaag catcgatgag    240
gacattgggg agcagttcgc agctgtcagc ctggacagga ctctccagtt tggccacatg    300
tccgtcacag tggagagaca gatgatccag gaaaccaagg gtgacacggt ggcccctggg    360 gcagagggc tgctcaacct gcggccagac gacttcgtct tctacgtcgg ggggtacccc    420
agtaccttca cgcccctcc cctgcttcgc ttccccggct accggggctg catcgagatg    480
gacacgctga atgaggaggt ggtcagcctc tacaacttcg agaggacctt ccagctggac    540
acggctgtgg acaggccttg tgcccgctcc aagtcgaccg ggacccgtg gctcacggac    600 ggctcctacc tggacggcac cggcttcgcc cgcatcagct cgacagtca gatcagcacc    660 accaagcgct tcgagcagga gctgcggctc gtgtcctaca gcggggtgct cttcttcctg    720
aagcagcaga gccagttcct gtgcttggcc gtgcaagaag gcagcctcgt gctgttgtat    780
gactttgggg ctggcctgaa aaaggccgtc ccactgcagc ccaccgcc cctgacctcg    840 gccagcaagg cgatccaggt gttcctgctg ggggcagcc gcaagcgtgt gctggtgcgt    900
gtggagcggg ccacggtgta cagcgtggag caggacaatg atctggagct ggccgacgcc    960
tactacctgg ggccgtgcc gcccgaccag ctgccccga gcctgcgatg gctcttcccc   1020
accggaggct cagtccgtgg ctgcgtcaaa ggcatcaagg ccctgggcaa gtatgtggac   1080
```

```
ctcaagcggc tgaacacgac aggcgtgagc gccggctgca ccgccgacct gctggtgggg    1140
cgcgccatga ctttccatgg ccacggcttc cttcgcctgg cgctctcgaa cgtggcaccg    1200
ctcactggca acgtctactc cggcttcggc ttccacagcg cccaggacag tgccctgctc    1260
tactaccggg cgtccccgga tgggctatgc caggtgtccc tgcagcaggg ccgtgtgagc    1320
ctacagctcc tgaggactga agtgaaaact caagcgggct cgccgatgg tgcccccat     1380
tacgtcgcct tctacagcaa tgccacggga gtctggctgt atgtcgatga ccagctccag    1440
cagatgaagc cccaccgggg accaccccc gagctccagc cgcagcctga ggggcccccg    1500
aggctcctcc tgggaggcct gcctgagtct ggcaccattt acaacttcag tggctgcatc    1560
agcaacgtct tcgtgcagcg gctcctgggc ccacagcgcg tatttgatct gcagcagaac    1620
ctgggcagcg tcaatgtgag cacgggctgt gcaccgccc tgcaagccca ccccgggc      1680
ctggggccta gaggactgca ggccaccgcc cggaaggcct cccgccgcag ccgtcagccc    1740
gcccggcatc ctgcctgcat gctgccccca cacctcagga ccacccgaga ctcctaccag    1800
tttgggggtt ccctgtccag tcacctggag tttgtgggca tcctggcccg acataggaac    1860
tggcccagtc tctccatgca cgtcctcccg cgaagctccc gaggcctcct cctcttcact    1920
gcccgtctga ggcccggcag cccctccctg gcgctcttcc tgagcaatgg ccacttcgtt    1980
gcacagatgg aaggcctcgg gactcggctc cgcgcccaga gccgccagcg ctcccggcct    2040
ggccgctggc acaaggtctc cgtgcgctgg gagaagaacc ggatcctgct ggtgacggac    2100
ggggcccggg cctggagcca ggaggggccg caccggcagc caggggggc agagcacccc    2160
cagccccaca ccctctttgt gggcggcctc ccggccagca gccacagctc caaacttccg    2220
gtgaccgtcg ggttcagcgg ctgtgtgaag agactgaggc tgcacgggag gcccctgggg    2280
gcccccacac ggatggcagg ggtcacaccc tgcatcttgg gcccctgga ggcgggcctg     2340
ttcttcccag gcagcggggg agttatcact ttagacctcc caggagctac actgcctgat    2400
gtgggcctgg aactggaggt gcggcccctg gcagtcaccg gactgatctt ccacttgggc    2460
caggcccgga cgccccccta cttgcagttg caggtgaccg agaagcaagt cctgctgcgg    2520
gcggatgacg gagcagggga gttctccacg tcagtgaccc gcccctcagt gctgtgtgat    2580
ggccagtggc accggctagc ggtgatgaaa gcgggaatg tgctccggct ggaggtggac    2640
gcgcagagca accacaccgt gggccccttg ctggcggctg cagctggtgc cccagcccct    2700
ctgtacctcg ggggcctgcc tgagcccatg gccgtgcagc cctggccccc cgcctactgc    2760
ggctgcatga ggaggctggc ggtgaaccgg tccccgtcg ccatgactcg ctctgtggag     2820
gtccacgggg cagtgggggc cagtggctgc ccagccgcct aggacacagc caaccccggc    2880
ccctggtcag gccctgcag ctgcctcaca ccgccccttg tgctcgcctc ataggtgtct     2940
atttggactc taagctctac gggtgacaga tcttgtttct gaagatggtt taagttatag    3000
cttcttaaac gaaagaataa aatactgcaa aatgttttta tatttggccc ttccacccat    3060
ttttaattgt gagagatttg tcaccaatca tcactggttc ctccttaaaa attaaaaagt    3120
aacttctgtg taaaaaaaaa a                                              3141
```

<210> SEQ ID NO 4
<211> LENGTH: 953
<212> TYPE: PRT
<213> ORGANISM: Homo sapiens

<400> SEQUENCE: 4

```
Ser Gly Val Gln Leu Arg Thr Pro Arg Asp Leu Ala Asp Leu Ala Ala
  1               5                  10                  15

Tyr Thr Ala Leu Lys Phe Tyr Leu Gln Gly Pro Glu Pro Glu Pro Gly
             20                  25                  30

Gln Gly Thr Glu Asp Arg Phe Val Met Tyr Met Gly Ser Arg Gln Ala
         35                  40                  45

Thr Gly Asp Tyr Met Gly Val Ser Leu Arg Asp Lys Lys Val His Trp
 50                  55                  60

Val Tyr Gln Leu Gly Glu Ala Gly Pro Ala Val Leu Ser Ile Asp Glu
 65                  70                  75                  80

Asp Ile Gly Glu Gln Phe Ala Ala Val Ser Leu Asp Arg Thr Leu Gln
                 85                  90                  95

Phe Gly His Met Ser Val Thr Val Glu Arg Gln Met Ile Gln Glu Thr
                100                 105                 110

Lys Gly Asp Thr Val Ala Pro Gly Ala Glu Gly Leu Leu Asn Leu Arg
            115                 120                 125

Pro Asp Asp Phe Val Phe Tyr Val Gly Gly Tyr Pro Ser Thr Phe Thr
130                 135                 140

Pro Pro Pro Leu Leu Arg Phe Pro Gly Tyr Arg Gly Cys Ile Glu Met
145                 150                 155                 160

Asp Thr Leu Asn Glu Glu Val Val Ser Leu Tyr Asn Phe Glu Arg Thr
                165                 170                 175

Phe Gln Leu Asp Thr Ala Val Asp Arg Pro Cys Ala Arg Ser Lys Ser
            180                 185                 190

Thr Gly Asp Pro Trp Leu Thr Asp Gly Ser Tyr Leu Asp Gly Thr Gly
            195                 200                 205

Phe Ala Arg Ile Ser Phe Asp Ser Gln Ile Ser Thr Thr Lys Arg Phe
210                 215                 220

Glu Gln Glu Leu Arg Leu Val Ser Tyr Ser Gly Val Leu Phe Phe Leu
225                 230                 235                 240

Lys Gln Gln Ser Gln Phe Leu Cys Leu Ala Val Gln Glu Gly Ser Leu
            245                 250                 255

Val Leu Leu Tyr Asp Phe Gly Ala Gly Leu Lys Lys Ala Val Pro Leu
            260                 265                 270

Gln Pro Pro Pro Leu Thr Ser Ala Ser Lys Ala Ile Gln Val Phe
            275                 280                 285

Leu Leu Gly Gly Ser Arg Lys Arg Val Leu Val Arg Val Glu Arg Ala
            290                 295                 300

Thr Val Tyr Ser Val Glu Gln Asp Asn Asp Leu Glu Leu Ala Asp Ala
305                 310                 315                 320

Tyr Tyr Leu Gly Gly Val Pro Pro Asp Gln Leu Pro Pro Ser Leu Arg
                325                 330                 335

Trp Leu Phe Pro Thr Gly Gly Ser Val Arg Gly Cys Val Lys Gly Ile
            340                 345                 350

Lys Ala Leu Gly Lys Tyr Val Asp Leu Lys Arg Leu Asn Thr Thr Gly
            355                 360                 365

Val Ser Ala Gly Cys Thr Ala Asp Leu Leu Val Gly Arg Ala Met Thr
370                 375                 380

Phe His Gly His Gly Phe Leu Arg Leu Ala Leu Ser Asn Val Ala Pro
385                 390                 395                 400

Leu Thr Gly Asn Val Tyr Ser Gly Phe Gly Phe His Ser Ala Gln Asp
                405                 410                 415

Ser Ala Leu Leu Tyr Tyr Arg Ala Ser Pro Asp Gly Leu Cys Gln Val
```

-continued

```
            420                 425                 430
Ser Leu Gln Gln Gly Arg Val Ser Leu Gln Leu Leu Arg Thr Glu Val
        435                 440                 445
Lys Thr Gln Ala Gly Phe Ala Asp Gly Ala Pro His Tyr Val Ala Phe
450                 455                 460
Tyr Ser Asn Ala Thr Gly Val Trp Leu Tyr Val Asp Asp Gln Leu Gln
465                 470                 475                 480
Gln Met Lys Pro His Arg Gly Pro Pro Glu Leu Gln Pro Gln Pro
                485                 490                 495
Glu Gly Pro Pro Arg Leu Leu Leu Gly Gly Leu Pro Glu Ser Gly Thr
                500                 505                 510
Ile Tyr Asn Phe Ser Gly Cys Ile Ser Asn Val Phe Val Gln Arg Leu
        515                 520                 525
Leu Gly Pro Gln Arg Val Phe Asp Leu Gln Gln Asn Leu Gly Ser Val
        530                 535                 540
Asn Val Ser Thr Gly Cys Ala Pro Ala Leu Gln Ala Gln Thr Pro Gly
545                 550                 555                 560
Leu Gly Pro Arg Gly Leu Gln Ala Thr Ala Arg Lys Ala Ser Arg Arg
                565                 570                 575
Ser Arg Gln Pro Ala Arg His Pro Ala Cys Met Leu Pro Pro His Leu
                580                 585                 590
Arg Thr Thr Arg Asp Ser Tyr Gln Phe Gly Gly Ser Leu Ser Ser His
                595                 600                 605
Leu Glu Phe Val Gly Ile Leu Ala Arg His Arg Asn Trp Pro Ser Leu
        610                 615                 620
Ser Met His Val Leu Pro Arg Ser Ser Arg Gly Leu Leu Leu Phe Thr
625                 630                 635                 640
Ala Arg Leu Arg Pro Gly Ser Pro Ser Leu Ala Leu Phe Leu Ser Asn
                645                 650                 655
Gly His Phe Val Ala Gln Met Glu Gly Leu Gly Thr Arg Leu Arg Ala
                660                 665                 670
Gln Ser Arg Gln Arg Ser Arg Pro Gly Arg Trp His Lys Val Ser Val
        675                 680                 685
Arg Trp Glu Lys Asn Arg Ile Leu Leu Val Thr Asp Gly Ala Arg Ala
690                 695                 700
Trp Ser Gln Glu Gly Pro His Arg Gln His Gly Ala Glu His Pro
705                 710                 715                 720
Gln Pro His Thr Leu Phe Val Gly Leu Pro Ala Ser Ser His Ser
                725                 730                 735
Ser Lys Leu Pro Val Thr Val Gly Phe Ser Gly Cys Val Lys Arg Leu
                740                 745                 750
Arg Leu His Gly Arg Pro Leu Gly Ala Pro Thr Arg Met Ala Gly Val
        755                 760                 765
Thr Pro Cys Ile Leu Gly Pro Leu Glu Ala Gly Leu Phe Phe Pro Gly
770                 775                 780
Ser Gly Gly Val Ile Thr Leu Asp Leu Pro Gly Ala Thr Leu Pro Asp
785                 790                 795                 800
Val Gly Leu Glu Leu Glu Val Arg Pro Leu Ala Val Thr Gly Leu Ile
                805                 810                 815
Phe His Leu Gly Gln Ala Arg Thr Pro Pro Tyr Leu Gln Leu Gln Val
                820                 825                 830
Thr Glu Lys Gln Val Leu Leu Arg Ala Asp Asp Gly Ala Gly Glu Phe
        835                 840                 845
```

-continued

```
Ser Thr Ser Val Thr Arg Pro Ser Val Leu Cys Asp Gly Gln Trp His
    850                 855                 860

Arg Leu Ala Val Met Lys Ser Gly Asn Val Leu Arg Leu Glu Val Asp
865                 870                 875                 880

Ala Gln Ser Asn His Thr Val Gly Pro Leu Leu Ala Ala Ala Gly
                885                 890                 895

Ala Pro Ala Pro Leu Tyr Leu Gly Gly Leu Pro Glu Pro Met Ala Val
                900                 905                 910

Gln Pro Trp Pro Pro Ala Tyr Cys Gly Cys Met Arg Arg Leu Ala Val
            915                 920                 925

Asn Arg Ser Pro Val Ala Met Thr Arg Ser Val Glu Val His Gly Ala
    930                 935                 940

Val Gly Ala Ser Gly Cys Pro Ala Ala
945                 950
```

<210> SEQ ID NO 5
<211> LENGTH: 5957
<212> TYPE: DNA
<213> ORGANISM: Mus musculus
<220> FEATURE:
<221> NAME/KEY: misc_feature
<222> LOCATION: (1)...(5957)
<223> OTHER INFORMATION: n = A,T,C or G

<400> SEQUENCE: 5

```
aaagggcctc gagcttccaa gtaatctttg cttgatctcc aagagtctgt catagcgtgg      60
cactcaaacg aagccgtacg acctgaacca acctcttccg cctgttgtcc agggtctgg     120
gtggnnngcg cctagtgggt gcgcgcattc caaccctcgc tcccgggctg ccaggcgact    180
ggaaagtccg gcgtggataa atagtcacaa gattcggatt cacttgttgc tggtggtcca    240
gagtctgtca cccagaaccc atcctctggg taactgagta gccacagccc attttaatca    300
ggaaacaggc aacctttctc gcaacccatt tgctggagtg cttatggacg gtcgagttcc    360
tcggagttct gtttcaggca gtagtgcgtg gcctttccag tatctccgag agctcagtcc    420
tagtctatcc tttgggcgtc ctaaaccttt ccacaggtac aatagaattc tagcttgcac    480
ctttcccatc catctcccga ctgatgctgt aaccctggga gccccgcggc tgatttgtgg    540
tttccatagt gacaccagga caaaggccat aagctccttc catctgcctt cctgatacac    600
aaagatcaca aacctctcga tttacctctg ccacccgcca actccacgag ccctcttcct    660
gtcccctgaa tgccatgctt gccagcaacc cctggttcac atcgggactt aagggatccg    720
atgaagatat gtggaccagg atgctctgtc tttgagcagc ctactctaat ttcttttttgg    780
atgctcccctt ttagttcctc gaactaagct gcttctttgc taagtacaca tctgctaaat    840
aaacttcagc ttaaaagaa agtggatgaa gtaaccaaag tctggttctt aggatgaggg    900
ttgtctgcag cgggcagggg tatggtaggg grtgggtgc tatcctcagt tataatccta    960
ttttagatcc actccgtgtt ttacttcctt cccttgcttt ccaactttac tcaaagtcgt   1020
cagagtctct cagattgtgg aggagtgact gctaggtccg accctggaca gattgagggc   1080
ctggagggac accagcccag tacccacacg gtcgggtcag catcagcccc aaggaggtg    1140
gtgggctttc gtctgtggac tctttatctc tctttatctc tattttactt ttcttcagga   1200
tggagtgggc ctcaggagaa ccagggaggg gcaggcaggg acagcctttg ccatgggaac   1260
ttcgcttggg cctacttcta agtggtgagg gggcctggtg aggcctaagg ttgtgggatg   1320
tgatggtagg tccagggggtg gcaggctgtt cccaggggcc caaggggtgg ggctagtcac   1380
```

```
caggagtcct gctgagctga ttgacccact gtcctcagtg ctggctgcca cattggccca    1440
ggccccgtcc ttggatgtac ctggctgttc tcgaggaagc tgctatccag ccaccggtga    1500
cctgttggtg ggccgtgcgg acagactgac ggcctcatcc acgtgtggct tgcatagccc    1560
tcaaccctac tgtattgtca gtcacctgca ggtgcttctg gggccccaga ggagagggct    1620
gggtcagggt ggggtcggcc ccagctaagg tacctatcct acactccacc caatccagga    1680
cgaaaagaag tgtttcctgt gtgactcccg acgtcccttc tctgctcgag acaacccaaa    1740
tagtcatcgg atccagaatg tagtcaccag ctttgcgcca caacgccgga cggcctggtg    1800
gcaatcggag aacggtgagc ccctgagtag gtcatcagga tgactagggc ttgtaaccag    1860
taaccgcaga accttgaccc cctattcctg ctgcaggggt tccaatggtc accatccaac    1920
tggacctgga agctgagttt catttcaccc acctcattat gacgttcaag gtgcctgtgc    1980
gtcagcgaac ccgcctgatt tgctttgct tctcagtacc ccctaacaga gtcctagctc    2040
tacaacgaag cttccctgag ctcctgtgtt gtgctctatg tgtgaagcat ggtcacgtcc    2100
tgcatggctt ccatagttga acacctctgc acatgtctc ttgtgcccca ttcctaggct    2160
aagtcagata cagtctctct gggtctcgtg gtattttaac ctgcctgtca gaggtggctg    2220
tcctccctgg tctgatcatg gtctggcttt cctagtcttt cccatgtgtc tgagatgctc    2280
agcagtgatc atgactaagc agagctctcc gtaacctagg ctggactgaa gtctggttcc    2340
tgctagtcag acatgtcctc cttccccatc cagacgttcc ggcctgctgc tatgctggtg    2400
gagcgttctg cagactttgg ccgcacctgg cacgtgtacc gatatttttc ctatgactgc    2460
ggggctgact tcccgggaat cccactggcc ccgccacgtc gctgggatga tgtagtgtgt    2520
gagtcccgct actcagaaat cgagccgtct acggaaggcg aggtaagggc tgggacccag    2580
ctagtggggt ctgtgatgga cgtggacgag gttcattatc tgtggacttc ttgccctgct    2640
aggtcatcta tcgtgtgctg gaccctgcta ttcccatccc agaccctacagctcacgga    2700 ttcagagtga gtgttctact atggacattg gcacagtctc agtgtccgga tgggactatt    2760
tggggcctca gtaactattt taggtgcttc ctagggcaaa tgccaagccc agtttagctc    2820
tgggagcaat agaaaagagg tctcccaagg tgaccttggc agctgcaacc aatggtggca    2880
ctggtgggga cgaggcaaca aggggccacc tgcttagttg gacgagaccc tcttcccttt    2940
cttagacctg ttgaagatca ccaacctacg agtgaactta acccggcttc acacactggg    3000
agacaacttg cttgacccac ggagggagat ccgggaaaaa tactattatg ctctctatga    3060
acttgtcatc cgtggcaact gcttctgcta tggccacgcc tcacagtgtg cgcctgcacc    3120
aggggcgccg gcccatgctg agggcatggt aagggacttc ggatgactgg aacagggttg    3180
ccggggaggg acaggcattt ctagatggtg ccgtcaacct cccctcgtat ctgcacaggt    3240
acacggagcc tgtatctgca agcacaatac tcgtggactc aactgtgagc agtgtcagga    3300
tttctatcag gaccttccct ggcaccctgc agaggacggc catactcacg cctgtcggag    3360
tgagtgagac acagaactct aaccgggctg tgctctgggt gagccaaaaa gctagttggt    3420
caagccctaa atacctaggc ytttgtctga agggtatcag gccttgatgg cctcaaccca    3480
tgtgctctgc tacagtccaa agttggagct tgaagctaag ctgcaccaca aattctagct    3540
atggtaccat aggctgatga tactagcccc actcgcgtgt ccttacctag gacctggttt    3600
ccaattggtc tttgccttct ctccagagtg tgagtgcaac gggcatactc atagctgcca    3660
ctttgacatg gctgtctacc tggcatctgg aaatgtaagt ggaggcgtat gcgatgggtg    3720
```

-continued

```
tcagcacaac acagctgggc gccattgtga gttctgccgg cccttcttct accgtgaccc    3780
caccaaggac atgcgggacc cagctgtgtg ccgtcgtaag gctgggattg ggcatgaggc    3840
tgantctcag aactagaact aggaacgtgg attatatgac gttcccagga ttggtgtggt    3900
cagggcttgg ggtagaacca gaacagggaa agggaaggct caggatggtc actgcgatgg    3960
ggtgacttta tactctcctt tttctcagct tgtgactgtg accctatggg ttctcaagat    4020
ggtggtcgct gtgattctca tgatgaccct gtgctaggac tggtctcagg ccagtgtcgc    4080
tgcaaagaac acgtggttgg cactcgctgc cagcaatgcc gtgatggctt ctttggactt    4140
agtgccagtg accctcgagg gtgccagcgt atgtgcctcc tgccctaact cctgtgtcga    4200
cctttaaccc caggcctctt gttcttgatg cagttgaacc tgcttttact ccctaaaatg    4260
ggctgctttt cactacaggt tgccagtgta attcacgggg cacagtgcct gggagctccc    4320
cttgtgactc cagtagtgga acctgtttct gcaagcgtct ggtgaccgga catggctgtg    4380
accgctgtct ggtacgactg agggatctgg ggtcctggga tcctgggttt gttctcaaag    4440
cacatgggca agtccagtg ggtggacact gagagcctag agtctagtcc tggaagacaa    4500
gcgtctggtc tggcaggtca agggtctaga ccagtggtct ggggctttgc attcaccagt    4560
ccaagtggta aattgctgac tacctggtgg gtggcaagga ggtctgttcc tggcttccag    4620
caattccttt tccctagcct ggccactggg gcctgagcca tgacctgctg ggctgccgtc    4680
cctgtgactg tgatgtgggc ggtgccttgg atcctcagtg agtattgtta caggtgcttg    4740
ggaggtggat gggaaggcga agcatgggtc ctttggtaac cacagcattc ctcaggtgtg    4800
atgaggccac cggtcagtgc ccgtgccgcc aacacatgat tgggcggcgc tgcgaacaag    4860
tgcagcctgg ctacttccgg ccttttctgg accatttaac ctgggaggct gaggctgccc    4920
aagggcagtg ggagcactca tatgatgtgg gtggtgtggt agagaggagg ggttgtgggt    4980
ggtgtcttgg ggggtctagg ttgctattca gtctgggggg aggtcttggc acaggacatg    5040
gtgtttgggg ctggctgtgg cagaagagac agtggttcac ctgacacctc atctctgctt    5100
tgactgcatt gactcaggt gcttgagtg gtagagcggc tggtgaccaa ccagagagact    5160
ccgtcctgga ctggcccagg ctttgtgcgg ctgcgagaag gtcaggaagt ggagttcctg    5220
gtgacctctt tgcctagggc catggactat gacctgctac tgcgctggga gccccaggtt    5280
agaccctgtg gtggctgacc tgtgctgaca ttctgggtgt ggaagcaccc tctccactgt    5340
cctctctccc caggtccctg agcaatgggc agagctggaa ctgatggtgc agcgtccggg    5400
gcctgtgtct gctcacagtc cgtgcgggca tgtgctgcct aaggatgacc gcattcaggg    5460
gatgcttcac ccaaacacca ggtgaggcgg ngggtaagga ttgcccacag acctcctgaa    5520
agactgacat tgcgctgtgt tgttccttct ttaagtccct cctcctggct gctgttcgtc    5580
aggtccatgg ctgtgactca caggaaagac atagataaca catggcctgc ttcctcaagg    5640
gtataagttt cagaaggcaa gacattaatt ggtctgttac tccgaaacag ccttatgatg    5700
gtgacagttg cagtggcgta agatatgtaa ctggactagt taaggttttg ttacatttta    5760
gaagtaatta tttcctgtat cttttcctc actactctct gctcttctct tctcttctct    5820
tctcttctct tctcttctct actcttctct tctctactct actagtctaa acttatcttc    5880
tgctcttacc tctctctctc tctcaacctg agacagggtt tctctgtata gccccagggt    5940
gtcctggaac tcactac                                                   5957
```

<210> SEQ ID NO 6
<211> LENGTH: 1799

<212> TYPE: PRT
<213> ORGANISM: Mus musculus

<400> SEQUENCE: 6

```
Met Glu Trp Ala Ser Gly Glu Pro Gly Arg Gly Arg Gln Gly Gln Pro
 1               5                  10                  15

Leu Pro Trp Glu Leu Arg Leu Gly Leu Leu Ser Val Leu Ala Ala
            20                  25                  30

Thr Leu Ala Gln Ala Pro Ser Leu Asp Val Pro Gly Cys Ser Arg Gly
        35                  40                  45

Ser Cys Tyr Pro Ala Thr Gly Asp Leu Leu Val Gly Arg Ala Asp Arg
 50                  55                  60

Leu Thr Ala Ser Ser Thr Cys Gly Leu His Ser Pro Gln Pro Tyr Cys
 65                  70                  75                  80

Ile Val Ser His Leu Gln Asp Glu Lys Lys Cys Phe Leu Cys Asp Ser
                 85                  90                  95

Arg Arg Pro Phe Ser Ala Arg Asp Asn Pro Asn Ser His Arg Ile Gln
            100                 105                 110

Asn Val Val Thr Ser Phe Ala Pro Gln Arg Arg Thr Ala Trp Trp Gln
        115                 120                 125

Ser Glu Asn Gly Val Pro Met Val Thr Ile Gln Leu Asp Leu Glu Ala
130                 135                 140

Glu Phe His Phe Thr His Leu Ile Met Thr Phe Lys Thr Phe Arg Pro
145                 150                 155                 160

Ala Ala Met Leu Val Glu Arg Ser Ala Asp Phe Gly Arg Thr Trp His
                165                 170                 175

Val Tyr Arg Tyr Phe Ser Tyr Asp Cys Gly Ala Asp Phe Pro Gly Ile
            180                 185                 190

Pro Leu Ala Pro Pro Arg Arg Trp Asp Asp Val Val Cys Glu Ser Arg
        195                 200                 205

Tyr Ser Glu Ile Glu Pro Ser Thr Glu Gly Glu Val Ile Tyr Arg Val
210                 215                 220

Leu Asp Pro Ala Ile Pro Ile Pro Asp Pro Tyr Ser Ser Arg Ile Gln
225                 230                 235                 240

Asn Leu Leu Lys Ile Thr Asn Leu Arg Val Asn Leu Thr Arg Leu His
                245                 250                 255

Thr Leu Gly Asp Asn Leu Leu Asp Pro Arg Arg Glu Ile Arg Glu Lys
            260                 265                 270

Tyr Tyr Tyr Ala Leu Tyr Glu Leu Val Ile Arg Gly Asn Cys Phe Cys
        275                 280                 285

Tyr Gly His Ala Ser Gln Cys Ala Pro Ala Pro Gly Ala Pro Ala His
290                 295                 300

Ala Glu Gly Met Val His Gly Ala Cys Ile Cys Lys His Asn Thr Arg
305                 310                 315                 320

Gly Leu Asn Cys Glu Gln Cys Gln Asp Phe Tyr Gln Asp Leu Pro Trp
                325                 330                 335

His Pro Ala Glu Asp Gly His Thr His Ala Cys Arg Lys Cys Glu Cys
            340                 345                 350

Asn Gly His Thr His Ser Cys His Phe Asp Met Ala Val Tyr Leu Ala
        355                 360                 365

Ser Gly Asn Val Ser Gly Gly Val Cys Asp Gly Cys Gln His Asn Thr
370                 375                 380

Ala Gly Arg His Cys Glu Phe Cys Arg Pro Phe Phe Tyr Arg Asp Pro
385                 390                 395                 400
```

-continued

```
Thr Lys Asp Met Arg Asp Pro Ala Val Cys Arg Pro Cys Asp Cys Asp
            405                 410                 415
Pro Met Gly Ser Gln Asp Gly Gly Arg Cys Asp Ser His Asp Asp Pro
            420                 425                 430
Val Leu Gly Leu Val Ser Gly Gln Cys Arg Cys Lys Glu His Val Val
            435                 440                 445
Gly Thr Arg Cys Gln Gln Cys Arg Asp Gly Phe Phe Gly Leu Ser Ala
            450                 455                 460
Ser Asp Pro Arg Gly Cys Gln Arg Cys Gln Cys Asn Ser Arg Gly Thr
465                 470                 475                 480
Val Pro Gly Ser Ser Pro Cys Asp Ser Ser Gly Thr Cys Phe Cys
            485                 490                 495
Lys Arg Leu Val Thr Gly His Gly Cys Asp Arg Cys Leu Pro Gly His
            500                 505                 510
Trp Gly Leu Ser His Asp Leu Leu Gly Cys Arg Pro Cys Asp Cys Asp
            515                 520                 525
Val Gly Gly Ala Leu Asp Pro Gln Cys Asp Glu Ala Thr Gly Gln Cys
            530                 535                 540
Pro Cys Arg Gln His Met Ile Gly Arg Arg Cys Glu Gln Val Gln Pro
545                 550                 555                 560
Gly Tyr Phe Arg Pro Phe Leu Asp His Leu Thr Trp Glu Ala Glu Ala
            565                 570                 575
Ala Gln Gly Gln Val Leu Glu Val Val Glu Arg Leu Val Thr Asn Arg
            580                 585                 590
Glu Thr Pro Ser Trp Thr Gly Pro Gly Phe Val Arg Leu Arg Glu Gly
            595                 600                 605
Gln Glu Val Glu Phe Leu Val Thr Ser Leu Pro Arg Ala Met Asp Tyr
            610                 615                 620
Asp Leu Leu Leu Arg Trp Glu Pro Gln Val Pro Glu Gln Trp Ala Glu
625                 630                 635                 640
Leu Glu Leu Met Val Gln Arg Pro Gly Pro Val Ser Ala His Ser Pro
            645                 650                 655
Cys Gly His Val Leu Pro Lys Asp Asp Arg Ile Gln Gly Met Leu His
            660                 665                 670
Pro Asn Thr Arg Val Leu Val Phe Pro Arg Pro Val Cys Leu Glu Pro
            675                 680                 685
Gly Ile Ser Tyr Lys Leu Lys Leu Lys Leu Ile Gly Thr Gly Gly Arg
            690                 695                 700
Ala Gln Pro Glu Thr Ser Tyr Ser Gly Leu Leu Ile Asp Ser Leu Val
705                 710                 715                 720
Leu Gln Pro His Val Leu Val Leu Glu Met Phe Ser Gly Gly Asp Ala
            725                 730                 735
Ala Ala Leu Glu Arg Arg Thr Thr Phe Glu Arg Tyr Arg Cys His Glu
            740                 745                 750
Glu Gly Leu Met Pro Ser Lys Ala Pro Leu Ser Glu Thr Cys Ala Pro
            755                 760                 765
Leu Leu Ile Ser Val Ser Ala Leu Ile Tyr Asn Gly Ala Leu Pro Cys
            770                 775                 780
Gln Cys Asp Pro Gln Gly Ser Leu Ser Ser Glu Cys Ser Pro His Gly
785                 790                 795                 800
Gly Gln Cys Arg Cys Lys Pro Gly Val Val Gly Arg Arg Cys Asp Val
            805                 810                 815
```

```
Cys Ala Thr Gly Tyr Tyr Gly Phe Gly Pro Ala Gly Cys Gln Ala Cys
            820                 825                 830

Gln Cys Ser Pro Asp Gly Ala Leu Ser Ala Leu Cys Glu Gly Thr Ser
        835                 840                 845

Gly Gln Cys Pro Cys Arg Pro Gly Ala Phe Gly Leu Arg Cys Asp His
    850                 855                 860

Cys Gln Arg Gly Gln Trp Gly Phe Pro Asn Cys Arg Pro Cys Val Cys
865                 870                 875                 880

Asn Gly Arg Ala Asp Glu Cys Asp Thr His Thr Gly Ala Cys Leu Gly
                885                 890                 895

Cys Arg Asp Tyr Thr Gly Gly Glu His Cys Glu Arg Cys Ile Ala Gly
            900                 905                 910

Phe His Gly Asp Pro Arg Leu Pro Tyr Gly Gly Gln Cys Arg Pro Cys
        915                 920                 925

Pro Cys Pro Glu Gly Pro Gly Ser Gln Arg His Phe Ala Thr Ser Cys
    930                 935                 940

His Arg Asp Gly Tyr Ser Gln Gln Ile Val Cys His Cys Arg Ala Gly
945                 950                 955                 960

Tyr Thr Gly Leu Arg Cys Glu Ala Cys Ala Pro Gly Pro Phe Gly Asp
                965                 970                 975

Pro Ser Lys Pro Gly Gly Arg Cys Gln Leu Cys Glu Cys Ser Gly Asn
            980                 985                 990

Ile Asp Pro Met Asp Pro Asp Ala Cys Asp Pro His Thr Gly Gln Cys
        995                 1000                1005

Leu Arg Cys Leu His Asn Thr Glu Gly Pro His Cys Gly Tyr Cys Lys
    1010                1015                1020

Pro Gly Phe His Gly Gln Ala Ala Arg Gln Ser Cys His Arg Cys Thr
1025                1030                1035                1040

Cys Asn Leu Leu Gly Thr Asp Pro Arg Arg Cys Pro Ser Thr Asp Leu
                1045                1050                1055

Cys His Cys Asp Pro Ser Thr Gly Gln Cys Pro Cys Leu Pro His Val
            1060                1065                1070

Gln Gly Leu Asn Cys Asp His Cys Ala Pro Asn Phe Trp Asn Phe Thr
        1075                1080                1085

Ser Gly Arg Gly Cys Gln Pro Cys Ala Cys His Pro Ser Arg Ala Arg
    1090                1095                1100

Gly Pro Thr Cys Asn Glu Phe Thr Gly Gln Cys His Cys His Ala Gly
1105                1110                1115                1120

Phe Gly Gly Arg Thr Cys Ser Glu Cys Gln Glu Leu Tyr Trp Gly Asp
                1125                1130                1135

Pro Gly Leu Gln Cys Arg Ala Cys Asp Cys Asp Pro Arg Gly Ile Asp
            1140                1145                1150

Lys Pro Gln Cys His Arg Ser Thr Gly His Cys Ser Cys Arg Pro Gly
        1155                1160                1165

Val Ser Gly Val Arg Cys Asp Gln Cys Ala Arg Gly Phe Ser Gly Val
    1170                1175                1180

Phe Pro Ala Cys His Pro Cys His Ala Cys Phe Gly Asp Trp Asp Arg
1185                1190                1195                1200

Val Val Gln Asp Leu Ala Ala Arg Thr Arg Arg Leu Glu Gln Trp Ala
                1205                1210                1215

Gln Glu Leu Gln Gln Thr Gly Val Leu Gly Ala Phe Glu Ser Ser Phe
            1220                1225                1230

Leu Asn Met Gln Gly Lys Leu Gly Met Val Gln Ala Ile Met Ser Ala
```

-continued

```
            1235                1240                1245

Arg Asn Ala Ser Ala Ser Thr Ala Lys Leu Val Glu Ala Thr Glu
        1250                1255                1260

Gly Leu Arg His Glu Ile Gly Lys Thr Thr Glu Arg Leu Thr Gln Leu
1265                1270                1275                1280

Glu Ala Glu Leu Thr Ala Val Gln Asp Glu Asn Phe Asn Ala Asn His
                1285                1290                1295

Ala Leu Ser Gly Leu Glu Arg Asp Gly Phe Ala Leu Asn Leu Thr Leu
        1300                1305                1310

Arg Gln Leu Asp Gln His Leu Glu Ile Leu Lys His Ser Asn Phe Leu
        1315                1320                1325

Gly Ala Tyr Asp Ser Ile Arg His Ala His Ser Gln Ser Thr Glu Ala
        1330                1335                1340

Glu Arg Arg Ala Asn Ala Ser Thr Phe Ala Val Pro Ser Pro Val Ser
1345                1350                1355                1360

Asn Ser Ala Asp Thr Arg Arg Thr Glu Val Leu Met Gly Ala Gln
                1365                1370                1375

Lys Glu Asn Phe Asn Arg Gln His Leu Ala Asn Gln Gln Ala Leu Gly
        1380                1385                1390

Arg Leu Ser Ala His Ala His Thr Leu Ser Leu Thr Gly Ile Asn Glu
        1395                1400                1405

Leu Val Cys Gly Ala Pro Gly Asp Ala Pro Cys Ala Thr Ser Pro Cys
        1410                1415                1420

Gly Gly Ala Gly Cys Arg Asp Glu Asp Gly Gln Pro Arg Cys Gly Gly
1425                1430                1435                1440

Leu Gly Cys Ser Gly Ala Ala Pro Ala Asp Leu Ala Leu Gly Arg
        1445                1450                1455

Ala Arg His Ser Gln Ala Glu Leu Gln Arg Ala Leu Val Glu Gly Gly
        1460                1465                1470

Gly Ile Leu Ser Arg Val Ser Glu Thr Arg Arg Gln Ala Glu Ala Ala
        1475                1480                1485

Gln Gln Arg Ala Gln Ala Ala Leu Asp Lys Ala Asn Ala Ser Arg Gly
        1490                1495                1500

Gln Val Glu Gln Ala Asn Gln Glu Leu Arg Glu Leu Ile Gln Asn Val
1505                1510                1515                1520

Lys Asp Phe Leu Ser Gln Glu Gly Ala Asp Pro Asp Ser Ile Glu Met
                1525                1530                1535

Val Ala Thr Arg Val Leu Asp Ile Ser Ile Pro Ala Ser Pro Glu Gln
            1540                1545                1550

Ile Gln Arg Leu Ala Ser Glu Ile Ala Glu Arg Val Arg Ser Leu Ala
        1555                1560                1565

Asp Val Asp Thr Ile Leu Ala His Thr Met Gly Asp Val Arg Arg Ala
        1570                1575                1580

Glu Gln Leu Leu Gln Asp Ala His Arg Ala Arg Ser Arg Ala Glu Gly
1585                1590                1595                1600

Glu Arg Gln Lys Ala Glu Thr Val Gln Ala Ala Leu Glu Glu Ala Gln
                1605                1610                1615

Arg Ala Gln Gly Ala Ala Gln Gly Ala Ile Arg Gly Ala Val Val Asp
        1620                1625                1630

Thr Gln Asn Thr Glu Gln Thr Leu Gln Arg Val Gln Glu Arg Met Ala
        1635                1640                1645

Gly Ala Glu Lys Ser Leu Asn Ser Ala Gly Glu Arg Ala Arg Gln Leu
        1650                1655                1660
```

```
Asp Ala Leu Leu Glu Ala Leu Lys Leu Lys Arg Ala Gly Asn Ser Leu
1665                1670                1675                1680

Ala Ala Ser Thr Ala Glu Glu Thr Ala Gly Ser Ala Gln Ser Arg Ala
            1685                1690                1695

Arg Glu Ala Glu Lys Gln Leu Arg Glu Gln Val Gly Asp Gln Tyr Gln
        1700                1705                1710

Thr Val Arg Ala Leu Ala Glu Arg Lys Ala Glu Gly Val Leu Ala Ala
    1715                1720                1725

Gln Ala Arg Ala Glu Gln Leu Arg Asp Glu Ala Arg Asp Leu Leu Gln
        1730                1735                1740

Ala Ala Gln Asp Lys Leu Gln Arg Leu Gln Glu Leu Glu Gly Thr Tyr
1745                1750                1755                1760

Glu Glu Asn Glu Arg Ala Leu Glu Gly Lys Ala Ala Gln Leu Asp Gly
                1765                1770                1775

Leu Glu Ala Arg Met Arg Ser Val Leu Gln Ala Ile Asn Leu Gln Val
                1780                1785                1790

Gln Ile Tyr Asn Thr Cys Gln
            1795

<210> SEQ ID NO 7
<211> LENGTH: 5683
<212> TYPE: DNA
<213> ORGANISM: Homo sapiens

<400> SEQUENCE: 7
ccgcccggtg ttgcgctcct tcccagaatc cgctccggcc tttccttcct gccgcgattc      60
ccaactttgc tcaaagtcgc cggactctaa gctgtcggag ggaccgctgg acagacctgg     120
gaactgacag agggcctgga gggaaatagg ccaaagaccc acaggatgga gctgacctca     180
accgaaagag ggaggggaca gcctctgccc tgggaacttc gactgcccct actgctaagc     240
gtgctggctg ccacactggc acaggccccct gccccggatg tccctggctg ttccagggga     300
agctgctacc ccgccacggc cgacctgctg gtgggccgag ctgacagact gactgcctca     360
tccacttgtg gcctgaatgg ccgccagccc tactgcatcg tcagtcacct gcaggacgaa     420
aagaagtgct tcctttgtga ctcccggcgc cccttctctg ctagagacaa cccacacacc     480
catcgcatcc agaatgtagt caccagcttt gcaccacagc ggcgggcagc ttggtggcag     540
tcacagaatg gtatccctgc ggtcaccatc cagctggacc tggaggctga gtttcatttc     600
acacacctca ttatgacctt caagacattt cgccctgctg ccatgctggt cgaacgctca     660
gcagactttg gccgcacctg gcatgtgtac cgatatttct cctatcactg tggggctgac     720
ttcccaggag tcccactagc accccacgg cactgggatg atgtagtctg tgagtcccgc     780
tactcagaga ttgagccatc cactgaaggc gaggtcatct atcgtgtgct ggaccctgcc     840
atccctatcc agacccccta cagctcacgg attcagaacc tgttgaagat caccaaccta     900
cgggtgaacc tgactcgtct cacacgttg ggagacaacc tactcgaccc acggagggag     960
atccgagaga agtactacta tgccctctat gagctggttg tacgtggcaa ctgcttctgc    1020
tacggacacg cctcagagtg tgcacccgcc ccaggggcac cagcccatgc tgagggcatg    1080
gtgcacggag cttgcatctg caaacacaac acacgtggcc tcaactgcga gcagtgtcag    1140
gatttctatc gtgaccctgc ctggcgtccg gctgaggacg gccatagtca tgcctgtagg    1200
aagtgtgatc ggcatgggca cccacacagc tgccactccg acatggccgt atacctcgga    1260
tctggcaatg tgagtggagg tgtgtgtgat ggatgtcagc ataacacagc gtggcgccac    1320
```

-continued

```
tgtgagctct gtcggccctt cttctaccgt gacccaacca aggacctgcg ggatccggct    1380
gtgtgccgct cctgtgattg tgaccccatg ggttctcaag acggtggtcg ctgtgattcc    1440
catgatgacc ctgcactggg actggtctcc ggccagtgtc gctgcaaaga acacgtggtg    1500
ggcactcgct gccagcaatg ccgtgatggc ttctttgggc tcagcatcag tgacccgtct    1560
gggtgccggc gatgtcaatg taatgcacgg ggcacagtgc tgggagcac tccttgtgac     1620
cccaacagtg gatcctgtta ctgcaaacgt ctagtgactg gacgtggatg tgaccgctgc    1680
ctgcctggcc actggggcct gagcctcgac ctgctcggct gccgccctg tgactgcgac     1740
gtgggtggtg ctttggatcc ccagtgtgat gagggcacag gtcaatgcca ctgccgccag    1800
cacatggttg ggcgacgctg tgagcaggtg caacctggct acttccggcc cttcctggac    1860
cacctaattt gggaggctga aacacccga gggcaggtgc tcgatgtggt ggagcgcctg     1920
gtgaccccg gggaaactcc atcctggact ggctcaggct tcgtgcgact acaggaaggt     1980
cagaccctgg agttcctggt ggcctctgtg ccgaacgcga tggactatga cctgctgctg    2040
cgcttagagc cccaggtccc tgagcaatgg gcagagttgg aactgattgt gcagcgtcca    2100
gggcctgtgc ctgcccacag cctgtgtggg catttggtgc ccagggatga tcgcatccaa    2160
gggactctgc aaccacatgc caggtacttg atatttccta atcctgtctg ccttgagcct    2220
ggtatctcct acaagctgca tctgaagctg gtacggacag ggggaagtgc ccagcctgag    2280
actccctact ctggacctgg cctgctcatt gactcgctgg tgctgctgcc ccgtgtcctg    2340
gtgctagaga tgtttagtgg gggtgatgct gctgccctgg agcgccaggc cacctttgaa    2400
cgctaccaat gccatgagga gggtctggtg cccagcaaga cttctccctc tgaggcctgc    2460
gcacccctcc tcatcagcct gtccacccttc atctacaatg gtgccctgcc atgtcagtgc    2520
aaccctcaag gttcactgag ttctgagtgc aaccctcatg gtggtcagtg cctgtgcaag    2580
cctggagtgg ttgggcgccg ctgtgacacg tgtgcccctg gctactatgg ctttggcccc    2640
acaggctgtc aagcctgcca gtgcagccca cgaggggcac tcagcagtct ctgtgaaagg    2700
accagtgggc aatgtctctg tcgaactggt gcctttgggc ttcgctgtga cgcctgccag    2760
cgtggccagt ggggattccc tagctgccgg ccatgtgtct gcaatgggca tgcagatgag    2820
tgcaacaccc acacaggcgc ttgcctgggc tgccgtgatc tcacaggggg tgagcactgt    2880
gaaaggtgca ttgctggttt ccacgggggac ccacggctgc catatgggc gcagtgccgg    2940
ccctgtccct gtcctgaagg ccctgggagc caacggcact ttgctacttc ttgccaccag    3000
gatgaatatt cccagcagat tgtgtgccac tgccgggcag gctatacggg gctgcgatgt    3060
gaagcttgtg cccctgggca gtttgggggac ccatcaaggc caggtggccg gtgccaactg    3120
tgtgagtgca gtgggaacat tgacccaatg gatcctgatg cctgtgaccc acaccccggg    3180
caatgcctgc gctgtttaca ccacacagag ggtccacact gtgccactc gaagcctggc     3240
ttccatggcc aggctgcccg gcagagctgt caccgctgca catgcaacct gctgggcaca    3300
aatccgcagc agtgcccatc tcctgaccag tgccactgta tccaagcag tgggcagtgc    3360
ccatgcctcc caatgtcca ggccctagct gtagaccgct gtgccccaa cttctggaac    3420
ctcaccagtg gccatggttg ccagccttgt gcctgcctcc caagcccgga agaaggcccc    3480
acctgcaacg agttcacagg gcagtgccac tgcctgtgcg gctttggagg gcggacttgt    3540
tctgagtgcc aagagctcca ctggggagac cctgggttgc agtgccatgc ctgtgattgt    3600
gactctcgtg gaatagatac acctcagtgt caccgcttca caggtcactg cacgtgccgc    3660
```

-continued

```
ccagggtgt ctggtgtgcg ctgtgaccag tgtgcccgtg gcttctcagg aatctttcct    3720
gcctgccatc cctgccatgc atgcttcggg gattgggacc gagtggtgca ggacttggca    3780
gcccgtacac agcgcctaga gcagcgggcg caggagttgc aacagacggg tgtgctgggt    3840
gcctttgaga gcagcttctg gcacatgcag gagaagctgg gcattgtgca gggcatcgta    3900
ggtgcccgca cacctcagc cgcctccact gcacagcttg tggaggccac agaggagctg    3960
cggcgtgaaa ttggggaggc cactgagcac ctgactcagc tcgaggcaga cctgacagat    4020
gtgcaagatg agaacttcaa tgccaaccat gcactaagtg gtctggagcg agataggctt    4080
gcacttaatc tcacactgcg gcagctcgac cagcatcttg acttgctcaa acattcaaac    4140
ttcctgggtg cctatgacag catccggcat gcccatagcc agtctgcaga ggcagaacgt    4200
cgtgccaata cctcagccct ggcagtacct agccctgtga gcaactcggc aagtgctcgg    4260
catcggacag aggcactgat ggatgctcag aaggaggact tcaacagcaa acacatggcc    4320
aaccagcggg cacttggcaa gctctctgcc catacccaca ccctgagcct gacagacata    4380
aatgagctgg tgtgtgggc ccagggattg catcatgatc gtacaagccc ttgtgggggt    4440
gccggctgtc gagatgagga tgggcagccg cgctgtgggg gcctcagctg caatggggca    4500
gcggctacag cagacctagc actgggccgg gcccggcaca cacaggcaga gctgcagcgg    4560
gcactggcag aaggtggtag catcctcagc agagtggctg agactcgtcg gcaggcaagc    4620
gaggcacagc agcgggccca ggcagccctg acaaggcta atgcttccag gggacaggtg    4680
gaacaggcca accaggaact tcaagaactt atccagagtg tgaaggactt cctcaaccag    4740
gaggggggctg atcctgatag cattgaaatg gtggccacac gggtgctaga gctctccatc    4800
ccagcttcag ctgagcagat ccagcacctg gcgggcgcga ttgcagagcg agtccggagc    4860
ctggcagatg tggatgcgat cctggcacgt actgtaggag atgtgcgtcg tgccgagcag    4920
ctactgcagg atgcacggcg ggcaaggagc tgggctgagg atgagaaaca gaaggcagag    4980
acagtacagg cagcactgga ggaggcccag cgggcacagg gtattgccca gggtgccatc    5040
cggggggcag tggctgacac acgggacaca gagcagaccc tgtaccaggt acaggagagg    5100
atggcaggtg cagagcgggc actgagctct gcaggtgaaa gggctcggca gttggatgct    5160
ctcctggagg ctctgaaatt gaaacgggca ggaaatagtc tggcagcctc tacagcagaa    5220
gaaacggcag gcagtgccca gggtcgtgcc caggaggctg agcagctgct acgcggtcct    5280
ctgggtgatc agtaccagac ggtgaaggcc ctagctgagc gcaaggccca aggtgtgctg    5340
gctgcacagg caagggcaga acaactgccg gatgaggctc gggacctgtt gcaagccgct    5400
caggacaagc tgcagcggct acaggaattg aaggcacct atgaggaaaa tgagcgggca    5460
ctggagagta aggcagccca gttggacggg ttggaggcca ggatgcgcag cgtgcttcaa    5520
gccatcaact tgcaggtgca gatctacaac acctgccagt gaccctgcc caaggcctac    5580
cccagttcct agcactgccc cacatgcatg tctgcctatg cactgaagag ctcttggccc    5640
ggcagggccc ccaataaacc agtgtgaacc cccaaaaaaa aaa    5683
```

<210> SEQ ID NO 8
<211> LENGTH: 1798
<212> TYPE: PRT
<213> ORGANISM: Homo sapiens

<400> SEQUENCE: 8

Met Glu Leu Thr Ser Thr Glu Arg Gly Arg Gly Gln Pro Leu Pro Trp
 1               5                  10                  15

-continued

```
Glu Leu Arg Leu Pro Leu Leu Leu Ser Val Leu Ala Ala Thr Leu Ala
             20                  25                  30

Gln Ala Pro Ala Pro Asp Val Pro Gly Cys Ser Arg Gly Ser Cys Tyr
         35                  40                  45

Pro Ala Thr Ala Asp Leu Leu Val Gly Arg Ala Asp Arg Leu Thr Ala
 50                  55                  60

Ser Ser Thr Cys Gly Leu Asn Gly Arg Gln Pro Tyr Cys Ile Val Ser
 65                  70                  75                  80

His Leu Gln Asp Glu Lys Lys Cys Phe Leu Cys Asp Ser Arg Arg Pro
                 85                  90                  95

Phe Ser Ala Arg Asp Asn Pro His Thr His Arg Ile Gln Asn Val Val
             100                 105                 110

Thr Ser Phe Ala Pro Gln Arg Ala Ala Trp Trp Gln Ser Gln Asn
         115                 120                 125

Gly Ile Pro Ala Val Thr Ile Gln Leu Asp Leu Glu Ala Glu Phe His
 130                 135                 140

Phe Thr His Leu Ile Met Thr Phe Lys Thr Phe Arg Pro Ala Ala Met
 145                 150                 155                 160

Leu Val Glu Arg Ser Ala Asp Phe Gly Arg Thr Trp His Val Tyr Arg
             165                 170                 175

Tyr Phe Ser Tyr His Cys Gly Ala Asp Phe Pro Gly Val Pro Leu Ala
             180                 185                 190

Pro Pro Arg His Trp Asp Asp Val Val Cys Glu Ser Arg Tyr Ser Glu
             195                 200                 205

Ile Glu Pro Ser Thr Glu Gly Glu Val Ile Tyr Arg Val Leu Asp Pro
 210                 215                 220

Ala Ile Pro Ile Pro Asp Pro Tyr Ser Ser Arg Ile Gln Asn Leu Leu
225                 230                 235                 240

Lys Ile Thr Asn Leu Arg Val Asn Leu Thr Arg Leu His Thr Leu Gly
             245                 250                 255

Asp Asn Leu Leu Asp Pro Arg Arg Glu Ile Arg Glu Lys Tyr Tyr Tyr
             260                 265                 270

Ala Leu Tyr Glu Leu Val Val Arg Gly Asn Cys Phe Cys Tyr Gly His
             275                 280                 285

Ala Ser Glu Cys Ala Pro Ala Pro Gly Ala Pro Ala His Ala Glu Gly
 290                 295                 300

Met Val His Gly Ala Cys Ile Cys Lys His Asn Thr Arg Gly Leu Asn
305                 310                 315                 320

Cys Glu Gln Cys Gln Asp Phe Tyr Arg Asp Leu Pro Trp Arg Pro Ala
             325                 330                 335

Glu Asp Gly His Ser His Ala Cys Arg Lys Cys Asp Arg His Gly His
             340                 345                 350

Thr His Ser Cys His Phe Asp Met Ala Val Tyr Leu Gly Ser Gly Asn
             355                 360                 365

Val Ser Gly Gly Val Cys Asp Gly Cys Gln His Asn Thr Ala Trp Arg
 370                 375                 380

His Cys Glu Leu Cys Arg Pro Phe Phe Tyr Arg Asp Pro Thr Lys Asp
385                 390                 395                 400

Leu Arg Asp Pro Ala Val Cys Arg Ser Cys Asp Cys Asp Pro Met Gly
             405                 410                 415

Ser Gln Asp Gly Gly Arg Cys Asp Ser His Asp Pro Ala Leu Gly
             420                 425                 430

Leu Val Ser Gly Gln Cys Arg Cys Lys Glu His Val Val Gly Thr Arg
```

-continued

```
            435                 440                 445
Cys Gln Gln Cys Arg Asp Gly Phe Phe Gly Leu Ser Ile Ser Asp Pro
    450                 455                 460

Ser Gly Cys Arg Arg Cys Gln Cys Asn Ala Arg Gly Thr Val Pro Gly
465                 470                 475                 480

Ser Thr Pro Cys Asp Pro Asn Ser Gly Ser Cys Tyr Cys Lys Arg Leu
                485                 490                 495

Val Thr Gly Arg Gly Cys Asp Arg Cys Leu Pro Gly His Trp Gly Leu
                500                 505                 510

Ser Leu Asp Leu Leu Gly Cys Arg Pro Cys Asp Cys Asp Val Gly Gly
                515                 520                 525

Ala Leu Asp Pro Gln Cys Asp Glu Gly Thr Gly Gln Cys His Cys Arg
    530                 535                 540

Gln His Met Val Gly Arg Arg Cys Glu Gln Val Gln Pro Gly Tyr Phe
545                 550                 555                 560

Arg Pro Phe Leu Asp His Leu Ile Trp Glu Ala Glu Asn Thr Arg Gly
                565                 570                 575

Gln Val Leu Asp Val Val Glu Arg Leu Val Thr Pro Gly Glu Thr Pro
                580                 585                 590

Ser Trp Thr Gly Ser Gly Phe Val Arg Leu Gln Glu Gly Gln Thr Leu
    595                 600                 605

Glu Phe Leu Val Ala Ser Val Pro Asn Ala Met Asp Tyr Asp Leu Leu
610                 615                 620

Leu Arg Leu Glu Pro Gln Val Pro Glu Gln Trp Ala Glu Leu Glu Leu
625                 630                 635                 640

Ile Val Gln Arg Pro Gly Pro Val Pro Ala His Ser Leu Cys Gly His
                645                 650                 655

Leu Val Pro Arg Asp Asp Arg Ile Gln Gly Thr Leu Gln Pro His Ala
                660                 665                 670

Arg Tyr Leu Ile Phe Pro Asn Pro Val Cys Leu Glu Pro Gly Ile Ser
                675                 680                 685

Tyr Lys Leu His Leu Lys Leu Val Arg Thr Gly Gly Ser Ala Gln Pro
    690                 695                 700

Glu Thr Pro Tyr Ser Gly Pro Gly Leu Leu Ile Asp Ser Leu Val Leu
705                 710                 715                 720

Leu Pro Arg Val Leu Val Leu Glu Met Phe Ser Gly Gly Asp Ala Ala
                725                 730                 735

Ala Leu Glu Arg Gln Ala Thr Phe Glu Arg Tyr Gln Cys His Glu Glu
                740                 745                 750

Gly Leu Val Pro Ser Lys Thr Ser Pro Ser Glu Ala Cys Ala Pro Leu
    755                 760                 765

Leu Ile Ser Leu Ser Thr Leu Ile Tyr Asn Gly Ala Leu Pro Cys Gln
    770                 775                 780

Cys Asn Pro Gln Gly Ser Leu Ser Ser Glu Cys Asn Pro His Gly Gly
785                 790                 795                 800

Gln Cys Leu Cys Lys Pro Gly Val Val Gly Arg Arg Cys Asp Thr Cys
                805                 810                 815

Ala Pro Gly Tyr Tyr Gly Phe Gly Pro Thr Gly Cys Gln Ala Cys Gln
                820                 825                 830

Cys Ser Pro Arg Gly Ala Leu Ser Ser Leu Cys Glu Arg Thr Ser Gly
                835                 840                 845

Gln Cys Leu Cys Arg Thr Gly Ala Phe Gly Leu Arg Cys Asp Ala Cys
    850                 855                 860
```

-continued

```
Gln Arg Gly Gln Trp Gly Phe Pro Ser Cys Arg Pro Cys Val Cys Asn
865                 870                 875                 880

Gly His Ala Asp Glu Cys Asn Thr His Thr Gly Ala Cys Leu Gly Cys
            885                 890                 895

Arg Asp Leu Thr Gly Gly Glu His Cys Glu Arg Cys Ile Ala Gly Phe
                900                 905                 910

His Gly Asp Pro Arg Leu Pro Tyr Gly Ala Gln Cys Arg Pro Cys Pro
            915                 920                 925

Cys Pro Glu Gly Pro Gly Ser Gln Arg His Phe Ala Thr Ser Cys His
930                 935                 940

Gln Asp Glu Tyr Ser Gln Gln Ile Val Cys His Cys Arg Ala Gly Tyr
945                 950                 955                 960

Thr Gly Leu Arg Cys Glu Ala Cys Ala Pro Gly Gln Phe Gly Asp Pro
                965                 970                 975

Ser Arg Pro Gly Gly Arg Cys Gln Leu Cys Glu Cys Ser Gly Asn Ile
            980                 985                 990

Asp Pro Met Asp Pro Asp Ala Cys Asp Pro His Pro Gly Gln Cys Leu
            995                 1000                1005

Arg Cys Leu His His Thr Glu Gly Pro His Cys Ala His Ser Lys Pro
1010                1015                1020

Gly Phe His Gly Gln Ala Ala Arg Gln Ser Cys His Arg Cys Thr Cys
1025                1030                1035                1040

Asn Leu Leu Gly Thr Asn Pro Gln Gln Cys Pro Ser Pro Asp Gln Cys
                1045                1050                1055

His Cys Asp Pro Ser Ser Gly Gln Cys Pro Cys Leu Pro Asn Val Gln
            1060                1065                1070

Ala Leu Ala Val Asp Arg Cys Ala Pro Asn Phe Trp Asn Leu Thr Ser
            1075                1080                1085

Gly His Gly Cys Gln Pro Cys Ala Cys Leu Pro Ser Pro Glu Glu Gly
            1090                1095                1100

Pro Thr Cys Asn Glu Phe Thr Gly Gln Cys His Cys Leu Cys Gly Phe
1105                1110                1115                1120

Gly Gly Arg Thr Cys Ser Glu Cys Gln Glu Leu His Trp Gly Asp Pro
                1125                1130                1135

Gly Leu Gln Cys His Ala Cys Asp Cys Asp Ser Arg Gly Ile Asp Thr
            1140                1145                1150

Pro Gln Cys His Arg Phe Thr Gly His Cys Thr Cys Arg Pro Gly Val
            1155                1160                1165

Ser Gly Val Arg Cys Asp Gln Cys Ala Arg Gly Phe Ser Gly Ile Phe
            1170                1175                1180

Pro Ala Cys His Pro Cys His Ala Cys Phe Gly Asp Trp Asp Arg Val
1185                1190                1195                1200

Val Gln Asp Leu Ala Ala Arg Thr Gln Arg Leu Glu Gln Arg Ala Gln
                1205                1210                1215

Glu Leu Gln Gln Thr Gly Val Leu Gly Ala Phe Glu Ser Ser Phe Trp
                1220                1225                1230

His Met Gln Glu Lys Leu Gly Ile Val Gln Gly Ile Val Gly Ala Arg
            1235                1240                1245

Asn Thr Ser Ala Ala Ser Thr Ala Gln Leu Val Glu Ala Thr Glu Glu
            1250                1255                1260

Leu Arg Arg Glu Ile Gly Glu Ala Thr Glu His Leu Thr Gln Leu Glu
1265                1270                1275                1280
```

```
Ala Asp Leu Thr Asp Val Gln Asp Glu Asn Phe Asn Ala Asn His Ala
            1285                1290                1295

Leu Ser Gly Leu Glu Arg Asp Arg Leu Ala Leu Asn Leu Thr Leu Arg
        1300                1305                1310

Gln Leu Asp Gln His Leu Asp Leu Leu Lys His Ser Asn Phe Leu Gly
    1315                1320                1325

Ala Tyr Asp Ser Ile Arg His Ala His Ser Gln Ser Ala Glu Ala Glu
1330                1335                1340

Arg Arg Ala Asn Thr Ser Ala Leu Ala Val Pro Ser Pro Val Ser Asn
1345                1350                1355                1360

Ser Ala Ser Ala Arg His Arg Thr Glu Ala Leu Met Asp Ala Gln Lys
            1365                1370                1375

Glu Asp Phe Asn Ser Lys His Met Ala Asn Gln Arg Ala Leu Gly Lys
        1380                1385                1390

Leu Ser Ala His Thr His Thr Leu Ser Leu Thr Asp Ile Asn Glu Leu
    1395                1400                1405

Val Cys Gly Ala Gln Gly Leu His His Asp Arg Thr Ser Pro Cys Gly
1410                1415                1420

Gly Ala Gly Cys Arg Asp Glu Asp Gly Gln Pro Arg Cys Gly Gly Leu
1425                1430                1435                1440

Ser Cys Asn Gly Ala Ala Ala Thr Ala Asp Leu Ala Leu Gly Arg Ala
            1445                1450                1455

Arg His Thr Gln Ala Glu Leu Gln Arg Ala Leu Ala Glu Gly Gly Ser
        1460                1465                1470

Ile Leu Ser Arg Val Ala Glu Thr Arg Arg Gln Ala Ser Glu Ala Gln
    1475                1480                1485

Gln Arg Ala Gln Ala Ala Leu Asp Lys Ala Asn Ala Ser Arg Gly Gln
    1490                1495                1500

Val Glu Gln Ala Asn Gln Glu Leu Gln Glu Leu Ile Gln Ser Val Lys
1505                1510                1515                1520

Asp Phe Leu Asn Gln Glu Gly Ala Asp Pro Asp Ser Ile Glu Met Val
            1525                1530                1535

Ala Thr Arg Val Leu Glu Leu Ser Ile Pro Ala Ser Ala Glu Gln Ile
        1540                1545                1550

Gln His Leu Ala Gly Ala Ile Ala Glu Arg Val Arg Ser Leu Ala Asp
    1555                1560                1565

Val Asp Ala Ile Leu Ala Arg Thr Val Gly Asp Val Arg Arg Ala Glu
1570                1575                1580

Gln Leu Leu Gln Asp Ala Arg Arg Ala Arg Ser Trp Ala Glu Asp Glu
1585                1590                1595                1600

Lys Gln Lys Ala Glu Thr Val Gln Ala Ala Leu Glu Glu Ala Gln Arg
            1605                1610                1615

Ala Gln Gly Ile Ala Gln Gly Ala Ile Arg Gly Ala Val Ala Asp Thr
        1620                1625                1630

Arg Asp Thr Glu Gln Thr Leu Tyr Gln Val Gln Glu Arg Met Ala Gly
    1635                1640                1645

Ala Glu Arg Ala Leu Ser Ser Ala Gly Glu Arg Ala Arg Gln Leu Asp
1650                1655                1660

Ala Leu Leu Glu Ala Leu Lys Leu Lys Arg Ala Gly Asn Ser Leu Ala
1665                1670                1675                1680

Ala Ser Thr Ala Glu Glu Thr Ala Gly Ser Ala Gln Gly Arg Ala Gln
            1685                1690                1695

Glu Ala Glu Gln Leu Leu Arg Gly Pro Leu Gly Asp Gln Tyr Gln Thr
```

-continued

```
              1700              1705              1710
Val Lys Ala Leu Ala Glu Arg Lys Ala Gln Gly Val Leu Ala Ala Gln
        1715                1720                1725
Ala Arg Ala Glu Gln Leu Pro Asp Glu Ala Arg Asp Leu Leu Gln Ala
    1730                1735                1740
Ala Gln Asp Lys Leu Gln Arg Leu Gln Glu Leu Glu Gly Thr Tyr Glu
1745                1750                1755                1760
Glu Asn Glu Arg Ala Leu Glu Ser Lys Ala Ala Gln Leu Asp Gly Leu
            1765                1770                1775
Glu Ala Arg Met Arg Ser Val Leu Gln Ala Ile Asn Leu Gln Val Gln
        1780                1785                1790
Ile Tyr Asn Thr Cys Gln
        1795

<210> SEQ ID NO 9
<211> LENGTH: 5184
<212> TYPE: DNA
<213> ORGANISM: Mus musculus

<400> SEQUENCE: 9
ccccgcaggg gaaggcgggt cctggcggcc agcgcgcggt ccgcgcccac cctagccgac      60
ggggccggca gagcgcgcgg cgtcggtgcc cttgaccatg cgggcggctg cgcttctgct     120
ggggctggcg ctgctggcac cgcgggcggc cggcgcgggc atgggcgcgt gctatgacgg     180
cgcagggcgc ccgcagcgct gcctgccggt gttcgagaac gcggcgtttg gcggctcgc     240
ccaggcctcg cacacgtgcg gcagcccgcc cgaggacttc tgtccccacg tgggcgccgc     300
gggcgcgggg gctcattgcc agcgctgcga cgccgccgac cccagcgcc accacaacgc     360
ctcctacctc accgacttcc acagccagga cgagagcacc tggtggcaga gcccgtccat     420
ggccttcggc gtgcagtacc ccacctcggt caacatcacc ctccgcctag gaaggctta     480
tgagatcacg tatgtgaggc tgaagttcca caccagtcgc cctgagagct ttgccatcta     540
caagcgcagc cgcgccgacg gcccatggga gccctaccag ttctacagcg cctcctgcca     600
gaagacctac ggccggcccg agggccagta cctgcgcccc ggcgaggacg agcgcgtggc     660
cttctgcacc tctgagttca gcgacatctc ccgctgagt ggcggcaacg tggccttctc     720
caccctggag ggccggccca gcgcctacaa cttcgaggag agccctgggc tgcaggagtg     780
ggtcaccagc accgaactcc tcatctctct agaccggctc aacacgtttg gggacgacat     840
cttcaaggac cccaaggtgc tccagtccta ctattatgcc gtgtccgact ctctgtggg     900
cggcaggtgc aagtgcaacg gcatgccagc gagtgcggc cccgacgtgg caggccagtt     960
ggcctgccgg tgccagcaca caccaccgg cacagactgt gagcgctgcc tgcccttctt    1020
ccaggaccgc ccgtgggccc ggggcaccgc cgaggctgcc cacgagtgtc tgccctgcaa    1080
ctgcagtggc cgctccgagg aatgcacgtt tgatcgggag ctcttccgca gcacaggcca    1140
cggcggcgc tgtcaccact gccgtgacca cacagctggg ccacactgtg agcgctgtca    1200
ggagaatttc tatcactggg acccgcggat gccatgccag ccctgtgact gccagtcggc    1260
aggctcccta cacctccagt gcgatgacac aggcacctgc gcctgcaagc ccacagtgac    1320
tggctggaag tgtgaccgct gtctgcccgg gttccactcg ctcagtgagg aggctgcag    1380
accctgcact tgcaatcccg ctggcagcct ggacacctgt gaccccgca gtgggcgctg    1440
cccctgcaaa gagaatgtgg aaggcaacct atgtgacaga tgtcgcccgg ggaccttaa    1500
cctgcagccc cacaatccag ctggctgcag cagctgtttc tgctatggcc actccaaggt    1560
```

-continued

```
gtgcgcgtcc actgcccagt tccaggtgca tcacatcctc agcgatttcc accagggagc    1620
cgaaggctgg tgggccagaa gtgtgggggg ctctgagcac tccccacaat ggagcccaaa    1680
tggggtcctc ctgagcccag aagacgagga ggagctcaca gcaccaggga agttcctggg    1740
agaccagcgg ttcagctatg gcagcccct catactgacc ttccgggtgc ccccgggga    1800 ctccccactc cctgtacagc tgaggctgga agggacaggc ttggccctgt ccctgaggca    1860
ctctagcctg tctggccccc aggatgccag ggcatcccag ggaggtagag ctcaggttcc    1920
actgcaggag acctccgagg acgtggcccc tccactgccc cccttccact tccagcggct    1980
cctcgccaac ctgaccagcc tccgcctccg cgtcagtccc ggcccagcc ctgccggtcc    2040 agtgttcctg actgaggtcc ggctcacatc cgcccgcca gggctttccc cgccagcctc    2100
ctgggtggag atttgttcat gtcccactgg ctacacgggc cagttctgtg aatcctgtgc    2160
tccgggatac aagagggaga tgccacaggg gggtccctat gccagctgtg tcccctgcac    2220
ctgtaaccag catggcacct gtgaccccaa cacagggatc tgtgtctgca gccaccatac    2280
cgagggccca tcctgtgaac gctgtttgcc aggtttctat ggcaaccctt cgcgggcca    2340 agccgacgac tgccagccct gtccctgccc tggccagtcg gcctgtacga ccatcccaga    2400
gagcggggag gtggtgtgta cccactgccc ccgggccag agaggcggc gctgtgaggt    2460 ctgtgatgat ggcttttttg ggacccgct ggggctcttt gggcaccccc agccctgcca    2520
ccagtgccag tgtagcggga acgtggaccc caatgccgtg gcaactgtg accccctgtc    2580 tggccactgc ctgcgctgcc tgcacaacac cacgggtgac cactgtgagc actgtcagga    2640
aggcttctac gggagcgccc tggccctcg acccgcagac aaatgcatgc cttgcagctg    2700
tcacccacag ggctcggtca gtgagcagat gccctgcgac ccagtgacag gccaatgctc    2760
ctgcctgcct catgtgactg cacgggactg cagccgctgc tacccctggct tcttcgacct    2820 ccagcctggg aggggctgcc ggagctgcaa gtgtcaccca ctgggctccc aggaggacca    2880
gtgccatccc aagactggac agtgcacctg ccgcccaggt gtcacaggcc aggcctgtga    2940
caggtgccag ctgggtttct tcggctcctc aatcaagggc tgccgggcct gcaggtgctc    3000
cccactgggc gctgcctcgg cccagtgcca ctataacggc acatgcgtgt gcaggcctgg    3060
cttcgagggc tacaaatgtg accgctgcca ctacaacttc ttcctcacgg cagacggcac    3120
acactgccag caatgtccgt cctgctacgc cctggtgaag gaggagacag ccaagctgaa    3180
ggccagactg actttgacgg aggggtggct ccaagggtcc gactgtggca gtccctgggg    3240
accactagac attctgctgg gagaggcccc aagggggac gtctaccagg gccatcacct    3300
gcttccaggg gctcgggaag ccttcctgga gcagatgatg ggcctcgagg gtgctgtcaa    3360
ggccgcccgg gagcagctgc agaggctgaa caagggtgcc cgctgtgccc aggccggatc    3420
ccagaagacc tgcacccagc tggcagacct ggaggcagtg ctggagtcct cggaagagga    3480
gattctgcat gcagctgcca ttctcgcgtc tctggagatt cctcaggaag gtcccagtca    3540
gccgaccaaa tggagccacc tggccataga ggccgtgcc ctcgccagga ccacagaga    3600 caccgccacc aagatcgcag ccactgcttg gagggccctg ctcgcctcca acaccagcta    3660
cgcgcttctc tggaatctgc tggagggaag ggtggcccta gagacccagc gggacctgga    3720
ggacaggtac caggaggtcc aggcggccca gaaagcactg aggacggctg tggcagaggt    3780
gctgcctgaa gcggaaagcg tgttggccac cgtcagcaa gttggcgcag atacagcccc    3840
gtacctggcc ttgctggctt cccgggagc tctgcctcag aagtcccggg ctgaagacct    3900
```

-continued

```
gggcctgaag gcgaaggccc tggagaagac agttgcatca tggcagcaca tggccactga   3960
ggctgcccga accctccaga ctgctgccca ggcgacgcta cggcaaacag aacccctcac   4020
aatggcgcga tctcggctca ctgcaacctt tgcctcccag ctgcaccagg ggccagagc    4080 cgccctgacc caggcttcct catctgtcca ggctgcgaca gtgactgtca tgggagccag   4140
gactctgctg gctgatctgg aaggaatgaa gctgcagttt ccccggccca aggaccaggc   4200
ggcattgcag aggaaggcag actccgtcag tgacagactc cttgcagaca cgagaaagaa   4260
gaccaagcag gcggagagga tgctgggaaa cgcggcccct ctttcctcca gtgccaagaa   4320
gaagggcaga gaagcagagg tgttggccaa ggacagtgcc aagcttgcca aggccttgct   4380
gagggagcgg aaacaggcgc accgccgtgc cagcaggctc accagccaga cgcaagccac   4440
gctccaacag gcgtcccagc aggtgctggc gtctgaagca cgcagacagg agctggagga   4500
agctgagcgg gtgggtgctg ggctgagcga gatggagcag cagatccggg aatcgcgtat   4560
ctcactggag aaggacatcg agaccttgtc agagctgctt gccaggctgg ggtcgctgga   4620
cacccatcaa gccccagccc aggccctgaa cgagactcag tgggcactag aacgcctgag   4680
gctgcagctg ggctccccgg ggtccttgca gaggaaactc agtctgctgg agcaggaatc   4740
ccagcagcag gagctgcaga tccagggctt cgagagtgac ctcgccgaga tccgcgccga   4800
caaacagaac ctggaggcca ttctgcacag cctgcccgag aactgtgcca gctggcagtg   4860
agggctgccc agatccccgg cacacactcc cccacctgct gtttacatga cccagggggt   4920
gcacactacc ccacaggtgt gcccatacag acattccccg gagccggctg ctgtgaactc   4980
gaccccgtgt ggatagtcac actccctgcc gattctgtct gtggcttctt ccctgccagc   5040
aggactgagt gtgcgtaccc agttcacctg gacatgagtg cacactctca ccoctgcaca   5100 tgcataaacg ggcacacccc agtgtcaata acatacacac gtgagggtgc atgtctgtgt   5160
gtatgaccca ataaaaaaaa aaaa                                          5184
```

<210> SEQ ID NO 10
<211> LENGTH: 1587
<212> TYPE: PRT
<213> ORGANISM: Mus musculus

<400> SEQUENCE: 10

```
Met Ala Ala Ala Leu Leu Leu Gly Leu Ala Leu Leu Ala Pro Arg
 1               5                  10                  15

Ala Ala Gly Ala Gly Met Gly Ala Cys Tyr Asp Gly Ala Gly Arg Pro
            20                  25                  30

Gln Arg Cys Leu Pro Val Phe Glu Asn Ala Ala Phe Gly Arg Leu Ala
        35                  40                  45

Gln Ala Ser His Thr Cys Gly Ser Pro Pro Glu Asp Phe Cys Pro His
    50                  55                  60

Val Gly Ala Ala Gly Ala Gly Ala His Cys Gln Arg Cys Asp Ala Ala
65                  70                  75                  80

Asp Pro Gln Arg His His Asn Ala Ser Tyr Leu Thr Asp Phe His Ser
                85                  90                  95

Gln Asp Glu Ser Thr Trp Trp Gln Ser Pro Ser Met Ala Phe Gly Val
            100                 105                 110

Gln Tyr Pro Thr Ser Val Asn Ile Thr Leu Arg Leu Gly Lys Ala Tyr
        115                 120                 125

Glu Ile Thr Tyr Val Arg Leu Lys Phe His Thr Ser Arg Pro Glu Ser
    130                 135                 140
```

```
Phe Ala Ile Tyr Lys Arg Ser Arg Ala Asp Gly Pro Trp Glu Pro Tyr
145                 150                 155                 160

Gln Phe Tyr Ser Ala Ser Cys Gln Lys Thr Tyr Gly Arg Pro Glu Gly
            165                 170                 175

Gln Tyr Leu Arg Pro Gly Glu Asp Glu Arg Val Ala Phe Cys Thr Ser
            180                 185                 190

Glu Phe Ser Asp Ile Ser Pro Leu Ser Gly Gly Asn Val Ala Phe Ser
        195                 200                 205

Thr Leu Glu Gly Arg Pro Ser Ala Tyr Asn Phe Glu Glu Ser Pro Gly
        210                 215                 220

Leu Gln Glu Trp Val Thr Ser Thr Glu Leu Leu Ile Ser Leu Asp Arg
225                 230                 235                 240

Leu Asn Thr Phe Gly Asp Asp Ile Phe Lys Asp Pro Lys Val Leu Gln
                245                 250                 255

Ser Tyr Tyr Tyr Ala Val Ser Asp Phe Ser Val Gly Gly Arg Cys Lys
                260                 265                 270

Cys Asn Gly His Ala Ser Glu Cys Gly Pro Asp Val Ala Gly Gln Leu
            275                 280                 285

Ala Cys Arg Cys Gln His Asn Thr Thr Gly Thr Asp Cys Glu Arg Cys
290                 295                 300

Leu Pro Phe Phe Gln Asp Arg Pro Trp Ala Arg Gly Thr Ala Glu Ala
305                 310                 315                 320

Ala His Glu Cys Leu Pro Cys Asn Cys Ser Gly Arg Ser Glu Glu Cys
                325                 330                 335

Thr Phe Asp Arg Glu Leu Phe Arg Ser Thr Gly His Gly Gly Arg Cys
            340                 345                 350

His His Cys Arg Asp His Thr Ala Gly Pro His Cys Glu Arg Cys Gln
        355                 360                 365

Glu Asn Phe Tyr His Trp Asp Pro Arg Met Pro Cys Gln Pro Cys Asp
        370                 375                 380

Cys Gln Ser Ala Gly Ser Leu His Leu Gln Cys Asp Asp Thr Gly Thr
385                 390                 395                 400

Cys Ala Cys Lys Pro Thr Val Thr Gly Trp Lys Cys Asp Arg Cys Leu
                405                 410                 415

Pro Gly Phe His Ser Leu Ser Glu Gly Gly Cys Arg Pro Cys Thr Cys
            420                 425                 430

Asn Pro Ala Gly Ser Leu Asp Thr Cys Asp Pro Arg Ser Gly Arg Cys
435                 440                 445

Pro Cys Lys Glu Asn Val Glu Gly Asn Leu Cys Asp Arg Cys Arg Pro
450                 455                 460

Gly Thr Phe Asn Leu Gln Pro His Asn Pro Ala Gly Cys Ser Ser Cys
465                 470                 475                 480

Phe Cys Tyr Gly His Ser Lys Val Cys Ala Ser Thr Ala Gln Phe Gln
            485                 490                 495

Val His His Ile Leu Ser Asp Phe His Gln Gly Ala Glu Gly Trp Trp
                500                 505                 510

Ala Arg Ser Val Gly Gly Ser Glu His Ser Pro Gln Trp Ser Pro Asn
            515                 520                 525

Gly Val Leu Leu Ser Pro Glu Asp Glu Glu Leu Thr Ala Pro Gly
            530                 535                 540

Lys Phe Leu Gly Asp Gln Arg Phe Ser Tyr Gly Gln Pro Leu Ile Leu
545                 550                 555                 560

Thr Phe Arg Val Pro Pro Gly Asp Ser Pro Leu Pro Val Gln Leu Arg
```

-continued

```
                565                 570                 575
Leu Glu Gly Thr Gly Leu Ala Leu Ser Leu Arg His Ser Ser Leu Ser
                580                 585                 590
Gly Pro Gln Asp Ala Arg Ala Ser Gln Gly Gly Arg Ala Gln Val Pro
                595                 600                 605
Leu Gln Glu Thr Ser Glu Asp Val Ala Pro Pro Leu Pro Pro Phe His
                610                 615                 620
Phe Gln Arg Leu Leu Ala Asn Leu Thr Ser Leu Arg Leu Arg Val Ser
625                 630                 635                 640
Pro Gly Pro Ser Pro Ala Gly Pro Val Phe Leu Thr Glu Val Arg Leu
                645                 650                 655
Thr Ser Ala Arg Pro Gly Leu Ser Pro Pro Ala Ser Trp Val Glu Ile
                660                 665                 670
Cys Ser Cys Pro Thr Gly Tyr Thr Gly Gln Phe Cys Glu Ser Cys Ala
                675                 680                 685
Pro Gly Tyr Lys Arg Glu Met Pro Gln Gly Gly Pro Tyr Ala Ser Cys
                690                 695                 700
Val Pro Cys Thr Cys Asn Gln His Gly Thr Cys Asp Pro Asn Thr Gly
705                 710                 715                 720
Ile Cys Val Cys Ser His His Thr Glu Gly Pro Ser Cys Glu Arg Cys
                725                 730                 735
Leu Pro Gly Phe Tyr Gly Asn Pro Phe Ala Gly Gln Ala Asp Asp Cys
                740                 745                 750
Gln Pro Cys Pro Cys Pro Gly Gln Ser Ala Cys Thr Thr Ile Pro Glu
                755                 760                 765
Ser Gly Glu Val Val Cys Thr His Cys Pro Pro Gly Gln Arg Gly Arg
                770                 775                 780
Arg Cys Glu Val Cys Asp Asp Gly Phe Phe Gly Asp Pro Leu Gly Leu
785                 790                 795                 800
Phe Gly His Pro Gln Pro Cys His Gln Cys Gln Cys Ser Gly Asn Val
                805                 810                 815
Asp Pro Asn Ala Val Gly Asn Cys Asp Pro Leu Ser Gly His Cys Leu
                820                 825                 830
Arg Cys Leu His Asn Thr Thr Gly Asp His Cys Glu His Cys Gln Glu
                835                 840                 845
Gly Phe Tyr Gly Ser Ala Leu Ala Pro Arg Pro Ala Asp Lys Cys Met
                850                 855                 860
Pro Cys Ser Cys His Pro Gln Gly Ser Val Ser Glu Gln Met Pro Cys
865                 870                 875                 880
Asp Pro Val Thr Gly Gln Cys Ser Cys Leu Pro His Val Thr Ala Arg
                885                 890                 895
Asp Cys Ser Arg Cys Tyr Pro Gly Phe Phe Asp Leu Gln Pro Gly Arg
                900                 905                 910
Gly Cys Arg Ser Cys Lys Cys His Pro Leu Gly Ser Gln Glu Asp Gln
                915                 920                 925
Cys His Pro Lys Thr Gly Gln Cys Thr Cys Arg Pro Gly Val Thr Gly
                930                 935                 940
Gln Ala Cys Asp Arg Cys Gln Leu Gly Phe Phe Gly Ser Ser Ile Lys
945                 950                 955                 960
Gly Cys Arg Ala Cys Arg Cys Ser Pro Leu Gly Ala Ala Ser Ala Gln
                965                 970                 975
Cys His Tyr Asn Gly Thr Cys Val Cys Arg Pro Gly Phe Glu Gly Tyr
                980                 985                 990
```

-continued

```
Lys Cys Asp Arg Cys His Tyr Asn Phe Phe Leu Thr Ala Asp Gly Thr
            995                 1000                1005
His Cys Gln Gln Cys Pro Ser Cys Tyr Ala Leu Val Lys Glu Glu Thr
           1010                 1015                1020
Ala Lys Leu Lys Ala Arg Leu Thr Leu Thr Glu Gly Trp Leu Gln Gly
1025                1030                1035                1040
Ser Asp Cys Gly Ser Pro Trp Gly Pro Leu Asp Ile Leu Leu Gly Glu
                1045                1050                1055
Ala Pro Arg Gly Asp Val Tyr Gln Gly His His Leu Leu Pro Gly Ala
                1060                1065                1070
Arg Glu Ala Phe Leu Glu Gln Met Met Gly Leu Glu Gly Ala Val Lys
            1075                1080                1085
Ala Ala Arg Glu Gln Leu Gln Arg Leu Asn Lys Gly Ala Arg Cys Ala
            1090                1095                1100
Gln Ala Gly Ser Gln Lys Thr Cys Thr Gln Leu Ala Asp Leu Glu Ala
1105                1110                1115                1120
Val Leu Glu Ser Ser Glu Glu Ile Leu His Ala Ala Ala Ile Leu
                1125                1130                1135
Ala Ser Leu Glu Ile Pro Gln Glu Gly Pro Ser Gln Pro Thr Lys Trp
            1140                1145                1150
Ser His Leu Ala Ile Glu Ala Arg Ala Leu Ala Arg Ser His Arg Asp
            1155                1160                1165
Thr Ala Thr Lys Ile Ala Ala Thr Ala Trp Arg Ala Leu Leu Ala Ser
            1170                1175                1180
Asn Thr Ser Tyr Ala Leu Leu Trp Asn Leu Leu Glu Gly Arg Val Ala
1185                1190                1195                1200
Leu Glu Thr Gln Arg Asp Leu Glu Asp Arg Tyr Gln Glu Val Gln Ala
                1205                1210                1215
Ala Gln Lys Ala Leu Arg Thr Ala Val Ala Glu Val Leu Pro Glu Ala
                1220                1225                1230
Glu Ser Val Leu Ala Thr Val Gln Gln Val Gly Ala Asp Thr Ala Pro
            1235                1240                1245
Tyr Leu Ala Leu Leu Ala Ser Pro Gly Ala Leu Pro Gln Lys Ser Arg
            1250                1255                1260
Ala Glu Asp Leu Gly Leu Lys Ala Lys Ala Leu Glu Lys Thr Val Ala
1265                1270                1275                1280
Ser Trp Gln His Met Ala Thr Glu Ala Ala Arg Thr Leu Gln Thr Ala
                1285                1290                1295
Ala Gln Ala Thr Leu Arg Gln Thr Glu Pro Leu Thr Met Ala Arg Ser
            1300                1305                1310
Arg Leu Thr Ala Thr Phe Ala Ser Gln Leu His Gln Gly Ala Arg Ala
            1315                1320                1325
Ala Leu Thr Gln Ala Ser Ser Ser Val Gln Ala Ala Thr Val Thr Val
            1330                1335                1340
Met Gly Ala Arg Thr Leu Leu Ala Asp Leu Glu Gly Met Lys Leu Gln
1345                1350                1355                1360
Phe Pro Arg Pro Lys Asp Gln Ala Ala Leu Gln Arg Lys Ala Asp Ser
                1365                1370                1375
Val Ser Asp Arg Leu Leu Ala Asp Thr Arg Lys Lys Thr Lys Gln Ala
                1380                1385                1390
Glu Arg Met Leu Gly Asn Ala Ala Pro Leu Ser Ser Ser Ala Lys Lys
            1395                1400                1405
```

-continued

```
Lys Gly Arg Glu Ala Glu Val Leu Ala Lys Asp Ser Ala Lys Leu Ala
    1410                1415                1420

Lys Ala Leu Leu Arg Glu Arg Lys Gln Ala His Arg Arg Ala Ser Arg
1425                1430                1435                1440

Leu Thr Ser Gln Thr Gln Ala Thr Leu Gln Gln Ala Ser Gln Gln Val
                1445                1450                1455

Leu Ala Ser Glu Ala Arg Arg Gln Glu Leu Glu Ala Glu Arg Val
            1460                1465                1470

Gly Ala Gly Leu Ser Glu Met Glu Gln Gln Ile Arg Glu Ser Arg Ile
            1475                1480                1485

Ser Leu Glu Lys Asp Ile Glu Thr Leu Ser Gln Leu Leu Ala Arg Leu
            1490                1495                1500

Gly Ser Leu Asp Thr His Gln Ala Pro Ala Gln Ala Leu Asn Glu Thr
1505                1510                1515                1520

Gln Trp Ala Leu Glu Arg Leu Arg Leu Gln Leu Gly Ser Pro Gly Ser
                1525                1530                1535

Leu Gln Arg Lys Leu Ser Leu Leu Glu Gln Glu Ser Gln Gln Gln Glu
            1540                1545                1550

Leu Gln Ile Gln Gly Phe Glu Ser Asp Leu Ala Glu Ile Arg Ala Asp
        1555                1560                1565

Lys Gln Asn Leu Glu Ala Ile Leu His Ser Leu Pro Glu Asn Cys Ala
    1570                1575                1580

Ser Trp Gln
1585

<210> SEQ ID NO 11
<211> LENGTH: 13
<212> TYPE: PRT
<213> ORGANISM: Mus musculus

<400> SEQUENCE: 11

Ala His Pro Val Ser Asn Ala Ile Asp Gly Thr Glu Arg
1               5                   10

<210> SEQ ID NO 12
<211> LENGTH: 9
<212> TYPE: PRT
<213> ORGANISM: Mus musculus

<400> SEQUENCE: 12

Trp Trp Gln Ser Pro Pro Leu Ser Arg
1               5

<210> SEQ ID NO 13
<211> LENGTH: 14
<212> TYPE: PRT
<213> ORGANISM: Mus musculus

<400> SEQUENCE: 13

Phe Ala Asn Ser Pro Arg Pro Asp Leu Trp Val Leu Glu Arg
1               5                   10

<210> SEQ ID NO 14
<211> LENGTH: 11
<212> TYPE: PRT
<213> ORGANISM: Mus musculus

<400> SEQUENCE: 14

Thr Asn Thr Leu Leu Gly His Leu Met Gly Lys
1               5                   10
```

```
<210> SEQ ID NO 15
<211> LENGTH: 14
<212> TYPE: PRT
<213> ORGANISM: Mus musculus

<400> SEQUENCE: 15

Phe Gly Phe Asn Pro Leu Glu Phe Glu Asn Phe Ser Trp Arg
1               5                   10

<210> SEQ ID NO 16
<211> LENGTH: 15
<212> TYPE: PRT
<213> ORGANISM: Mus musculus

<400> SEQUENCE: 16

Leu Glu Leu Glu Glu Ala Ala Thr Pro Glu Gly His Ala Val Arg
1               5                   10                  15

<210> SEQ ID NO 17
<211> LENGTH: 9
<212> TYPE: PRT
<213> ORGANISM: Mus musculus

<400> SEQUENCE: 17

Ala Gly Ala Leu Leu Pro Ala Ile Arg
1               5

<210> SEQ ID NO 18
<211> LENGTH: 7
<212> TYPE: PRT
<213> ORGANISM: Mus musculus

<400> SEQUENCE: 18

Lys Leu Ile Ala Gln Ala Arg
1               5
```